US006337070B1

(12) United States Patent
Okuno et al.

(10) Patent No.: US 6,337,070 B1
(45) Date of Patent: Jan. 8, 2002

(54) POLYPEPTIDES FOR USE IN GENERATING ANTI-HUMAN INFLUENZA VIRUS ANTIBODIES

(75) Inventors: Yoshinobu Okuno, Toyonaka; Yuji Isegawa, Takatsuki; Fuyoko Sasao, Ibaraki; Shigeharu Ueda, Nishinomiya, all of (JP)

(73) Assignee: Takara Shuzo Co., Ltd., Kyoto-Fu (JP)

( * ) Notice: Subject to any disclaimer, the term of this patent is extended or adjusted under 35 U.S.C. 154(b) by 0 days.

(21) Appl. No.: 09/004,422

(22) Filed: Jan. 8, 1998

Related U.S. Application Data

(63) Continuation of application No. 08/443,862, filed on May 22, 1995, now abandoned, which is a division of application No. 08/229,781, filed on Apr. 19, 1994, now Pat. No. 5,589,174, which is a continuation-in-part of application No. 08/054,016, filed on Apr. 29, 1993, now abandoned.

(51) Int. Cl.[7] .................... A61K 39/12; A61K 39/145; C12P 21/06; C07K 14/00; C07K 16/00
(52) U.S. Cl. .................. 424/186.1; 424/204.1; 424/206.1; 435/68.1; 530/300; 530/327; 530/330; 530/350
(58) Field of Search ................. 530/327, 330, 530/300, 350; 424/186.1, 204.1, 206.1; 435/68.1

(56) References Cited

U.S. PATENT DOCUMENTS 4,537,769 A * 8/1985 Cerini
4,625,015 A * 11/1986 Green et al.
4,920,213 A * 4/1990 Dale et al.

OTHER PUBLICATIONS

Will Min et al Cell. 19;683–696, Mar. 1980.*

Nakajima et al Virology 131:116–127, 1983.* chomik et al Arch Immunol Ther Exp 36(5), 555–66, 1988.*

David–West et al. Archiv gesamte Virusforschung 43, 377–384, 1973.*

Wiley et al Ann Rev Biochem 56: 365–94, 1987.*

* cited by examiner

Primary Examiner—Mark Navarro
(74) Attorney, Agent, or Firm—Wenderoth, Lind & Ponack, L.L.P.

(57) ABSTRACT

The invention provides an anti-human influenza virus antibody which recognizes the stem regions of haemagglutinin molecules of the H1N1 and H2N2 subtypes and has a neutralization activity but does not recognize the stem region of the H3N2 subtype and has no neutralization activity. Also provided is an immunogenic artificial polypeptide having an antigenicity substantially same as the stem region of haemagglutinin molecules, particularly lacking the globular head region of haemagglutinin molecules.

This antibody is useful in the diagnosis and treatment of influenza A virus, while the polypeptides are useful as a vaccine.

10 Claims, 6 Drawing Sheets

FIG. 3

POLYPEPTIDES FOR USE IN GENERATING ANTI-HUMAN INFLUENZA VIRUS ANTIBODIES

This is a continuation of now abandoned application Ser. No. 08/443,862 filed May 22, 1995 now abandoned, which is a divisional application of Ser. No. 08/229,781, filed Apr. 19, 1994, now issued as U.S. Pat. No. 5,589,174 on Dec. 31, 1996, which is a continuation-in-part of now abandoned application of Ser. No. 08/054,016 filed Apr. 29, 1993.

BACKGROUND OF THE INVENTION

1. Field of the Invention

This invention relates to an antibody against hemagglutinin of human influenza A virus, a polypeptide containing an antigen site recognized by the antibody, and a gene coding for said polypeptide.

2. Description of Related Art

There are three types (A, B and C) of influenza viruses and the worldwide prevalence of influenza causing a large number of deaths is caused by human influenza A virus.

Influenza A virus is further classified into various subtypes depending on the antigenicities of hemagglutinin (hereinafter referred to simply as HA) and neuraminidase (hereinafter referred to simply as NA) which are viral surface proteins. There have been known so far three subtypes of human influenza A viruses, namely, the H1N1, H2N2 and H3N2 subtypes.

The HA of influenza A virus comprises two structurally distinct regions, namely, a globular head region and a stem region. The globular head region contains a receptor binding site which is responsible for virus attachment to a target cell and participates in the hemagglutination activity of HA. On the other hand, the stem region contains a fusion peptide which is necessary for membrane fusion between the viral envelope and an endosomal membrane of the cell and thus relates to fusion activity Wiley et al., Ann. Rev. Biochem., 56, 365–394 (1987)].

All of anti-HA antibodies, which have been obtained hitherto as an antibody capable of recognizing the H1N1 and H2N2 subtypes, recognize the globular head region of HA. However, this region most frequently undergoes antigen mutation. Therefore, these antibodies are not common to the subtypes of human infleunza A virus and, further, lose the recognizing ability with antigenic changes in the HA of the virus On the other hand, Green et al. have synthesized a polypeptide based on an amino acid sequence in the stem region of HA of the H3N2 subtype and obtained antibodies against this polypeptide. However, these antibodies have a low neutralization activity (Published Japanese Translation of PCT Patent Applications from Other Countries, No. 501714/1984). Furthermore, the polypeptide per seemployed as an antigen does not react with rabbit antiviral serum obtained by immunizing with the H3N2 subtype, which suggests that there is a problem from the viewpoint of antigenicity too Cell, 28, 477–487 (1982)].

The infectivity of the HA of influenza A virus is activated when the HA is cleaved at one site with a protease. The larger polypeptide thus obtained is called HA1 while the smaller one HA2. It is believed that between these polypeptide HA2 will undergo less antigen mutation due to the subtype.

In East German Patent Laid-Open No. 228737, H. Glathe et. al. describe that HA2 is taken out by treating viral particles successively with an acid and trypsin or with a reducing agent alone.

By these treatments, however, HA molecules are destroyed in the stereostructure and irreversibly denatured. As a result, the HA2 thus obtained does not have its inherent stereostructure. In addition, the above-mentioned patent is silent whether the efficacy of the obtained HA2 as a vaccine has been specifically confirmed or not.

Human influenza A virus periodically changes types of HA and NA and thus causes wide prevalence. It is often observed that vaccinization before winter, i.e, the season of prevalence, produces no effect, since the prevalence is caused by a virus of a different type. If an antibody, which is common to virus subtypes in HA and NA molecules and capable of recognizing an antigen site hardly undergoing antigenic mutation, in particular, the configuration, and has neutralization activity for viruses, can be acquired, this antibody is usable in the diagnosis, prevention and treatment of infection with the A virus. Furthermore, the antigen site per se is useful as a vaccine.

It is an object of the present invention to provide an antibody which has a cross recognizing ability for influenza A virus subtypes and has a virus neutralization activity, an antigen site polypeptide which is usable as a vaccine, and a gene coding for said polypeptide.

SUMMARY OF THE INVENTION

To sum up, the first invention relates to an anti-human influenza virus antibody characterized by having the characteristics (a) and (b) specified below:

(a) recognizing the stem region of HA molecule of the H1N1 and H2N2 subtypes of human influenza A virus but not recognizing the stem region of a HA molecule of the H3N2 subtype thereof; and (b) having neutralization activity for the H1N1 and H2N2 subtypes of human influenza A virus but no neutralization activity for the H3N2 subtype thereof.

The second invention relates to an immunogenic artificial polypeptide characterized by having an antigenicity substantially the same as that of the stem region in HA molecule of human influenza A virus.

The third invention relates to an immunogenic artificial polypeptide characterized by having an antigenicity substantially the same as that of the stem region in HA molecule of human influenza A virus and lacking a globular head region of HA molecule.

The fourth invention relates to a gene coding for the immunogenic artificial polypeptide of the second invention.

The fifth invention relates to a gene coding for the immunogenic artificial polypeptide of the third invention.

The present inventors have conducted extensive studies and consequently found out that an antibody against an antigen site, which is conserved commonly in the stem regions of HA molecule of H1N1 and H2N2 subtypes of human influenza A virus, has a potent neutralization activity for viruses of the H1N1 and H2N2 subtypes, that this antibody is highly useful in the treatment and prevention of influenza and that a polypeptide having an antigen site which is conserved commonly in the stem region of HA molecule of human influenza A virus is useful as a vaccine. And the present inventors have found out that a polypeptide having an antigen site, which is conserved commonly in the stem regions of HA molecule of human influenza A virus, and lacking the globular head region of HA molecule of human influenza A virus is highly useful as a vaccine. And then the present inventors have created a gene coding for said polypeptides which is useful for manufacture of said polypeptides by the genetic recombination technology. Thus the present invention was completed.

Examples of the immunogenic artificial polypeptide of the present invention, which has an antigenicity substantially the same as the stem region of HA molecule of the influenza A viruses and lacks a globular head region of HA molecules, includes polypeptide which lacks a globular head region of HA molecules by artificial proteolysis, and which is expressed by the HA gene lacking specifically a globular head region of HA molecules. These polypeptides should only have the configuration which the antibody recognizing an antigen site common to the stem regions of HA molecule specifically can recognize, may lack some part of the molecule or also may have the additional amino acid sequence.

Furthermore, these polypeptides may be partially digested with a protease in the process for producing the same by the protein engineering or genetic engineering technique.

Namely, the expression "having an antigenicity substantially the same as that of the stem region in HA molecule" as used herein means that the polypeptide has ant antigenicity of both of the HA1 and HA2 in the stem region of HA molecule which is efficiently us able as a vaccine. Therefore such a polypeptide comprising HA2 alone, the inherent stereostructure of which has been destroyed due to denaturation, as the one reported by H. Glathe et. al. as cited above, is excluded from the scope of the present invention.

As examples of the immunogenic artificial polypeptide of the present invention which is the most effective as a vaccine, the following ones may be cited.

(1) An immunogenic artificial polypeptide which contains at least a TGLRN polypeptide sequence represented by the SEQ ID No. 1 in the sequence listing and a GITNKVNS-VIEK polypeptide sequence represented by the SEQ ID No. 2 in the sequence listing in the molecule and has an antigenicity wherein the configuration of these sequences is substantially the same as that of the stem region of hemagglutinin molecule of the H1N1 and H2N2 subtypes.

(2) An immunogenic artificial polypeptide which contains at least a TGMRN polypeptide sequence represented by the SEQ ID No. 3 in the sequence listing and a QINGKLNR (L/V) IEK polypeptide sequence represented by the SEQ ID No. 4 in the sequence listing in the molecule and has an antigenicity wherein the configuration of these sequences is substantially the same as that of the stem region of hemagglutinin molecule of the H3N2 subtype.

(3) An immunogenic artificial polypeptide of the third invention of the present invention separated from hemagglutinin molecule of human influenza A virus which has been treated with a protease.

The antibody according to the present invention, which recognizes a site common to the stem regions in HA molecules of the H1N1 and H2N2 subtypes of human influenza A virus and has a neutralization activity for the H1N1 and H2N2 subtypes of human influenza A virus, can be prepared as a monoclonal antibody in the following manner. A mammal such as mouse, guinea pig or rabbit is immunized with an antigen. As the antigen, viral particles selected from among those of the H1N1 and H2N2 subtypes may be used. Examples of virus strains of the H1N1 subtype include A/Bangkok/10/83, A/Yamagata/120/86, A/Osaka/930/88, A/Suita/1/89 (each being a stock of the Research Institute for Microbial Diseases, Osaka University), A/PR/8/34 [influenza (H1N1), ATCC VR-95], A1/FM/1/47 [influenza A (H1N1), ATCC VR-97], A/New Jersey/8/76 [influenza A (H1N1), ATCC VR-897], A/NWS/33 [influenza A (H1N1), ATCC VR-219], A/Weiss/43 [influenza A (H1N1), ATCC VR-96] and A/WS/33 [influenza A (H1N1), ATCC VR-825]. Examples of strains of the H2N2 subtype include A/Okuda/57, A/Adachi/2/57, A/Kumamoto/1/65, A/Kaizuka/2/65, A/Izumi/5/65 (each being a stock of the Research Institute for Microbial Diseases, Osaka University) and A2/Japan/305/57 [influenza A (H2N2), ATCC VR-100]. Alternately, the mammal can be immunized with an HA molecule obtained from these viruses, an HA polypeptide prepared by using the genetic recombination technology, a recombinant polypeptide containing the recognition site of the antibody of the present invention, namely, the antigen site of the stem region of an HA molecule therein or a synthetic polypeptide containing the antigen site of the stem region of an HA molecule therein. Next, spleen cells obtained from the animal thus immunized are fused with myeloma cells. From the hybridomas thus obtained, cells which produce an antibody having the characteristics (A) to (C) as will be specified below are selected and incubated to thereby give the target antibody according to the present invention.

(A) It has an avidity and a neutralization activity for viruses of the above-mentioned H1N1 and H2N2 subtypes.

(B) It has neither any avidity nor any neutralization activity for viruses of the H3N2 subtype such as A/Fukuoka/C29/85, A/Sichuan/2/87, A/Ibaraki/1/90, A/Suita/1/90, A/Kitakyushu/159/93 (each being a stock of the Research Institute for Microbial Diseases, Osaka University), A/Port Chalmers/1/73 [influenza A (H3N2), ATCC VR-810] and A2/Aichi/2/68 [influenza A, ATCC VR547] and influenza B viruse strains such as B/Nagasaki/1/87 (a stock of the Research Institute for Microbial Diseases, Osaka University) and B/Allen/45 [influenza B, ATCC VR-102].

(c) It recognizes HA molecules of the H1N1 and H2N2 subtypes, does not inhibit the hemagglutination activity for which the globular head region of the HA molecule is responsible, but inhibits the membrane fusion activity for which the stem region of the HA molecule is responsible.

These hybridomas are prepared in accordance with the description of Nature, 256, 495–497 (1975). As a mouse to be immunized, a Balb/c mouse and an F1 mouse obtained by mating a Balb/c mouse with another mouse of a different series may be used. The immunization is effected, for example, thrice within 2 to 5 months by using 100 to 1000 HAU/animal of viral particles as an antigen. The feeding of the mouse and the collection of its spleen cells are carried out in a conventional manner.

As the myeloma cells, SP2/0-Ag14 (ATCC CRL1581), p3x63Ag8U.1 (ATCC CRL1597), p3x63Ag8 (ATCC TIB9) or p3x63-Ag8. 653 (ATCC CRL1580) may be suitably employed. The spleen cells and the myeloma cells are mixed together at a ratio of from 1:1 to 10:1. The fusion is effected by maintaining the mixture of these cells at 35 to 37° C. in a phosphate buffer solution (pH 7.2–7.4) containing NaCl (about 0.85%), dimethyl sulfoxide [10–20% (v/v)] and polyethylene glycol of a molecular weight of 1000 to 6000 for 1 to 5 minutes. By using an HAT medium, cells growing thereon are selected as fused cells. The fused cells are cloned by repeating the limiting dilution procedure at least thrice.

The hybridomas are incubated by a method commonly used for incubating animal cells. Thus the antibody of the present invention can be obtained in the medium. Alternately, the hybridomas may be transplanted into the peritoneal cavity of a nude mouse or a Balb/c mouse treated with pristane and grown therein. As a result, the antibody of the present invention can be accumulated in the ascites. Namely, 0.5 to 1 mg of pristans is inoculated into the peritoneal cavity of the mouse. Two to 3 weeks thereafter, $5 \times 10^6$ to $1 \times 10^7$ hybridomas are transplanted into the peritoneal cavity of the animal. Then the ascites, which is usually accumulated after 7 to 10 days, is taken out. The monoclonal antibody contained in the culture and the ascites may be purified by a conventional method.

The monoclonal antibody thus obtained recognizes the stem regions of HA molecules of the H1N1 and H2N2 subtypes and inhibits the membrane fusion activity of these viruses to thereby neutralize these viruses. Now the properties of this antibody will be described in greater detail.

(a) The results of the staining test indicate that the antibody of the present invention recognizes MDCK cells. (ATCC CCL34) infected with the H1N1 and H2N2 subtypes but does not recognize MDCK cells infected with the H3N2 subtype. The staining test is effected in accordance with the method described in J. Clin. Microbial., 28, 1308–1313 (1990) by using four antibodies, namely, the monoclonal antibody of the present invention, rabbit anti-mouse immunoglobulin G serum, goat anti-rabbit immunoglobulin G serum, and peroxidase-rabbit anti-peroxidase complex.

(b) The results of the immunoprecipitation test indicate that the antibody of the present invention recognizes HA molecules of the H1N1 and H2N2 subtypes but does not recognize an HA molecule of the H3N2 subtype.

(c) In the hemagglutination test, the antibody of the present invention does not inhibit the hemagglutination activities of the H1N1, H2N2 and H3N2 subtypes.

(d) The antibody of the present invention recognizes a common conserved region characteristic of the stem regions of HA molecules of the H1N1 and H2N2 subtypes, which is specified by analyzing genes coding for the HA molecules, but does not recognize a common conserved region characteristic of the stem region of an HA molecule of the H3N2 subtype.

A gene coding for the HA molecule (hereinafter referred to simply as HA gene) is analyzed by the following method.

MDCK cells are infected with viral particles and the infected cells are harvested on the following day. Viral RNAs in the cells are extracted by using guanidine isothiocyanate. Next, an oligonucleotide primer complementary to the 3' terminus of the negative strand RNA of each of the H1N1, H2N2 and H3N2 subtypes (for example, the primer 5 represented by the SEQ ID No. 5 in the sequence listing) is prepared and cDNAs are synthesized by using this primer. To amplify these cDNAS, another oligonucleotide primer complementary to the 3' terminus of the positive strand RNA of each of the H1N1, H2N2 and H3N2 subtypes (for example, the primer 6 represented by the SEQ ID No. 6 in the sequence listing) is prepared. Then the cDNAs can be efficiently amplified by the polymerase chain reaction (PCR) method with the use of the primers 5 and 6. An HA gene of about 1.7 kbp contained in an amplified DNA is separated by agarose gel electrophoresis and then the second PCR is effected by using, for example, the primers 5 and 6. The DNA thus amplified is centrifuged by using 20% (w/v) polyethylene glycol 6000/2.5 M NaCl to thereby give a purified precipitate fraction. Subsequently, sequence primers selected from among HA gene sequences of the subclasses of viruses are prepared. After labeling these primers with [$\gamma^{32}$P]ATP, the labeled primers are annealed with the above-mentioned purified fraction, followed by sequencing by the dideoxy method with the use of a thermal cycler [BioTechniques, 9, 66–72 (1990)].

For example, the primers 7 to 14 represented respectively by the SEQ ID Nos. 7 to 14 in the sequence listing are sequence. primers for the H1N1 subtype, the primers 15 to 23 represented. respectively by the SEQ ID Nos. 15 to 23 in the sequence listing are sequence primers for the H2N2 subtype, and the primers 24 to 26 represented respectively by the SEQ ID Nos. 24 to 26 in the sequence listing are sequence primers for the H3N2 subtype. A part of the gene coding for the stem region of the HA molecule of the H1N1 subtype can be amplified and analyzed at a high efficiency by using the primers 9 and 13 as PCR primers and the primers 11 and 12 as sequence primers. A part of the gene coding for the stem region of the HA molecule of the H2N2 subtype can be amplified and analyzed at a high efficiency by using the primers 17 and 21 as PCR primers and the primers 19 and 20 as sequence primers. Further, a part of the gene coding for the stem region of the HA molecule of the H3N2 subtype can be amplified and analyzed at a high efficiency by using the primers 24 and 26 as PCR primers and the primers 25 and 26 as sequence primers.

As common conserved regions in HA molecules of H1N1 and H2N2 subtypes, the TGLRN polypeptide sequence represented by the SEQ ID No. 1 in the sequence listing and the GITNKVNSVIEK polypeptide sequence represented by the SEQ ID No. 2 in the sequence listing in the stem regions in the HA molecules of the H1N1 and H2N2 subtypes, which have been found out by the present inventors, can be cited. FIG. 1 is a schematic view of the tertiary structure of an HA molecule [Wiley et al., Nature, 289, 373–378 (1981)] and shows the position of the common conserved regions in HA molecules of H1N1 and H2N2 subtypes. As FIG. 1 shows, these polypeptide sequences, represented by the A region and the B region in the figure, are close to each other at the center of the stem region of the HA molecule. A monoclonal antibody C179, which is an example of the antibody of the present invention and produced by Hybridoma C179 (FERM BP-4517), recognizes A region (the TGLRN polypeptide sequence represented by the SEQ ID No. 1 in the sequence listing) and B region (the GITNKVNSVIEK polypeptide sequence represented by the SEQ ID No. 2 in the sequence listing) in the stem region of this HA molecule.

(e) In the neutralization activity test, the antibody of the present invention inhibits the plaque- or focus-forming abilities of the H1N1 and H2N2 subtypes but does not inhibit the plaque- or focus-forming ability of the H3N2 subtype. The neutralization activity test is carried out by the plaque reduction neutralization test or the influenza virus rapid focus reduction neutralization test described in the above-mentioned Journal of Clinical Microbiology. More specifically, the antibody is mixed with a virus and kept warm for a given period of time. Then MDCK cells are infected therewith and the neutralization activity is judged based on the reduction in the plaques or foci.

(f) In the fusion activity test, the antibody of the present invention inhibits the membrane fusion activities of the H1N1 and H2N2 subtypes but does not inhibit that of the H3N2 subtype. The fusion activity test is effected in accordance with a method described in Nature, 300, 658–659 (1982). Specifically, CV-1 cells (ATCC CCL70) are infected with a virus and treated with an antibody. Then the ability to inhibit the fusion activity is determined by examining the formation of polykaryons.

The antibody according to the present invention binds to the stem regions of HA molecules, inhibits the membrane fusion activities of the H1N1 and H2N2 subtypes and markedly neutralizes the infectious powers of these virus strains. Accordingly, the antibody of the present invention is usable in the prevention and treatment of influenza caused by the H1N1 and H2N2 subtypes. Usually, this antibody may be administered to an adult in a dose of from about 0.5 to 5000 mg, preferably from 5 to 500 mg. The antibody of the present invention may be formulated into preparations by mixing with, for example, common fillers, physiological saline, glucose solution, mannitol, methylcellulose or gelatin. This preparation may be in the form of a freeze-dried product which can be re-dissolved in an isotonic liquid such as physiological saline, a 5% glucose solution or Ringer's solution immediately before use. When the antibody of the present invention is to be administered to man, it is preferably used in the form of a chimeric antibody which is hardly recognized as a foreign substance in the human body. It is still preferable to use it as an artificial antibody obtained by transplanting the antigen recognition site alone into a human type antibody.

The antibody of this invention for example the monoclonal antibody C179 can bind to the stem regions of HA molecules, inhibit the membrane fusion activity of the H1N1 and H2N2 subtypes and markedly neutralize the infectious powers of these virus strains. Accordingly, the polypeptide capable of inducing the antibody which binds to the stem regions of HA molecules of H1N1 and H2N2 subtypes, inhibits the membrane fusion activities of the H1N1 and H2N2 subtypes and markedly neutralizes the infectious powers of these viruses (hereinafter this type antibody is referred to simply as C179 type antibody) is usable as a vaccine for influenza. Namely, the prevalence of influenza caused by the H1N1 and H2N2 subtypes can be prevented and treated by using a polypeptide, which has an antigenicity substantially the same as the stem regions of HA molecules of the H1N1 and H2N2 subtypes, as an immunogen. Examples of the immunogenic polypeptide include HA molecules prepared from the H1N1 and H2N2 subtypes and an HA polypeptide constructed by the genetic recombination technology. However, the globular head region of HA molecule is easy to become antigenic epitope and most frequently undergoes antigen mutation. So, a polypeptide having a stem region of HA molecule and lacking the globular head region of HA molecule is more effective as an antigen polypeptide which can induce C179 type antibody.

The polypeptide having an antigenicity which is substantially the same as that of the stem region of HA molecule and lacking the globular head region of HA modecule (hereinafter this polypeptide is referred to simply as stem region polypeptide) is obtained by enzymatic digestion and deletion of a globular head region of HA molecule or an HA polypeptide.

For example, the stem region polypeptide can be prepared by limitedly digesting HA molecules purified from viral particles of the H1N1 or H2N2 subtype with a protease. Alternately, the stem region polypeptide prepared by treating each of viral particles, a split vaccine obtained by inactivating viral particles, or an extract obtained by treating viral particles with a surfactant with a protease may be used. As the protease to be used herein, proteinases which can digest the globular head region in HA molecules without causing the loss of the antigenicity of the stem region are desirable. As an example of the proteinase usable in the present invention, Proteinase K (EC 3.4.21.14; manufactured by Boehringer), which is an alkaline proteinase produced by *Tritirachium album,* may be cited. By using a proteinase which is comparable to this Proteinase K in the achievement of the digestion results, the stem region polypeptide of the present invention can be prepared. It is also possible to combine a proteinase with a peptidase and conduct the treatment with the peptidase after the completion of the treatment with the proteinase. Since HA molecules exist in the form of rigid trimers in a solution, they are hardly digested with a protease. Accordingly HA molecules can be efficiently treated with the protease in the presence of a modifier such as guanidine hydrochloride or urea. The modifier may be used at such a concentration as to allow the digestion by the protease without causing irreversible denaturation of the target stem region polypeptide. When urea is used as the modifier, the digestion with the protease may be effected in the presence of from 0.1 to 8 M, preferably from 1 to 3 M of urea. This protease-treatment can be performed by using a resin such as Sepharose on which the protease has been immobilized. After the completion of the reaction, the protease-immobilized resin can be easily eliminated by centrifugation. The modifier and low molecular weight matters in the reaction mixture can be eliminated by dialysis. Thus protease-treated HA molecules can be prepared. The molecular weight of the protease-treated HA molecules can be measured by gel electrophoresis. Further, the target stem region polypeptide can be confirmed by measuring the avidity of the protease-treatment product for C179 type antybody and its hemagglutination activity.

The stem region polypeptide obtained by the protease-treatment is a polypeptide having an antigenicity substantially the same as that of the stem region in HA molecule (an avidity for C179 type antibody) and lacking the biological activity of the globular head region thereof (a hemagglutination activity). It consists of a polypeptide part originating in the HA1 stem region in HA molecule and another polypeptide part originating in HA2 therein. In this point, this polypeptide essentially differs from the above-mentioned vaccine of H. Glathe et. al. which consists of a polypeptide originating in HA2 alone.

The polypeptide having an antigenicity which is substantially the same as that of the stem region of HA molecule and. lacking the globular head region of HA modecule is obtained by genetic recombination or by chemical synthesis. For example it is possible to get the polypeptide as follows. HA gene is prepared from a viral RNA, and a gene encoding a globular head region is deleted from HA gene by using some restriction enzyme or using PCR method. Then this HA gene, which is lacking a coding region of globular head region of HA molecule, is integrated into a vector and expressed in animal cell such as CV-1 cells. Then the antigenic activity of, the stem region polypeptides can be detected by binding activity to C179 type antibody. The example of stem region polypeptide should have a common conserved region for stem region of HA molecute of H1N1 subtype and H2N2 subtype in its molecule and have the ability of inducing C179 type antibody. As the example of the stem region polypeptide, a polypeptide having a TGLRN polypeptide sequence represented by SEQ ID No. 1 in the sequence listing and a GITNKVNSVIEK polypeptide sequence represented by SEQ ID No. 2 in the sequence listing and having an antigenicity wherein the configuration of these sequence is substantially the same as that of the natural HA molecule of H1N1 and H2N2 subtypes can be obtained, isolated and used.

The example of stem region polypeptide may be the polypeptide having deletion, substitution, addetion, insertion, inversion, or replacement of amino acid, and it doesn't alter the antigenicity and C179 type antibody inducible activity. It may be the polypeptide deleting some part of C terminal and/or N terminal of stem region polypeptide or having a signal polypeptide of HA molecule at C terminal of stem region polypeptide or some part of globular head region in the stem region polypeptide.

When such a polypeptide is used as a vaccine, its antigenicity can be elevated by selecting an appropriate carrier. Examples of the carrier include albumin and polyamino acids. The vaccine of the present invention can be administered by the conventional active immunization method. More specifically, it can be administered in such an amount as to give an immunogenicity effective for the prevention or treatment one or more times by a method suitable for the preparation. The vaccine may be formulated into a pharmaceutical preparation by a conventional method. It may further contain an adjuvant for improving immune response.

The antibody, which recognizes a site common to the stem regions in HA molecules of the H3N2 subtype of human influenza A virus, can be prepared as a monoclonal antibody in the following manner. A mammal such as mouse, guinea pig or rabbit is immunized with an antigen. As the antigen, viral particles selected from among those of the H3N2 subtype may be used. Alternately, the mammal can be immunized with an HA molecule obtained from these viruses, an HA polypeptide prepared by using the genetic recombination technology, a recombinant polypeptide containing the recognition site of the antibody, namely, the antigen site of the stem region of an HA molecule therein or a synthetic polypeptide containing the antigen site of the stem region of an HA molecule therein. Next, spleen cells obtained from the animal thus immunized are fused with myeloma cells. From the hybridomas thus obtained, cells which produce an antibody having the characteristics (D) to (F) as will be specified below are selected and incubated to thereby give the target antibody.

(D) It has an avidity for virus of H3N2 subtype.

(E) It has no avidity for viruses of the H1N1 and H2N2 subtypes, and influenza B virus strains.

(F) It recognizes HA molecules of the H3N2 subtype, does not inhibit the hemagglutination activity for which the globular head region of the HA molecule is responsible.

These hybridomas are prepared in accordance with above description. As a mouse to be immunized, a Balb/c mouse and an F1 mouse obtained by mating a Balb/c mouse with another mouse of a different series may be used. The immunization is effected, for example, thrice within 2 to 5 months by using 100 to 1000 HAU/animal of viral particles as an antigen. The feeding of the mouse and the collection of its spleen cells are carried out in a conventional manner.

As the myeloma cells, SP2/0-Ag14, p3x63Ag8U.1, p3x63Ag8 or p3x63-Ag8.653 may be suitably employed. The spleen cells and the myeloma cells are mixed together at a ratio of from 1:1 to 10:1. The fusion is effected by maintaining the mixture of these cells at 35 to 37° C. in a phosphate buffer solution (pH 7.2–7.4) containing NaCl (about 0.85%), dimethyl sulfoxide [10–20% (v/v)] and polyethylene glycol of a molecular weight of 1000 to 6000 for 1 to 5 minutes. By using an HAT medium, cells growing thereon are selected as fused cells. The fused cells are cloned by repeating the limiting dilution procedure at least thrice.

The hybridomas are incubated by a method commonly used for incubating animal cells. Thus the antibody of the present invention can be obtained in the medium. Alternatively, the hybridomas may be transplanted into the peritoneal cavity of a nude mouse or a Balb/c mouse treated with pristane and grown therein. As a result, the antibody of the present invention can be accumulated in the ascites. Namely, 0.5 to 1 mg of pristans is inoculated into the peritoneal cavity of the mouse. Two to 3 weeks thereafter, $5 \times 10^6$ to $1 \times 10^7$ hybridomas are transplanted into the peritoneal cavity of the animal. Then the ascites, which is usually accumulated after 7 to 10 days, is taken out. The monoclonal antibody contained in the culture and the ascites may be purified by a conventional method.

The monoclonal antibody thus obtained recognizes the stem regions of HA molecules of the H3N2 subtype. Now the properties of this antibody will be described in greater detail.

(g) The results of the staining test indicate that the antibody recognizes MDCK cells infected with the H3N2 subtype but does not recognize MDCK cells infected with the H1N1 subtype or H2N2 subtype.

(h) The results of the immunoprecipitation test indicate that the antibody recognizes HA molecules of the H3N2 subtype but does not recognize an HA molecule of the H1N1 and H2N2 subtypes.

(i) In the hemagglutination test, the antibody does not inhibit the hemagglutination activities of the H1N1, H2N2 and H3N2 subtypes.

(j) The antibody recognizes a common conserved region characteristic of the stem regions of HA molecules of the H3N2 subtype, which is specified by analyzing genes coding for the HA molecules, but does not recognize a common conserved region characteristic of the stem region of an HA molecule of the H1N1 and H2N2 subtypes.

As common conserved regions in HA molecules of H3N2 subtype, the TGMRN polypeptide sequence represented by the SEQ ID No. 3 in the sequence listing and the QINGKLNR(L/V)IEK polypeptide sequence represented by the SEQ ID No. 4 in the sequence listing in the stem regions in the HA molecules of the H3N2 subtype, which have been found out by the present inventors, can be cited. FIG. 2 is a schematic view of the tertiary structure of an HA molecule [Wiley et al., Nature, 289, 373–378 (1981)] and shows the position of the common conserved regions in the HA molecules of H3N2 subtype. As FIG. 2 shows, these polypeptide sequences, represented by the A' region and the B' region in the figure, are close to each other at the center of the stem region of the HA molecule. A monoclonal antibody AI3C, which is an example of the antibody which binds the conserved regions and is produced by Hybridoma AI3C (FERM BP-4516), recognizes A' region (the TGMRN polypeptide sequence represented by the SEQ ID No. 3 in the sequence listing) and B' region [the GINGKLNR(L/V) IEK polypeptide sequence represented by the SEQ ID No. 4 in the sequence listing] in the stem region of this HA molecule.

The monoclonal antibody AI3C can bind specifically to the stem regions of HA molecules of H3N2 subtype (hereinafter this type antibody is referred to simply as AI3C type antibody). Accordingly, the polypeptide capable of inducing the AI3C type antibody is usable as a vaccine for influenza. Namely, the prevalence of influenza caused by the H3N2 subtype can be prevented and treated by using a polypeptide, which has an antigenicity substantially the same as the stem regions of HA molecules of the H3N2 subtype, as an immunogen. Examples of the immunogenic polypeptide include HA molecules prepared from the H3N2 subtype and an HA polypeptide constructed by the genetic recombination technology. However, the globular head region of HA molecule is easy to become antigenic epitope and most frequently undergoes antigen mutation. So, a stem region polypeptide is more effective as an antigen polypeptide which can induce AI3C type antibody.

The stem region polypeptide having an antigenicity which is substantially the same as that of the stem region of HA molecule of H3N2 subtype is obtained by enzymatic digestion and deletion of a globular head region of HA molecule or an HA polypeptide.

For example, the stem region polypeptide can be prepared by limitedly digesting HA molecules purified from viral particles of the H3N2 subtype with a protease. Alternately, the stem region polypeptide prepared by treating each of viral particles, a split vaccine obtained by inactivating viral particles, or an extract obtained by treating viral particles with a surfactant with a protease may be used. As the protease to be used herein, proteinases which can digest the globular head region in HA molecules without causing the loss of the antigenicity of the stem region are desirable. As an example of the proteinase usable in the present invention, Proteinase K may be cited. By using a proteinase which is comparable to this Proteinase K in the achievement of the digestion results, the stem region polypeptide of the present invention can be prepared. It is also possible to combine a proteinase with a peptidase and conduct the treatment with the peptidase after the completion of the treatment with the proteinase. Since HA molecules exist in the form of rigid trimers in a solution, they are hardly digested with a protease. Accordingly HA molecules can be efficiently treated with the protease in the presence of a modifier such as guanidine hydrochloride or urea. The modifier may be used at such a concentration as to allow the digestion by the protease without causing irreversible denaturation of the target stem region polypeptide. When urea is used as the modifier, the digestion with the protease may be effected in the presence of from 0.1 to 8 m, preferably from 1 to 3 M of urea. This protease-treatment can be performed by using a resin such as Sepharose on which the protease has been immobilized. After the completion of the reaction, the protease-immobilized resin can be easily eliminated by centrifugation. The modifier and low molecular weight matters in the reaction mixture can be eliminated by dialysis. Thus protease-treated HA molecules can be prepared. The molecular weight of the protease-treated HA molecules can be measured by gel electrophoresis. Further, the target stem region polypeptide can be confirmed by measuring the avidity of the protease-treatment product for AI3C type antibody and its hemagglutination activity.

The stem region polypeptide obtained by the protease-treatment is a polypeptide having an antigenicity substantially the same as that of the stem region in HA molecule (an avidity for AI3C type antibody) and lacking the biological activity of the globular head region thereof (a hemagglutination activity). It consists of a polypeptide part originating in the HA1 stem region in HA molecule and another polypeptide part originating in HA2 therein. In this point, this polypeptide essentially differs from the above-mentioned vaccine of H. Glathe et. al. which consists of a polypeptide originating in HA2 alone.

The stem region polypeptide having an antigenicity which is substantially the same as that of the stem region of HA molecule of H3N2 subtype is obtained by genetic recombination or by chemical synthesis. For example it is possible to get the polypeptide as follows. HA gene is prepared from a viral RNA of H3N2 subtype, and a gene encoding a globular head region is deleted from HA gone by using some restriction enzyme or using PCR method. Then this HA gene, which is lacking a coding region for globular head region of HA molecule, is integrated into a vector and expressed in animal cell such as CV-1 cells. Then the antigenic activity of these stem region polypeptides can be detected by binding activity to AI3C type antibody. The example of stem region polypeptide should have a common conserved region for stem region of HA molecute of H3N2 subtype in its molecule and have the ability of inducing AI3C type antibody. As the example of the stem region polypeptide, a polypeptide having a TGMRN polypeptide sequence represented by SEQ ID No. 3 in the sequence listing and a QINGKLNR(L/V)IEK polypeptide sequence represented by SEQ ID No. 4 in the sequence listing and exhibiting an antigenicity wherein the configuration of these sequence is substantially same as that natural HA molecule of H3N2 subtype can be obtained, isolated and used.

The example of stem region polypeptide may be the polypeptide having deletion, substitution, addetion, insertion, inversion, or replacement of amino acid, and it doesn't alter the antigenicity and AI3C type antibody inducible activity. It may be the polypeptide deleting some part of C terminal and/or N terminal of stem region polypeptide or having a signal polypeptide of HA molecule at C terminal of stem region polypeptide or some part of globular head region in the stem region polypeptide.

When such a polypeptide is used as a vaccine, its antigenicity can be elevated by selecting an appropriate carrier. Examples of the carrier include albumin and polyamino acids. The vaccine of the present invention can be administered by the conventional active immunization method. More specifically, it can be administered in such an amount as to give an immunogenicity effective for the prevention or treatment one or more times by a method suitable for the preparation. The vaccine may be formulated into a pharmaceutical preparation by a conventional method. It may further contain an adjuvant for improving immune response.

The dose of the stem region polypeptide of this invention to be administered depends on, for example, the properties of the vaccine employed, the concentration of the polypeptide in a preparation and the administration route. Usually it may be administered to an adult in a dose of from 1 $\mu$g to 100 mg, preferably from 10 $\mu$g to 10 mg.

BRIEF DESCRIPTION OF THE DRAWING

FIG. 3 is a graph showing the survival ratio of a group infected with influenza virus.

DETAILED DESCRIPTION OF THE PREFERRED EMBODIMENTS

Figure 1:
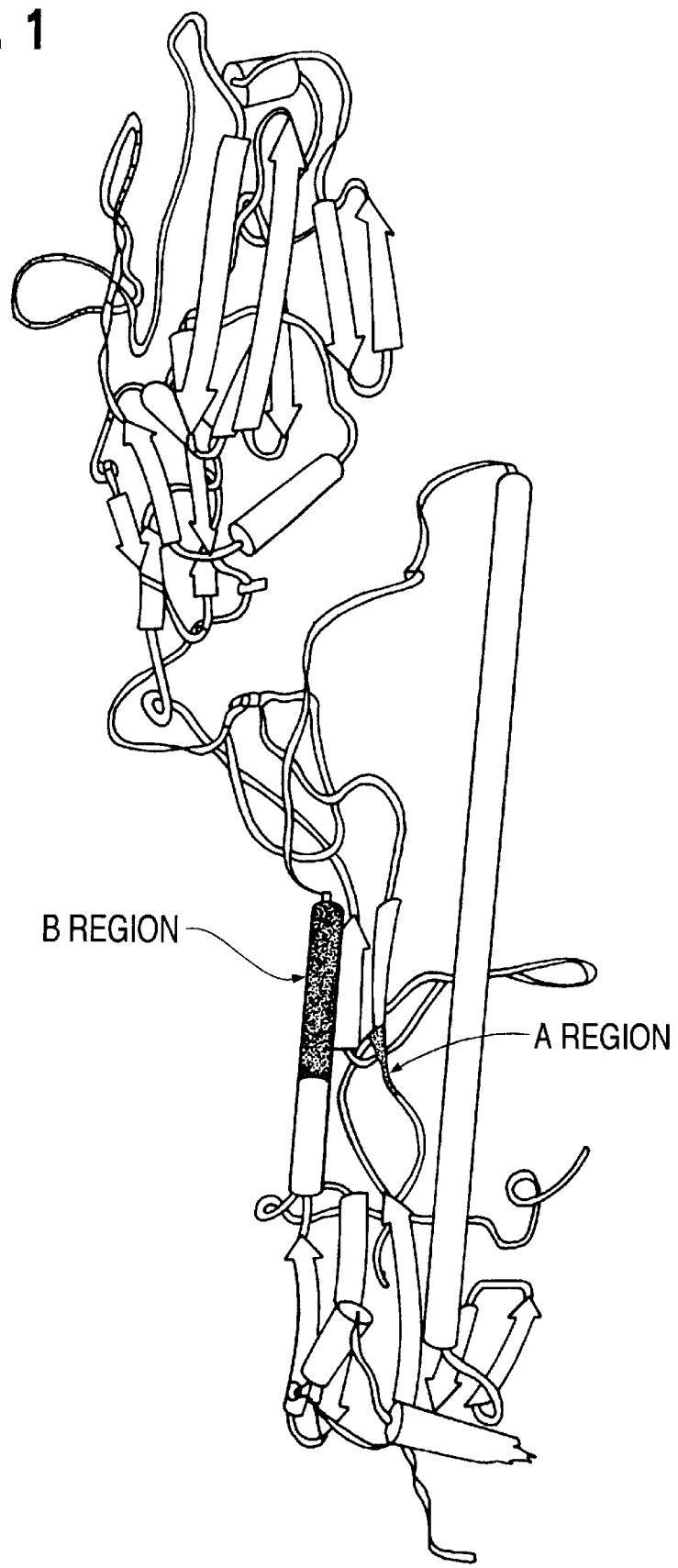
FIG. 1 is a schematic view of the tertiary structure of a HA molecule and shows the position of common conserved regions in HA molecules of H1N1 and H2N2 subtypes.

To further illustrate the present invention in greater detail, and not by way of limitation, the following Examples will be given.

EXAMPLE 1

Preparation of Viruses:

Virus strains of the H1N1 subtype used included A/PR/8/34, A/Bangkok/10/83, A/Yamagata/120/86, A/Osaka/930/88, A/Suita/1/89 and A1/FM/1/47 were used. Virus strains of the H2N2 subtype used included A/Okuda/57, A/Adachi/2/57, A/Kumamoto/1/65, A/Kaizuka/2/65 and A/Izumi/5/65 were used. Virus strains of the H3N2 subtype, used included A2/Aichi/2/68, A/Fukuoka/C29/85, A/Sichuan/2/87, A/Ibaraki/1/90, A/suita/1/90 and A/Kitakyushu/159/93 were used. A strain of influenza B virus used was B/Nagasaki/1/87. Each strain was inoculated into the allantoic cavity of an embryonated hen egg aged 11 days, incubated at 34° C. for 4 days and then harvested.

EXAMPLE 2
Preparation of Monoclonal Antibodies:

(1) Balb/c mice were immunized with two doses of A/Okuda/57 strain (320 HAU) prepared in the above Example 1, which had been suspended in Freund's complete adjuvant before use, via intraperitoneal injection one month apart. One month thereafter, the mice were boosted by intraperitoneally injecting a suspension of the same antigen (320 HAU) in PBS. Three days thereafter, the spleen of each animal was taken out and thus spleen cells were prepared.

Mouse myeloma cells were prepared by incubating p3x63Ag8 cells in a DME medium containing 10% of fetal bovine serum for 2 days after passage and then washing with physiological saline before cell fusion. The spleen cells were mixed with the myeloma cells at a ratio by cell count of 1:5. After centrifuging and removing the supernatant, the precipitated cell clusters were thoroughly loosened and then added to 1 ml of a mixture [polyethylene glycol 4000 (2 g), MEM (2 ml), and dimethyl sulfoxide] under stirring. After maintaining at 37° C. for 5 minutes, MEM was slowly added thereto so as to adjust the total amount to 10 ml. After the mixture was centrifuged, the supernatant was removed and the cell clusters were gently loosened. 30 ml of a normal medium (PRMI-1640 containing 10% of fetal bovine serum) was added thereto and the cells were slowly suspended with the use of a measuring pipet.

The suspension was pipetted into a 96-well incubation plate and incubated in an incubator containing 5% of $CO_2$ at 37° C. for 24 hours. Then HAT medium was added thereto and the incubation was continued for 10 to 14 days. Subsequently, a part of the culture supernatant was sampled and subjected to hybridoma screening.

(2) To obtain a monoclonal antibody undergoing a cross reaction between influenza A virus subtypes, the above-mentioned culture supernatant, which had not been diluted, was used as a primary antibody and a staining test on MDCK cells infected with the three subtypes (H1N1, H2N2 and H3N2) was effected. The staining test was carried out in accordance with the above-mentioned method described in Journal of Clinical Microbiology. Specifically, the MDCK cells infected with the human influenza virus subtype strains (H1N1: A/Yamagata/120/86, H2N2: A/Okuda/57, H3N2: A/Fukuoka/C29/85) were rinsed with PBS (pH 7.4) on 96-well microtiter plates (Falcon 3072; manufactured by Becton Dickinson Labware) and fixed with absolute ethanol at room temperature for 10 minutes. Then these cells were continuously treated with 4 antibodies [the above-mentioned culture supernatant containing the monoclonal antibody, rabbit anti-mouse immunoglobulin G serum (manufactured by organon Teknika-) diluted 1000-fold, goat anti-rabbit immunoglobulin G serum (manufactured by organon Teknika) diluted 500-fold, and peroxidase-rabbit anti-peroxidase complex (manufactured by organon Teknika) diluted 1000-fold, each for 40 minutes, and the cells thus treated were washed with PBS. Finally, the peroxidase reaction was effected by the method of Graham and Karnovsky [see J. Histochem. Cytochem., 14, 291–302 (1966)] with the use of 0.01% $H_2O_2$ and 0.3 mg/ml of 3,3'-diaminobenzidine tetrahydro-chloride in PBS. The stained cells were observed under an ordinary light microscope to sort antibodies recognizing respectively the H1N1 subtype-infected MDCK cells and the H2N2 subtype-infected MDCK cells. Next, the cells in the wells where the production of these antibodies had been confirmed were taken out and treated by the limiting dilution thrice to thereby clone the target cells. The hybridoma strain thus cloned was named Hybridoma C179, while the monoclonal antibody produced thereby was named monoclonal antibody C179.

The Hybridoma C179 has been deposited on Jan. 28, 1993 with National Institute of Bioscience and Human-Technology, Agency of Industrial Science and Technology (1–3, Higashai 1 chome Tsukuba-shi Ibaraki-ken,305 JAPAN), under accession number FERM P-13388, and on Dec. 27, 1993 this deposit was converted to deposit at National Institute of Bioscience and Human-Technology, Agency of Industrial Science and Technology in accordance with the Budapest Treaty under the accession number FERM BP-4517.

(3) $5\times10^6$/animal of the above-mentioned hybridomas were intraperitoneally administered to Balb/c mice treated with pristane. Ten to 21 days thereafter, the ascites of a mouse having ascites cancer thus induced was sampled and centrifuged at 3000 rpm for 5 minutes to thereby remove solid components and give an ascites fluid. This fluid contained about 5 mg/ml of the monoclonal antibody C179 (hereinafter referred to simply as C179). After purifying with Protein A-Sepharose 4B (manufactured by Pharmacia), C179 was confirmed as an antibody of the IgG2a type.

EXAMPLE 3
Properties of Monoclonal Antibody:

(1) A 100-fold dilution of the ascites fluid as described in the above Example 2-(3) was diluted stepwise and the staining test as described in the above Example 2-(2) was effected to examine the antigen recognizing characteristics of C179. The H1N1 subtype strains used included A/PR/8/34, A/Bangkok/10/83, A/Yamagata/120/86, A/Osaka/930/88, A/Suita/1/89 and A1/FM/1/47. The H2N2 subtype strains used included A/Okuda/57, A/Adachi/2/57, A/Kumamoto/1/65, A/Kaizuka/2/65 and A/Izumi/5/65. The H3N2 subtype strains used included A/Aichi/2/68, A/Fukuoka/C29/85, A/Sichuan/2/87, A/Ibaraki/1/90, A/Suita/1/90, A/Kitakyushu/159/93. Further, B/Nagasaki/1/87 was used as an influenza B virus strain.

C179 recognized all of the H1N1 subtype and H2N2 subtype strains but did not recognize the H3N2 subtype strains and the influenza virus B strain.

(2) The neutralization activity of the antibody was determined by effecting the above-mentioned influenza virus rapid focus reduction neutralization test in accordance with the description of Arch. Virol., 86, 129–135 (1985) and Microbiol. Immunol., 29, 327–335 (1985). The ascites fluid of the above Example 2-(3) was used as an antibody, to which was added thrice by volume as much a receptor destroying enzyme (RDE: manufactured by Takeda Chemical Industries, Ltd.) solution before the use. After reacting at 37° C. for 18 hours, the RDE was inactivated by heating at 56° C. for 45 minutes. Finally, a 16-fold dilution of the ascites fluid was prepared and subjected as a test sample to the determination as will be described hereinbelow.

Namely, $10^4$/well of MDCK cells were pipetted into 96-well microplates. On the next day, the abovementioned antibody (16-fold dilution) diluted in 4 steps was mixed with the equal amount of the suspension of each virus strain of 30 focus-forming units/well prepared in the above Example 3-(1), and the mixture was kept at 37° C. for 1 hour. Then 25 $\mu$l of this mixture was pipetted into the wells of the microtiter plates containing the above-mentioned MDCK cells and kept at 37° C. for 30 minutes. Then the solution in each well was removed and the well was rinsed with PBS. Next, MEM containing 0.5% of tragacanth gum (manufactured by Wako Pure Chemical Industries, Ltd.) and 5 $\mu$g/ml of trypsin was added thereto. After being kept at 37° C. for 20 to 24 hours, the solution added above was removed and each well was rinsed with PBS. Then the cells were fixed by treating with absolute ethanol at room temperature for 10 minutes. Then these cells were dried and stained in accordance with the staining test as described in the above Example 2-(2). After the completion of the staining, the cells were rinsed with tap water and dried. Then the stained foci were counted under a light microscope.

C179 inhibited the focus formation of all of the H1N1 subtype and H2N2 subtype strains and had a potent virus neutralization activity. On the other hand, it exerted no effect on the focus formation by the H3N2 subtype strains and the influenza B virus strain. The plaque reduction neutralization test gave similar results.

(3) The hemagglutination inhibition (HI) activity of the antibody was examined by the following method. The antibody (32-fold dilution) which had been treated with RDE in the same manner as the one described in the above Example 3-(2) was diluted stepwise and mixed with each virus strains (16 HAU) as described in the above Example 3-(1) to effect a reaction at room temperature for 30 minutes. After adding avian erythrocytes and well mixing, the effect of the antibody on the hemagglutination activity of each virus strain was examined. It was found that the hemagglutination activity of none of the virus strains was affected by C179.

(4) The fusion inhibition activity of the antibody was determined by the above method as described in Nature, 300, 658–659 (1982) with a few slight modifications. Namely, monolayer cultures of CV-1 cells were infected with each of the virus strains as described in the above Example 3-(1). 24 hours after the inoculation, the cells were washed twice with DMEM and then kept at 37° C. in DMEM containing 10 μg/ml of trypsin for 15 minutes. Subsequently, the cells were washed twice with DMEM and kept at 37° C. in the ascites fluid of the above Example 2-(3) diluted with DMEM for 30 minutes. Thereafter, the cells were treated for 2 minutes at 37° C. with a fusion medium (RPMI free from $Na_2CO_3$, containing 0.2% bovine serum albumin, 10 mM MES and 10 mM HEPES) adjusted to pH 5.0. Then the cells were washed twice with DMEM to remove the fusion medium, and then kept at 37° C. for 3 hours in DMEM containing 2% of fetal bovine serum. Next, the cells were fixed with absolute methanol and subjected to Giemsa's staining. Then the formation of polykaryons was examined under a light microscope.

C179 inhibited the polykaryon formation by all of the H1N1 and H2N2 subtype strains but did not inhibit the formation by the H3N2 subtype strain and the influenza B virus strain. As discussed above, C179 is an antibody which specifically recognizes the H1N1 and H2N2 subtypes, inhibits membrane fusion of viruses and exhibits a neutralization activity. Table 1 summarizes these results.

TABLE 1

| Virus | Antibody titers of C179 measured by | | | Fusion inhibition[d] |
|---|---|---|---|---|
| | Staining[a] | Neutralization[b] | HI[c] | |
| H1N1 | | | | |
| A/PR/8/34 | 1,638,400 | 512 | <32 | + |
| A/Bangkok/10/83 | 1,638,400 | 512 | <32 | + |
| A/Yamagata/120/86 | 409,600 | 1,024 | <32 | + |
| A/Osaka/930/88 | 409,600 | 512 | <32 | + |
| A/Suita/1/89 | 409,600 | 1,024 | <32 | + |
| A1/FM/1/47 | 409,600 | 512 | <32 | + |
| H2N2 | | | | |
| A/Okuda/57 | 1,638,400 | 1,024 | <32 | + |
| A/Adachi/2/57 | 1,638,400 | 1,024 | <32 | + |

TABLE 1-continued

| Virus | Antibody titers of C179 measured by | | | Fusion inhibition[d] |
|---|---|---|---|---|
| | Staining[a] | Neutralization[b] | HI[c] | |
| A/Kumamoto/1/65 | 409,600 | 1,024 | <32 | + |
| A/Kaizuka/2/65 | 409,600 | 1,048 | <32 | + |
| A/Izumi/5/65 | 409,600 | 1,024 | <32 | + |
| H3N2 | | | | |
| A2/Aichi/2/68 | <100 | <16 | <32 | − |
| A/Fukuoka/C29/85 | <100 | <16 | <32 | − |
| A/Sichuan/2/87 | <100 | <16 | <32 | − |
| A/Ibaraki/1/90 | <100 | <16 | <32 | − |
| A/Suita/1/90 | <100 | <16 | <32 | − |
| A/Kitakyushu/159/93 | <100 | <16 | <32 | − |
| B | | | | |
| B/Nagasaki/1/87 | <100 | <16 | <32 | − |

[a]Staining test.
[b]Neutralization test.
[c]Bemagglutination inhibition test.
[d]Fusion inhibition test.

In the above Table 1, each number represents the dilution ratio of the ascites fluid of the Example 2-(3), a staining titer is expressed in the maximum dilution ratio of the ascites fluid whereby cells can be stained in the staining test, while a neutralization activity is expressed in the maximum dilution ratio of the ascites fluid whereby the formation of foci can be suppressed up to a level corresponding to one half of the focus count in the control lot wherein no antibody is added. Symbol+means that polykaryon formation is completely inhibited by a 1000-fold dilution of the ascites fluid, while symbol−means that polykaryon formation is not inhibited even by using a 10-fold dilution of the ascites fluid. A 32-fold dilution of the ascites fluid shows no HI activity.

EXAMPLE 4

Determination of Epitope:

(1) It was determined by immunoprecipitation that the protein recognized by C179 was HA molecules. Specifically, MDCK cells were infected with an H2N2 subtype strain A/Okuda/57 via adsorption for 30 minutes and then incubated in MEM wherein methionine was replaced with 10 μCi of [$^{35}$S]methionine for 24 hours to thereby label the infected cells. Next, the cells were harvested and suspended again in an RIPA buffer solution [50 mM Tris (pH 7.4), 150 mM NaCl, 1 mM EDTA, 1% Nonidet P-40, 1% deoxycholate and 0.1% SDS]. After removing the insoluble matters by centrifuging, a supernatant was obtained. Then this supernatant was mixed with C179 and kept at 4° C. for 1 hour. Protein A-Sepharose CL4B beads were added thereto and kept at room temperature for 2 hours to thereby allow the beads to adsorb the immunoprecipitate. These beads were collected, washed 5 times with an RIPA buffer solution and boiled to thereby liberate the protein binding to C179. Then this protein was electrophoresed on an SDS-12.5% polyacrylamide gel. The gel was fixed, soaked in a 1 M sodium salicylate solution and dried to effect autoradiography. The labeled protein binding to C179 was thus identified with the HA molecule of A/Okuda/57 based on its electrophoretic pattern. The H1N1 subtype strains, other H2N2 subtype strains and the H3N2 subtype strain were also tested in the same manner. It was found that C179 underwent immunoprecipitation specifically together with all of the H1N1 and H2N2 subtype strains but showed no avidity on the HA molecule of the H3N2 subtype.

(2) In the presence of C179, MDCK cells infected with the H1N1 subtype or the H2N2 subtype were incubated to thereby give an antigen variant having no sensitivity to C179. More specifically, A/Suita/1/89 of the H1N1 subtype and A/Izumi/5/65 of the H2N2 subtype were used each as a parent strain. MDCK cells infected with each of these virus strains were incubated in the presence of C179. Thus variants capable of growing in the presence of C179 were separately isolated in a pure state from plaques of the MDCK cells. A variant of A/suita/1/89 was named A/Suita/1/89(R) while a variant of A/Izumi/5/65 was named A/Izumi/5/65(R). These two variants had no reactivity with C179 both in the staining test and in the neutralization test. Each of these variants was a mild infection strain having a low plaque forming ability, having no pathogenicity to mice used as test animals and capable of growing only in cultured cells.

(3) In order to specify the antigen recognition site of the antibody, a HA gene was analyzed.

(a) Synthesis of primers: Primers 5 to 26 were synthesized with a DNA synthesizer, freed from the protective group and purified by ion exchange HPLC (TSK Gel, DEAE-2SW Column). After desalting with Sep-pack C18, about 50 µg portions of DNAS were obtained.

(b) MDCK cells infected with A/Suita/1/89 were harvested and guanidine isothiocyanate was added thereto. The mixture was repeatedly sucked and discharged 5 times with the use of a syringe to thereby dissolve the cells. After the completion of the dissolution, the cell extract was layered over a cesium chloride solution and ultracentrifuged. The precipitate on the bottom of a centrifuging tube was dissolved in a buffer solution, treated with phenol and chloroform, and precipitated from ethanol. The RNA thus recovered was used as a sample of virus genome RNA. Next, cDNAs were synthesized by using the primer 5 and the cDNAs thus synthesized were amplified by the PCR method with the use of the primers 5 and 6. The cDNAs thus amplified were next separated by agarose gel electrophoresis to thereby elute a cDNA band of 1.7 kbp corresponding to the HA gene. This CDNA was further amplified by the PCR method with the use of the primers 5 and 6. To the amplified fragment was added 20% (w/v) of polyethylene glycol in 60% (v/v) of a 2.5 M NaCl solution. After centrifuging, a purified precipitate fraction was obtained.

Next, the base sequence of the gene thus purified was determined by the dideoxy method with the use of a thermal cycler as described in the above-mentioned Bio-Techniques wherein primers 7 to 14 which were sequencing primers for the H1N1 subtype labeled with [$\gamma$-$^{32}$p] were employed. More specifically, 2 pml of a primer was annealed with 1 pmol of the purified fragment by heating to 95° C. for 3 minutes and then quenching. After adding Taq polymerase, the mixture was kept at 72° C. for 10 minutes in a buffer solution containing deoxynucleotide and dideoxynucleotide, thus effecting a polymerase extension reaction. To complete the extension reaction, the reaction mixture was transferred into the thermal cycler, where a cycle of heating at 90° C. for 1 minute, at 55° C. for 2 minutes and at 72° C. for 3 minutes was repeated 10 times. After the completion of the cycling, the reaction mixture was heated to 95° C. for 3 minutes in the presence of formamide, quenched in ice and then electrophoresed on an 8% denatured polyacrylamide gel. After the completion of the electrophoresis, the gel was dried and exposed with the use of an X-ray film. Then the base sequence was read out to thereby determine the base sequence of the whole HA gene represented by the SEQ ID No. 27 in the sequence listing.

(c) The base sequence of the HA gene of A/Suita/1/89(R) was analyzed in accordance with the method as described in the above Example 4-(3)-(b). Thus the base sequence of the whole HA gene was determined and compared with the HA gene of the parent strain. As a result, it was found out that the HA gene of the variant underwent nucleotide replacement at three positions. More precisely, G of the base No. 627, G of the base No. 736 and C of the base No. 1018 in the HA gene of the parent strain mutated respectively into A, A and A. When an HA molecule was cleaved with a protease at one site, its viral infectivity was activated. After the cleavage, the larger polypeptide was called HA1 while the smaller one was called HA2. These polypeptides were bound to each other via an S—S bond. This mutation was accompanied by amino acid replacements at the 189-, 225- and 318-positions in HA1. Amino acid residues at the 189- and 225-positions were located in a highly variable region and the replacement at the 318-position (Thr→Lys; ACA→AAA on the nucleotide level) was responsible for the C179 nonreactivity of the variant. In the present specification, amino acid position in HA molecule are assigned in accordance with the H3 numbering method as described in Virus, 11, 257–266 (1961).

(d) The base sequences of HA genes of A/Izumi/5/65 and A/Izumi/5/65(R) were analyzed in accordance with the method as described in the above Example 4-(3)-(b), except that primers 15 to 23 which were sequencing primers for the H2N2 subtype were used. The base sequence of the HA gene of A/Izumi/5/65 is represented by the SEQ ID No. 28 in the sequence listing. The HA gene of this variant underwent nucleotide replacement at one position. Namely, T of the base No. 1197 in the HA gene of the parent strain mutated into A. This mutation was accompanied by an amino acid replacement at the 52-position of HA2. This replacement at the 52-position (Val→Glu; GTA→GAA on the nucleotide level) was responsible for the C179 nonreactivity of the variant.

(e) In order to specify the amino acid sequence around the 318-position of HA1 and the amino acid sequence around the 52-position of HA2 of the HA molecule of each of A/PR/8/34, A/Bangkok/10/83, A/Yamagata/120/86 and A/Osaka/930/88 of the H1N1 subtype, A/Okuda/57, A/Adachi/2/57, A/Kumamoto/1/65 and A/Kaizuka/2/65 of the H2N2 type and A2/Aichi/2/68, A/Fukuoka/C29/85, A/Sichuan/2/87, A/Ibaraki/1/90 and A/Suita/1/90 of the H3N2 subtype, a part of each HA gene was sequenced.

In the case of the strains of the H1N1 subtype, cDNA of the RNA genome of each virus was synthesized in accordance with the method as described in the above Example 4-(3)-(b) and this cDNA was amplified by PCR with the use of the primers 9 and 13. By using the DNA fragment thus obtained as a template, the base sequence was determined by the dideoxy method with the use of a thermal cycler and the primers 11 and 12.

In the case of the strains of the H2N2 subtype, CDNA of the RNA genome of each virus was synthesized in accordance with the method as described in the above Example 4-(3)-(b) and this CDNA was amplified by PCR with the use of the primers 17 and 21. By using the DNA fragment thus obtained as a template, the base sequence was determined similarly by the dideoxy method with the use of the primers 19 and 20.

In the case of the strains of the H3N2 subtype, CDNA of the RNA genome of each virus was synthesized in accordance with the method as described in the above Example 4-(3)-(b) and this cDNA was amplified by PCR with the use of the primers 24 and 26. By using the DNA fragment thus obtained as a template, the base sequence was determined similarly by the dideoxy method with the use of the primers 25 and 26.

In the H1N1 and H2N2 subtypes, the TGLRN polypeptide sequence at the 318- to 322-positions in the HA1 region (A region) represented by the SEQ ID No. 1 in the sequence listing and a the GITNKVNSVIEK polypeptide sequence at the 47- to 58-positions in the HA2 region (B region) represented by the SEQ ID No. 2 in the sequence listing are conserved. In the H3N2 subtype, on the other hand, the TGMRN polypeptide sequence at the 318- to 322-position in the HA1 region (A' region) represented by the SEQ ID No. 3 in the sequence listing and the QINGKLNR(L/V)IEK polypeptide sequence at the 47- to 58-positions in the HA2 region (B' region) represented by the SEQ ID No. 4 in the sequence listing are conserved. The A region differs from the A' region by one amino acid, while the B region differs from the B' region by 5 or 6 amino acid residues. The differences among these regions are responsible for the difference in the antigen recognition of the antibody. Thus the antibody could not react with the H3N2 subtype in the serological and fusion inhibition tests.

As FIG. 1 shows, the TGLRN polypeptide sequence of the A region represented by the SEQ ID No. 1 in the sequence listing and the GITNKVNSVIEK polypeptide sequence of the B region represented by the SEQ ID No. 2 in the sequence listing are close to each other at the center of the stem region of the HA molecule. C179 recognizes both of these sequences and thus this site corresponds to the epitope of C179. C179 binds to the stem region of the HA molecule and thus inhibits the membrane fusion action of the HA molecule and neutralizes the virus.

H1N1 subtype: The sequence of the base Nos. 1017 to 1031 of the HA gene of the A/Suita/1/89 represented by the SEQ ID No. 27 in the sequence listing codes for the A region, while the sequence of the base Nos. 1191 to 1226 thereof codes for the B region. The SEQ ID No. 29 in the sequence listing shows a part of the HA gene of A/PR/8/34, wherein the sequence of the base Nos. 76 to 90 codes for the A region while the sequence of the base Nos. 250 to 285 codes for the B region. The SEQ ID No. 30 in the sequence listing shows a part of the HA gene of A/Bangkok/10/83, wherein the sequence of the base Nos. 76 to 90 codes for the A region while the sequence of the base Nos. 250 to 285 codes for the B region. The SEQ ID No. 31 in the sequence listing shows a part of the HA gene of A/Yamagata/120/86 wherein the sequence of the base Nos. 76 to 90 codes for the A region while the sequence of the base Nos. 250 to 285 codes for the B region. The SEQ ID No. 32 in the sequence listing shows a part of the HA gene of A/Osaka/930/88 wherein the sequence of the base Nos. 76 to 90 codes for the A region while the sequence of the base Nos. 250 to 285 codes for the B region.

H2N2 subtype: The sequence of the base Nos. 1007 to 1021 of the HA gene of the A/Izumi/5/65 represented by the SEQ ID No. 28 in the sequence listing codes for the A region, while the sequence of the base Nos. 1181 to 1216 thereof codes for the B region. The SEQ ID No. 33 in the sequence listing shows a part of the HA gene of A/Okuda/57, wherein the sequence of the base Nos. 94 to 108 codes for the A region while the sequence of the base Nos. 268 to 303 codes for the B region. The SEQ ID No. 34 in the sequence listing shows a part of the HA gene of A/Adachi/2/57, wherein the sequence of the base Nos. 103 to 117 codes for the A region while the sequence of the base Nos. 277 to 312 codes for the B region. The SEQ ID No. 35 in the sequence listing shows a part of the HA gene of A/Kumamoto/1/65, wherein the sequence of the base Nos. 104 to 118 codes for the A region while the sequence of the base Nos. 278 to 313 codes for the B region. The SEQ ID No. 36 in the sequence listing shows a part of the HA gene of A/Kaizuka/2/65, wherein the sequence of the base Nos. 88 to 102 codes for the A region while the sequence of the base Nos. 262 to 297 codes for the B region.

H3N2 subtype: The SEQ ID Nos. 37, 38, 39, 40 and 41 in the sequence listing respectively show a part of HA genes of A2/Aichi/2/68, A/Fukuoka/C29/85, A/Sichuan/2/87, A/Ibaraki/ 1/90 and A/Suita/1/90. In each case, the sequence of the base Nos. 84 to 98 codes for the A' region while the sequence of the base Nos. 258 to 293 codes for the B' region.

Figure 2:
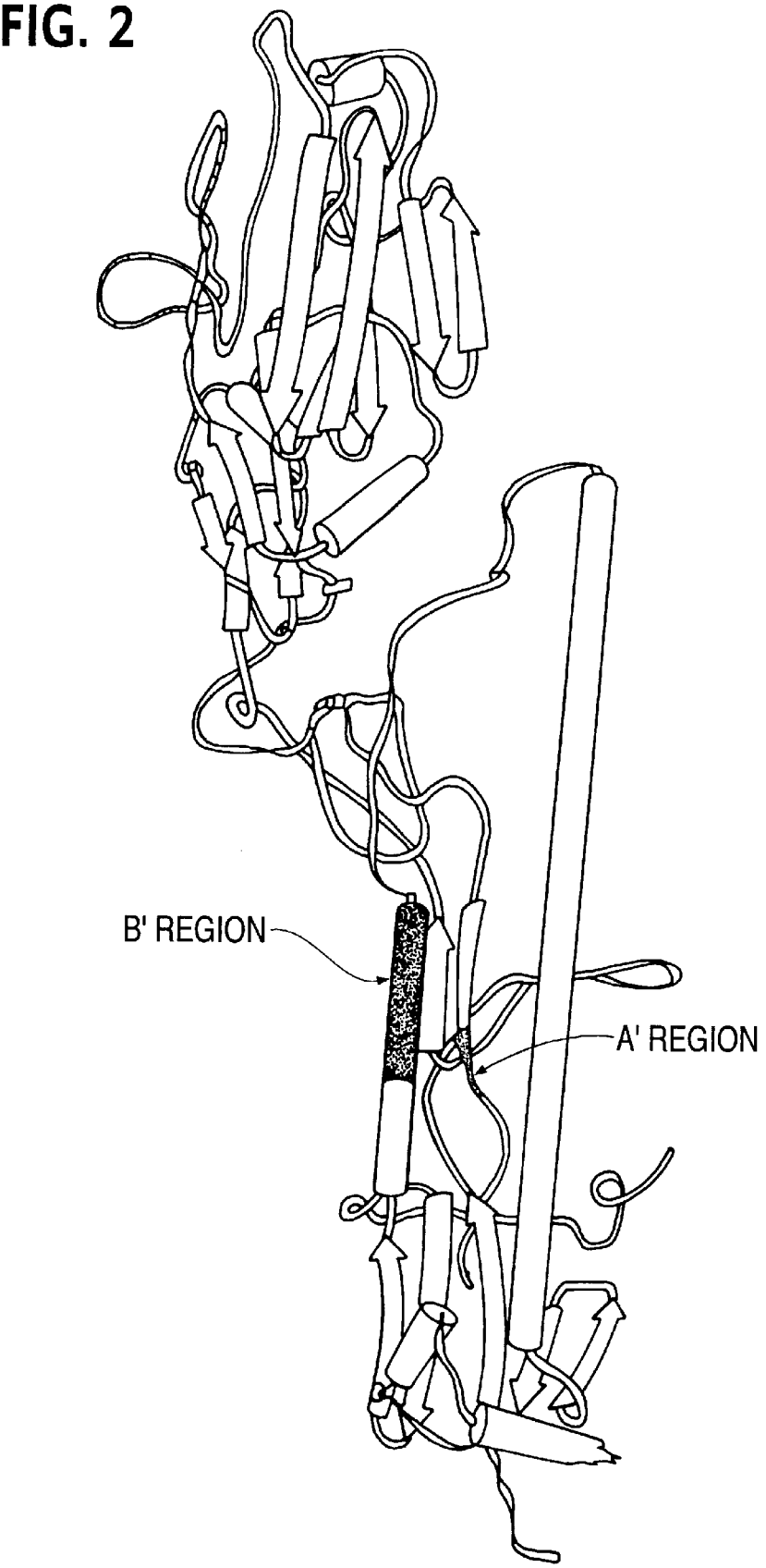
FIG. 2 is a schematic view of the tertiary structure of a HA molecule and shows the position of common conserved regions in HA molecules of H3N2 subtype.

As FIG. 2 shows, the TGMRN polypeptide sequence of the A' region represented by the SEQ ID No. 3 in the sequence listing and the QINGKLNR(L/V)IEK polypeptide sequence of the B' region represented by the SEQ ID No. 4 in the sequence listing are close to each other at the center of the stem region of the HA molecule.

EXAMPLE 5

Preventive Effect on Influenza Virus:

In order to examine the preventive effect of C179, an influenza virus infection test was carried out by using mice. One ml/animal of a C179 solution (1 mg/ml in PBS) was intraperitoneally administered to 10 Balb/c mice. After 1 day, 25 μl of a 1000-fold dilution of A1/FM/1/47 (4000 HAU) of the H1N1 subtype was intranasally administered. As a control, 12 mice were inoculated with the virus alone.

Figure 3:
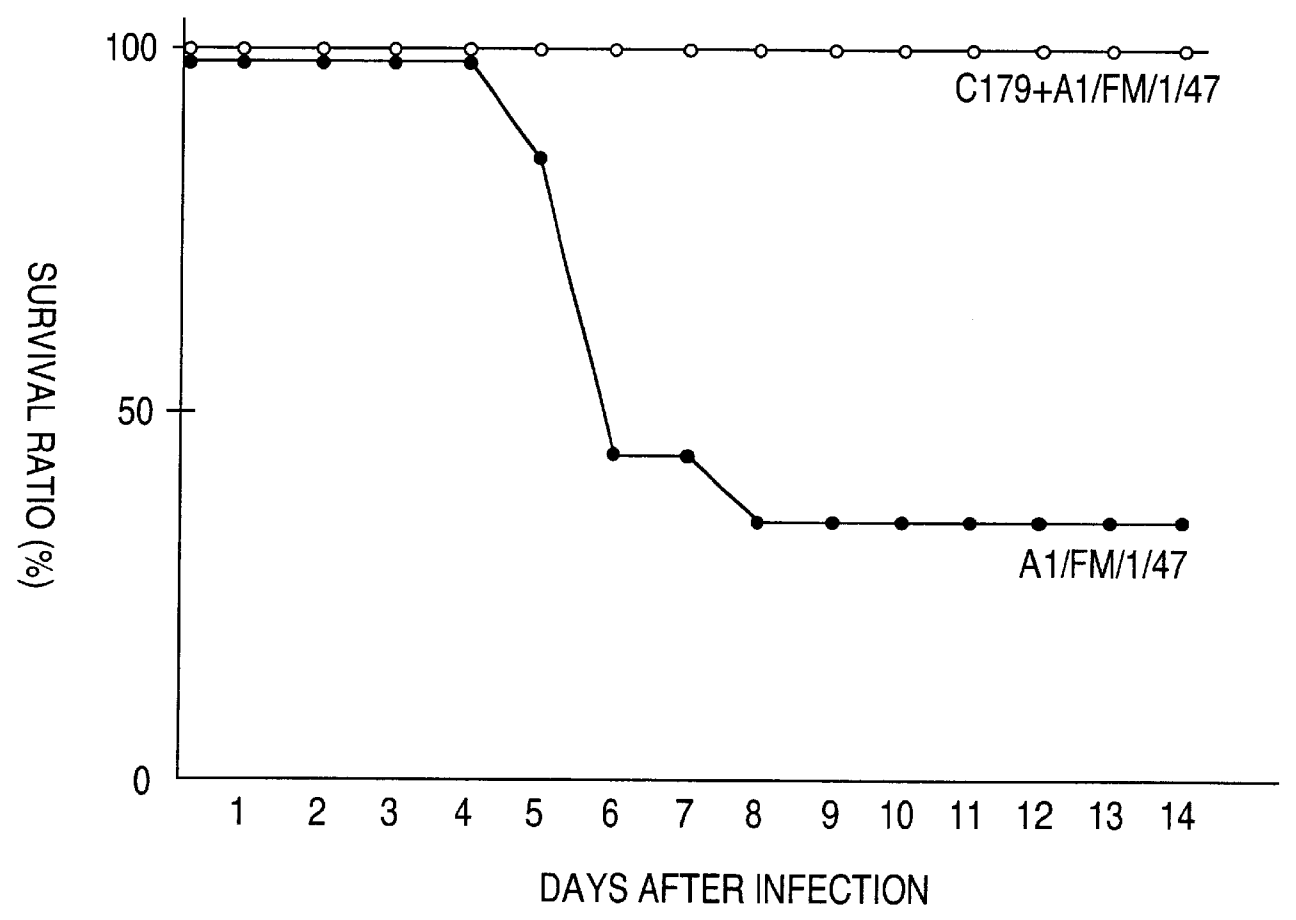

As FIG. 3 shows, 8 mice in the control group died (two mice after 5 days, five after 6 days and one after 8 days). Other surviving mice in this group were extremely weakened. In contrast, the mice administered with C179 showed no abnormality and all remained healthy even after 14 days.

FIG. 3 is a graph showing the survival ratios of the C179-administered group and the control group wherein the ordinate indicates the survival ratio while the abscissa indicates the time (days) after the infection with the virus.

REFERENCE 1

1. Preparation of Viruses:

A strain of H5N3 subtype used was A/whistling swan/ Shimane/476/83. A strain of H6N6 subtype used was A/whistling swan/Shimane/37/80. A strain of H7N7 subtype used was A/turfted duck/Shimane/124R/80. A strain of H8N4 subtype used was A/turky/Ontario/6118/68. A strain of H10N7 subtype used was A/chicken/Germany"N"/49. Each strain is a stock of the Research Institute for Microbial Diseases. A/chicken/ Germany"N"/49 has the amino acid sequences represented respectively by SEQ ID No. 3 and SEQ ID No. 4 in the HA molecule, but other strain lack these sequences.

Each strain was inoculated into the allantoic cavity of an embryonated hen egg aged 11 days, incubated at 34° C. for 4 days and then harvested.

2. Preparation of Monoclonal Antibodies:

(1) Balb/c mice were immunized with two doses of A2/Aichi/57 strain (320 HAU) prepared in the above Example 1, which had been suspended in Freund's complete adjuvant before use, via intraperitoneal injection one month apart. One month thereafter, the mice were boosted by intraperitoneally injecting a suspension of the same antigen (320 HAU) in PBS. Three days thereafter, the spleen of each animal was taken out and thus spleen cells were prepared.

Mouse myeloma cells were prepared by incubating p3x63Ag8 cells in a DME medium containing 10% of fetal bovine serum for 2 days after passage and then washing with physiological saline before cell fusion. The spleen cells were mixed with the myeloma cells at a ratio by cell count of 1:5. After centrifuging and removing the supernatant, the precipitated cell clusters were thoroughly loosened and then added to 1 ml of a mixture [polyethylene glycol 4000 (2 g), MEM (2 ml), and dimethyl sulfoxide] under stirring. After maintaining at 37° C. for 5 minutes, MEM was slowly added thereto so as to adjust the total amount to 10 ml. After the mixture was centrifuged, the supernatant was removed and the cell clusters were gently loosened. 30 ml of a normal medium (PRMI-1640 containing 10% of fetal bovine serum) was added thereto and the cells were slowly suspended with the use of a measuring pipet.

The suspension was pipetted into a 96-well incubation plate and incubated in an incubator containing 5% of $CO_2$ at 37° C. for 24 hours. Then HAT medium was added thereto and the incubation was continued for 10 to 14 days. Subsequently, a part of the culture supernatant was sampled and subjected to hybridoma screening.

(2) To obtain a monoclonal antibody undergoing a cross reaction between H3N2 subtype and H10N7 subtype, the above-mentioned culture supernatant, which had not been diluted, was used as a primary antibody and a staining test on MDCK cells infected with the three subtypes (H3N2, H10N7 and H1N1) was effected. The staining test was carried out in accordance with the above-mentioned method described in example 2-(2). Specifically, the MDCK cells infected with the influenza virus subtype strains (H3N2: A2/Aichi/2/68, H10N7: A/chicken/Germany"N"/49, H1N1: A/PR/8/34) were rinsed with PBS (pH 7.4) on 96-well microtiter plates (Falcon 3072) and fixed with absolute ethanol at room temperature for 10 minutes. Then these cells were continuously treated with 4 antibodies [the above-mentioned culture supernatant containing the monoclonal antibody, rabbit anti-mouse immunoglobulin G serum diluted 1000-fold, goat anti-rabbit immunoglobulin G serum diluted 500-fold, and peroxidase-rabbit anti-peroxidase complex diluted 1000-fold, each for 40 minutes, and the cells thus treated were washed with PBS. Finally, the peroxidase reaction was effected by the method of Graham and Karnovsky with the use of 0.01% $H_2O_2$ and 0.3 mg/ml of 3,3'-diaminobenzidine tetrahydrochloride in PBS. The stained cells were observed under an ordinary light microscope to sort antibodies recognizing respectively the H3N2 subtype-infected MDCK cells and the H10N7 subtype-infected MDCK cells. Next, the cells in the wells where the production of these antibodies had been confirmed were taken out and treated by the limiting dilution thrice to thereby clone the target cells. The hybridoma strain thus cloned was named Hybridoma AI3C, while the monoclonal antibody produced thereby was named monoclonal antibody AI3C.

The tradename of this monoclonal antibody is monoclonal antibody F49 (manufactured by Takara Shuzo Co., Ltd.)

The Hybridoma AI3C was deposited on Nov. 11, 1992 at Fermentation Research Institute, Agency of Industrial Science and Technology (1–3, Higashi 1 chome Tsukuba-shi Ibaraki-ken 305, JAPAN), under accession number FERM P-13275, and on Dec. 27, 1993 this deposit was converted to deposit at National Institute of Bioscience and Human-Technology, Agency of Industrial Science and Technology in accordance with the Budapest Treaty under the accession number FERM BP-4516.

(3) $5\times10^6$/animal of the above-mentioned hybridomas were intraperitoneally administered to Balb/c mice treated with pristane. Ten to 21 days thereafter, the ascites of a mouse having ascites cancer thus induced was sampled and centrifuged at 3000 rpm for 5 minutes to thereby remove solid components and give an ascites fluid. This fluid contained about 5 mg/ml of the monoclonal antibody AI3C (hereinafter referred to simply as AI3C). AI3C was purified with Protein A-Sepharose 4B.

3. Properties of Monoclonal Antibody:

(1) A 100-fold dilution of the ascites fluid as described in the Reference 1-2-(3) was diluted stepwise and the staining test as described in the above Example 2-(2) was effected to examine the antigen recognizing characteristics of AI3C. The H1N1 subtype strains used included A/PR/8/34, A/Bangkok/10/83, A/Yamagata/120/86, A/Osaka/930/88, A/Suita/1/89 and A1/FM/1/47. The H2N2 subtype strains used included A/Okuda/57, A/Adachi/2/57, A/Kumamoto/1/65, A/Kaizuka/2/65 and A/Izumi/5/65. The H3N2 subtype strains used included A/Aichi/2/68, A/Fukuoka/C29/85, A/Sichuan/2/87, A/Ibaraki/1/90, and A/Kitakyushu/159/93. A/Suita/1/90. Further, B/Nagasaki/1/87 was used as an influenza B virus strain and the strains described in the Reference 1-1 were used.

AI3C recognized all of the H3N2 subtype and A/chicken/Germany"N"/49 but did not recognize the H1N1 subtype strains, H2N2 subtype strains, the influenza virus B strain, and other subtype strains.

(2) The HI activity of the antibody was examined by the following method. The antibody (32-fold dilution) which had been treated with RDE in the same manner as the one described in the above Example 3-(2) was diluted stepwise and mixed with each virus strains (16 HAU) as described in the above Reference 1-1 and 1-3-(1) to effect a reaction at room temperature for 30 minutes. After adding avian erythrocytes and well mixing, the effect of the antibody on the hemagglutination activity of each virus strain was examined. It was found that the hemagglutination activity of none of the virus strains was affected by AI3C.

4. Determination of Epitope:

It was determined by immunoprecipitation that the protein recognized by AI3C was HA molecules. Specifically, MDCK cells were infected with an H3N2 subtype strain A2/Aichi/2/68 via adsorption for 30 minutes and then incubated in MEM wherein methionine was replaced with 10 $\mu$Ci of [$^{35}$S]methionine for 24 hours to thereby label the infected cells. Next, the cells were harvested and suspended again in an RIPA buffer solution [50 mM Tris (pH 7.4), 150 mM NaCl, 1 mM EDTA, 1% Nonidet P-40, 1% deoxycholate and 0.1% SDS]. After removing the insoluble matters by centrifuging, a supernatant was obtained. Then this supernatant was mixed with AI3C and kept at 4° C. for 1 hour. Protein A-Sepharose CL4B beads were added thereto and kept at room temperature for 2 hours to thereby allow the beads to adsorb the immunoprecipitate. These beads were collected, washed 5 times with an RIPA buffer solution and boiled to thereby liberate the protein binding to AI3C. Then this protein was electrophoresed on an SDS-12.5% polyacrylamide gel. The gel was fixed, soaked in a 1 M sodium salicylate solution and dried to effect autoradiography. The labeled protein binding to AI3C was thus identified with the HA molecule of A2/Aichi/2/68 based on its electrophoretic pattern. The H1N1 subtype strains, H2N2 subtype strains, other H3N2 subtype strains, and strains described in above Reference 1-1 were also tested in the same manner. It was found that AI3C underwent immunoprecipitation specifically together with all of the H3N2 subtype strains and A/chicken/Germany"N"/49 but showed no avidity on the HA molecule of the other subtypes.

EXAMPLE 6

Construction of the Stem Region Polypeptide:

(1) Synthesis of primers: Primers 27 to 30 were synthesized with a DNA synthesizer, freed from the protective group and purified by ion exchange HPLC (TSK Gel, DEAE-2SW Column). After desalting with a reverse phase cartridge column (SEP-PACK C18), about 50 $\mu$g portions of DNAs were obtained.

Primers 27 and 28 have the sequences of 5'-terminal of HA gene of H2N2 subtype, and primers 29 and 30 have the complimentary sequences of 3'-terminal of one. The base sequences of primers 27 to 30 are represented respectively by the SEQ ID Nos. 42 to 45.

(2) MDCK cells infected with A/Okuda/57 were harvested and guanidine isothiocyanate was added thereto. The mixture was repeatedly sucked and discharged 5 times with the use of a syringe to thereby dissolve the cells. After the completion of the dissolution, the cell extract was layered over a cesium chloride solution and ultracentrifuged. The precipitate on the bottom of a centrifuging tube was dissolved in a buffer solution, treated with phenol and chloroform, and precipitated from ethanol. The RNA thus recovered was used as a sample of virus genome RNA. Next, cDNAs were synthesized by using the primer 5 and the cDNAs thus synthesized were amplified by the PCR method with the use of the primers 27 and 29. The cDNAs thus amplified were next separated by agarose gel electrophoresis to thereby elute a cDNA band of 1.8 kbp corresponding to the HA gene. This cDNA was further amplified by the PCR method with the use of the primers 28 and 30. To the second amplified fragment of 1.8 kbp was added 20% (w/v) of polyethylene glycol in 60% (v/v) of a 2.5 M NaCl solution. After centrifuging, a purified precipitate fraction was obtained.

(3) The base sequence of HA gene for A/Okuda/57 was analyzed by the methods described in example 4-(3)-(b),(d). The base and amino acid sequences of it are represented by the SEQ ID No. 46. In the sequence represented by the SEQ ID No. 46, the sequence of the base Nos. 1 to 5 originates in primer 28, the sequence of base Nos. 6 to 48 is the non-coding regions, the sequence of base Nos. 49 to 93 is the coding region for signal polypeptide, the sequence of base Nos. 94 to 231 is the coding region for the stem region of N-terminal domain of HA molecule, the sequence of base Nos. 232 to 873 is the coding region for the globular head region of HA molecule, the sequence of base Nos. 874 to 1734 is the coding region for the stem region of C-terminal domain of HA molecule, the sequence of base Nos. 1735 to 1775 is the non coding region, and the sequence of base Nos. 1776 to 1783 originates in primer 30.

(4) Construction of the plasmids.

(a) The terminals of the 1.8 kbp DNA fragment prepared in example 6-(2) was treated by T4 DNA polymerase for creating blunt ends. It was ligated with a plasmid pHSG299 (manufactured by Takara Shuzo Co. Ltd.,) digested with restriction enzyme SmaI by T4 DNA ligase. *E. coli* JM109 was transformed with the ligated sample and some kanamycin resistant transformants were gotten. A plasmid pH2-299 which containing HA gene was prepared from one of these transformants. *E. coli* JM109 harboring the plasmid pH2-299 was named *Escherichia coli* JM109/pH2-299 and has been deposited on Feb. 16, 1993 with National Institute of Bioscience and Human-Technology, Agency of Industrial Science and Technology under the accession number FERM P-13431.

(b) A plasmid pEF-BOS/neoA, which is a shuttle vector for mammalian cell and *E. coli*, was constructed by A 2.6 kbp BamBI DNA fragment from pMAMneo-s (manufactured by Clontech Lab. Inc.) inserting into AatII site of a plasmid pEF-BOS [Nucleic Acids Research, 18, 5322 (1990)].

Then the 1.8 kbp NheI DNA fragment from pH2-299 and pEF-BOS/neoA digested with restriction enzyme XbaI were ligated by T4 DNA ligase. *E. coli* JM109 was transformed with the ligated sample and some ampicillin resistant transformants was gotten. A plasmid which containing the HA gene was prepared from one of these transformants and named pEBNaH2. *E. coli* JM109 harboring the plasmid pEBNaH2 was named *Escherichia coli* JM109/pEBNaH2.

(c) Primers 31 and 32, represented respectively by the SEQ ID Nos. 47 and 48, were synthesized by using DNA synthesizer and purified with HPLC (TSK gel, DEAE-2SW column) and Sep-pak C18. The primer 31 has a complementary sequence to the sequence of the base Nos. 207 to 231 in the SEQ ID No. 46. The primer 32 has a sequence to sequence of the base Nos. 874 to 899 (but base No. 876 is changed A to C) in the SEQ ID No. 46. The amplification of 3.8 kbp DNA fragment which is lacking the region coding for the globular head region of HA molecule from pH2-299 was tried by PCR method using these primers.

The PCR reaction was performed with 50 pmol of primer 31, 50 pmol primer 32 and pH2-299 prepared from *Escherichia coli* JM109/pH2-299 (FFRM P-13431) as template. The reaction was performed for 25 cycles with each cycle consisting of 1 minute at 90° C., 2 minutes at 55° C., 3 minutes at 72° C. And a 3.8 kbp fragment was amplified. Then this fragment was phosphorylated by T4 kinase, treated with T4 DNA ploymerase for creating blunt ends, and ligated by T4 DNA ligase to make plasmid. *E. coli* JM109 was transformed with the ligeted palsmid and some kanamycin resistant transformante were gotten. A plasmid prepared from one of these transformante was named p299H2Sn-c, that was containing the HA gene which was lacking the region coding for the globular head region (the base Nos. 232 to 873 in the SEQ ID No. 46) and having the coding region for the stem region of N-terminal domain of HA molecule and C terminal domain of HA molecule joined. A 1.1 kbp DNA fragment containing the gene coding for the stem region polypeptide was prepared from p299H2Sn-c by digestion of restriction enzyme NheI. The base sequence for this fragment and the amino acid sequence of the stem region polypeptide translated from this DNA fragment were represented respectively by the SEQ ID No. 49 and SEQ ID No. 50 in the sequence listing. A plasmid that had the gene coding for the stem region polypeptide was constructed by ligation of the 1.1 kbp NheI fragment from p299H2Sn-c and pEF-BOS/neoA digested with XbaI with T4 DNA ligase. *E. coli* JM109 was transformed with the ligated sample and some ampicillin resistant transformats were gotten. A plasmid containing the gene coding for the stem region polypeptide was named pENH2dH01, and *E. coli* JM109 harboring the plasmid pENH2dH01 was named *Escherichia coli* JM109/pENH2dH01 and has been deposited on Feb. 16, 1993 with National Institute of Bioscience and Human-Technology, Agency of Industrial Science and Technology in accordance with the Budapest Treaty under the accession number FERM BP-4190.

(5) Expression of polypeptides:

The plasmid pENH2dH01 containing the gene coding for the stem region polypeptide was prepared from *Escherichia coli* JM109/pENH2dH01 and the plasmid pEBNaH2 containing HA gene was prepared from *Escherichia coli* JM109/pEBNaH2.

Trypsin treated CV-1 cells ($5\times10^6$ cells) were washed with 20 ml 10% FCS-MEM in one time, and 20 ml PBS in two times, and suspended in 1 ml PBS. The 0.8 ml part of it and the plasmid pENH2dH01 (30 mg) were put into a cuvette for an electroporation device (GENE-PULSER™) (manufactured by BioRad), and the cuvette was set into GENEPULSER™. The cells and plasmid were treated in 250V, 960 mFD by GENEPULSER™. After the sample was put at 0° C. for 10 minutes, the cells were suspended in 30 ml 10% FCS-MEM and 5 ml each was cultured in a dish (6 cm) for two days.

The CV-1 cells transformed with the plasmid pENH2dH01 were washed with PBS (pH7.4) and fixed with absolute ethanol at room temperature for 10 minutes. Focus staining was done by successive treatment of the cells with C179 (1:1000), rabbit anti-mouse immunoglobulin G serum (1:1000), goat anti-rabbit immnuoglobulin G serum (1:500), and peroxidase-rabbit anti-peroxidase (PAP) complex (1:1000). Each treatment was 40 minutes long and was followed by a washing with PBS. The peroxide reaction was developed for about 5 minutes by the method of Graham and Karnousky in which 0.01% $H_2O_2$ and 0.3 mg of 3,3'-diaminobenzidene tetrahydrochloride per ml in PBS were used.

The CV-1 cells transformed with pENH2dH01 were stained by immunostaining with C179. So the expressed the stem region polypeptide had normal structure of high dimension for the stem region of HA molecule in spite of lacking of the globular head region of HA molecule. As this polypeptide is lacking the globular head region of HA molecule which is apt to become antigenic determinants and to arise antigenic mutation, it will be able to become the antigen that induce the antibodys recognizing the stem region of HA molecule and counteracting both H1N1 subtype and H2N2 subtype influenza viruses, like C179 type antibody. So this stem region polypeptide is useful for the influenza vaccine.

Similarly, the CV-1 cells transformed with pEBNaH2 were stained by immunostaining method with C179, so the expressed polypeptide also had normal structure of high dimension for the stem region of HA molecule.

EXAMPLE 7

Construction of the Stem Region Polypeptide:

(1) Synthesis of primers: Primers 33 to 35 were synthesized with a DNA synthesizer, freed from the protective group and purified by ion exchange HPLC (TSK Gel, DEAE-2SW Column). After desalting with Sep-pack C18, about 50 μg portions of DNAs were obtained.

Primers 33 has the sequences of 5'-terminal of HA gene of H3N2 subtype, and primers 34 and 35 have the complimentary sequences of 3'-terminal of one. The nucleotide sequences of primers 33 to 35 are represented respectively by the SEQ ID Nos. 51 to 53.

(2) MDCK cells infected with A2/Aichi/2/68 were harvested and guanidine isothiocyanate was added thereto. The mixture was repeatedly sucked and discharged 5 times with the use of a syringe to thereby dissolve the cells. After the completion of the dissolution, the cell extract was layered over a cesium chloride solution and ultracentrifuged. The precipitate on the bottom of a centrifuging tube was dissolved in a buffer solution, treated with phenol and chloroform, and precipitated from ethanol. The RNA thus recovered was used as a sample of virus genome RNA. Next, CDNAs were synthesized by using the primer 5 and the cDNAs thus synthesized were amplified by the PCR method with the use of the primers 33 and 34. The cDNAs thus amplified were next separated by agarose gel electrophoresis to thereby elute a cDNA band of 1.8 kbp corresponding to the HA gene. This CDNA was further amplified by the PCR method with the use of the primers 33 and 35. To the second amplified fragment of 1.8 kbp was added 20% (w/v) of polyethylene glycol in 60% (v/v) of a 2.5 M NaCl solution. After centrifuging, a purified precipitate fraction was obtained.

(3) The base sequence of HA gene for A2/Aichi/2/68 was analyzed by the methods described in example 4-(3)-(b),(d). The base and amino acid sequences of it are represented by the SEQ ID No. 54 in the sequence listing. In the sequence No. 54, the sequence of the base Nos. 1 to 8 originates in primer 33, the sequence of base Nos. 9 to 36 is the non coding regions, the sequence of base Nos. 37 to 84 is the coding region for signal polypeptide, the sequence of base Nos. 85 to 246 is the coding region for the stem region of N-terminal domainof HA molecule, the sequence of base Nos. 247 to 903 is the coding region for the globular head region of HA molecule, the sequence of base Nos. 904 to 1769 is the coding region for the stem region of C-terminal domain of HA molecule, the sequence of base Nos. 1735 to 1769 is the non coding region, and the sequence of base Nos. 1770 to 1777 originates in primer 35.

(4) Construction of the plasmids:

(a) The terminals of the 1.8 kbp DNA fragment prepared in example 7-(3) was treated by T4 DNA polymerase for creating blunt ends. It was ligated with a plasmid pUC118 (manufactured by Takara Shuzo Co. Ltd.,) digested with HincII by T4 DNA ligase. *E. coli* JM109 was transformed with the ligated sample and some ampicillin resistant transformants were gotten. A plasmid which containing HA gene was prepared from one of these transformants and named pU118H3xxn. *E. coli* JM109 harboring the plasmid pU118H3xxn was named *Escherichia coli* JM109/pU118H3xxn and has been deposited on Mar. 30, 1993 with National Institute of Bioscience and Human-Technology, Agency of Industrial Science and Technology under the accession number FERM P-13567.

(b) Primers 36 and 37, represented respectively by the SEQ ID Nos. 55 and 56, were synthesized by using DNA synthesizer and purified with HPLC (TSK gel, DEAE-2SW column) and Sep-pak C18. The primer 36 has a complementary sequence to the sequence of the base Nos. 227 to 246 in the SEQ ID No. 54. The primer 37 has a sequence to sequence of the base Nos. 904 to 923 in the SEQ ID No. 54. The amplification of 4.3 kbp DNA fragment which was lacking the region coding for the globular head region of HA molecule from pU118H3xxn was tried by PCR method using these primers. The PCR reaction was performed with 50 pmol of primer 36, 50 pmol primer 37 and pU118H3xxn prepared from *Escherichia coli* JM109/pU118H3xxn (FFRM P-13567) as template. The reaction was performed for 25 cycles with each cycle consisting of 1 minute at 90° C., 2 minutes at 55° C., 3 minutes at 72° C. And a 4.3 kbp fragment was amplified. Then this fragment was phosphorylated by T4 kinase, treated with T4 DNA ploymerase for creating blunt ends, and ligated by T4 DNA ligase to make plasmid. *E. coli* JM109 was transformed with the ligeted palsmid and some ampicillin resistant transformante were gotten. A plasmid prepared from one of these transformante was named p118H3dH01, that was containing the HA gene which was lacking the region coding for the globular head region (the base Nos. 247 to 903 in the SEQ ID No.54) and having the coding region for the stem region of N-terminal domain of HA molecule and C terminal domain of HA molecule joined. A 1.1 kbp DNA fragment containing the gene coding for the stem region polypeptide was prepared from p118H3dH01 by digestion of NheI and XbaI. The nucleotide sequence for this fragment and the amino acid sequence of the stem region polypeptide translated from this DNA fragment were represented respectively by the SEQ ID No. 57 and SEQ ID No. 58 in the sequence listing. A plasmid that had the gene coding for the stem region polypeptide was constructed by ligation of the 1.1 kbp NheI fragment from p118H3dH01 and pEF-BOS/neoA digested with XbaI with T4 DNA ligase. *E. coli* JM109 was transformed with the ligated sample and some ampicillin resistant transformats were gotten. A plasmid prepared from one of these transfmats was named pENH3dH01 that was containing the gene coding for the stem region polypeptide, and *E. coli* JM109 harboring the plasmid pENH3dH01 was named *Escherichia coli* JM109/pENH3dH01. *Escherichia coli* JM109/pENH3dH01 was deposited on Mar. 30, 1993 at National Institute of Bioscience and Human-Technology, Agency of Industrial Science and Technology under accession number FERM P-13568, and on Dec. 27, 1993 this deposit was converted to deposit at National Institute of Bioscience and Human-Technology, Agency of Industrial Science and Technology in accordance with the Budapest Treaty under the accession number FERM BP-4518.

(5) Expression of the stem region polypeptide:

The plasmid pENH3dHO1 containing the gene coding for the stem region polypeptide was prepared from *Escherichia coli* JM109/pENH3dH01.

Trypsin treated CV-1 cells ($5 \times 10^6$ cells) were washed with 20 ml 10% FCS-MEM in one time, and 20 ml PBS in two times, and suspended in 1 ml PBS. The 0.8 ml part of it and the plasmid pENH3dH01 (30 mg) were put into a cuvette for GENEPULSER™, and the cuvette was set into GENEPULSER™. The cells and plasmid were treated in 250V, 960 mFD by GENEPULSER™. After the sample was put at 0° C. for 10 minutes, the cells were suspended in 30 ml 10% FCS-mEM and 5 ml each was cultured in a dish (6 cm) for two days.

The CV-1 cells transformed with the plasmid pENH3dH01 were washed with PBS (pH7.4) and fixed with absolute ethanol at room temperature for 10 minutes. Focus staining was done by successive treatment of the cells with AI3C (1:1000), rabbit anti-mouse immunoglobulin G serum (1:1000), goat anti-rabbit immnuoglobulin G serum (1:500), and peroxidase-rabbit anti-peroxidase (PAP) complex (1:1000). Each treatment was 40 minutes long and was followed by a washing with PBS. The peroxide reaction was developed for about 5 minutes by the methed of Graham and Karnousky in which 0.01% $H_2O_2$ and 0.3 mg of 3.3-diaminobenzidene tetrahydrochloride per ml in PBS were used.

The CV-1 cells transformed with pENH3dH01 were stained by immunostaining with AI3C. So the expressed the stem region polypeptide peptides had normal structure of high dimension for the stem region of HA molecule of H3N2 subtype in spite of lacking of the globular head region of HA molecule. This polypeptide is lacking the globular head region of HA molecule which is apt to become antigenic determinants and to arise antigenic mutation, it will be able to become the antigen that induce the antibodys recognizing the stem-region of HA molecule of H3N2 subtype influenza viruses, like AI3C type antibody. So this stem region polypeptide is useful for the influenza vaccine.

EXAMPLE 8

Preparation of Antigen Polypeptide:

(1) Preparation of HA Molecules

Viral particles (40 mg) of A/Yamagata/32/89 prepared in Example 1 were suspended in 27 ml of 5 mM Tris-HCl (pH 8.0). After adding 3 ml of 20% NP-40, the mixture was maintained at 370° C. for 30 minutes. Then it was centrifuged and the supernatant was collected and filtered through a 0.8 μm filter unit (Millex PF: manufactured by Millipore). Subsequently the filtrate was loaded on HA molecules were eluted with the same buffer containing 1 M of NaCl.

(2) Treatment of HA Molecule with Proteinase

In an N-ethylmorpholine buffer solution (pH 7.5), the HA molecules (2.6 μg) prepared in the above Example 8-(1) were digested with 4-pmol portions of lysyl endopeptidase (manufactured by wako Pure Chemical Industries, Ltd.), V8 protease (manufactured by Sigma Chemical Co.) and chymotrypsin (manufactured by Boehringer) at 37° C. for 1 hour.

The HA molecules (2.6 μg) prepared in the above Example 8-(1) were denatured by maintaining at 42° C. in the presence of 2 M of urea for 1 hour. Next, these molecules were digested with 4-pmol portions of lysyl endopeptidase, V8 protease, chymotrypsin, subtilisin (manufactured by Boehringer), proteinase K (manufactured by Boehringer), pronase (manufactured by Boehringer) and thermolysin (manufactured by Boehringer) in a 50 mM tris hydrochloride buffer solution (pH 7.6) at 37 C. for 12 hours and then dialyzed against PBS.

A portion of each digestion mixture was collected and the digested fragments were analyzed by the dot-blot method with the use of C179 and SDS polyacrylamide gel electrophoresis.

The dot-blot method was effected in the following manner.

1 μl of the digestion mixture was loaded onto a nitrocellulose filter (manufactured by mSI) and dried. The same procedure was repeated 5 times to thereby load 5 μl of the digestion mixture in total. Then blocking was carried out with the use of Blockace (manufactured by Snow Brand Milk Products Co.). Next, it was reacted with a 500-fold dilution of a C179 solution at room temperature for 1-hour. After washing with a tris hydrochloride buffer solution (pH 7.6) containing 0.02% of Tween 20, washing was further effected with a tris hydrochloride buffer solution (pH 7.6) for 10 minutes thrice.

Then it was reacted with a 500-fold dilution of an alkaline phosphatase-labeled goat anti-mouse immunoglobulin G solution (manufactured by Orgenics, Ltd.) at room temperature for 1 hour and washed in the same manner as the one described above. Finally, the alkaline phosphatase reaction was performed by using a solution of nitro blue tetrazolium 5-bromo-4-chloro-3-indolyl phosphate in carbon/sodium carbonate (pH 9.0) in the presence of 1 mM of $MgCl_2$.

As a result, it was found out that most of the HA molecules remained undigested when treated with each of these proteases in the absence of urea. The HA molecules, which had been denatured with urea, employed as a substrate were not digested with v8 protease, thermolysin and pronase. When lysyl endopeptidase, chymotrypsin and subtilisin were used, the digestion proceeded excessively and the antigenicity for C179 completely disappeared. When proteinase K was used, on the other hand, it was confirmed that the HA molecules were digested and polypeptide fragments having an avidity for C179 were formed.

(3) Preparation of Stem Region Polypeptide

To the HA molecules (250 μg/1400 μl) prepared in Example 8-(1) were successively added 100 μl of 1 M Tris-HCl (pH 7.6) and 500 μl of 8 M urea and the resulting mixture was maintained at 42° C. for 1 hour. To this solution was added 2000 μl of an immobilized Proteinase K gel and maintained at 37° C. for 7 hours under shaking. After centrifuging, the reaction mixture thus obtained was dialyzed against PBS for 12 hours and thus the stem region polypeptide was obtained. The immobilized Proteinase K gel was prepared in the following manner. 4 mg of Proteinase K (manufactured by Boehringer) was dissolved in 1 ml of $H_2O$ and the pH value of the solution was adjusted to 5.0 with 0.1 N HCl. After adding 1 ml of ECH-Sepharose (manufactured by Pharmacia) and 1 ml of 0.2 M EDC (pH 5.0) thereto, the mixture was maintained at 4° C. for 24 hours. This gel was washed with 10 ml portions of PBS thrice to thereby give the immobilized Proteinase K gel.

(4) Properties of Stem Region Polypeptide

By using the stem region polypeptide of Example 8-(3) as a test sample, the antigenicity for C179 was examined by the ELISA method. Namely, a diluted solution of the stem region polypeptide was added to a microtiter plate (Maxi Sorp; manufactured by Nunc) and immobilized at 37° C. for 90 minutes. Then blocking was effected by using Block Ace (manufactured by Snow Brand Milk Products). Then these cells were continuously reacted with 2 antibodies [10 mg/ml C179 solution diluted 200-fold, and peroxidase-labeled goat anti-mouse immunoglobulin G solution (manufactured by Cappel) diluted 500-fold] each for 90 minutes and the cells thus treated were washed with PBS. Finally, the peroxidase reaction was effected by using 0.03% $H_2O2$ and 1 mg/ml of o-phenylenediamine dihydrochloride in citric acid/phosphoric acid (pH 5.2). The amount of the antigen was calculated from the absorbance of the reaction mixture at 492 nm. As a standard, HA molecules described in Example 8-(1) were used. As the result of the ELISA method, it has been proved that this stem region polypeptide has an antigenicity comparable to that of HA molecules. The hemagglutination activity (HA value) of the stem region polypeptide was determined in the following manner. On a U-shaped 96-well microtiter plates (Falcon 3911: manufactured by Becton Dickinson Labware), the sample solution was diluted with PBS in two steps. Then the same amount of a 0.5% avian erythrocyte suspension was added thereto and the mixture was stirred well. After reacting at room temperature for 1 hour, agglutination of the erythrocytes was observed. The highest dilution ratio showing agglutination was taken as the HA value.

The HA value of the stem region polypeptide was less than 1/1000 of the HA value of HA molecules.

Thus it has been clarified that the stem region polypeptide prepared by the treatment with the protease has an antigenicity comparable to that of HA molecules and the hemagglutination activity originating in the globular head region has substantially disappeared.

This polypeptide can easily serve as an antigen determinant and the globular head region, which is liable to undergo antigen mutation, has been digested therefrom. Thus it is usable as a vaccine capable of specifically recognizing the stem region of the H1N1 and H2N2 subtypes and inducing an antibody neutralizing the virus.

EXAMPLE 9

Preparation of Antigen Polypeptide:

(1) Preparation of HA Molecules

Viral particles (40 mg) of A/Kitakyushu/159/93 prepared in Example 1 were suspended in 27 ml of 5mM Tris-HCl (pH 8.0). After adding 3 ml of 20% NP-40, the mixture was maintained at 37° C. for 30 minutes. Then it was centrifuged and the supernatant was collected and filtered through a 0.8 μm filter unit (Millex PF: manufactured by Millipore). Subsequently the filtrate was loaded on an ion exchange membrane (memsep DEAE: manufactured by millipore) and washed with the same buffer. Further, HA molecules were eluted with the same buffer containing 1 M of NaCl.

(2) Treatment of HA Molecule with Proteinase

In an N-ethylmorpholine buffer solution (pH 7.5), the HA molecules (2.6 μg) prepared in the above Example 9-(1) were digested with 4-pmol portions of lysyl endopeptidase (manufactured by Wako Pure Chemical Industries, Ltd.), V8 protease (manufactured by Sigma Chemical Co.) and chymotrypsin (manufactured by Boehringer) at 37° C. for 1 hour.

The HA molecules (2.6 μg) prepared in the above Example 9-(1) were denatured by maintaining at 42° C. in the presence of 2 M of urea for 1 hour. Next, these molecules were digested with 4-pmol portions of lysyl endopeptidase, V8 protease, chymotrypsin, subtilisin (manufactured by Boehringer), proteinase K (manufactured by Boehringer), pronase (manufactured by Boehringer) and thermolysin (manufactured by Boehringer) in a 50 mM tris hydrochloride buffer solution (pH 7.6) at 37° C. for 12 hours and then dialyzed against PBS.

A portion of each digestion mixture was collected and the digested fragments were analyzed by the dot-blot method with the use of AI3C and SDS polyacrylamide gel electrophoresis.

As a result, it was found out that most of the HA molecules remained undigested when treated with each of these proteases in the absence of urea. The HA molecules, which had been denatured with urea, employed as a substrate were not digested with V8 protease, thermolysin and pronase. When lysyl endopeptidase, chymotrypsin and subtilisin were used, the digestion proceeded excessively and the antigenicity for AI3C completely disappeared. When proteinase K was used, on the other hand, it was confirmed that the HA molecules were digested and polypeptide fragments having an avidity for AI3C were formed.

(3) Preparation of Stem Region Polypeptide

To the FHA molecules (250 μg/1400 μl) prepared in Example 9-(1) were successively added 100 μl of 1 M Tris-HCl (pH 7.6) and 500 μl of 8 M urea and the resulting mixture was maintained at 42° C. for 1 hour. To this solution was added 2000 μl of an immobilized Proteinase K gel and maintained at 37° C. for 7 hours under shaking. After centrifuging, the reaction mixture thus obtained was dialyzed against PBS for 12 hours and thus the stem region polypeptide was obtained.

(4) Properties of Stem Region Polypeptide

By using the stem region polypeptide of Example 9-(3) as a test sample, the antigenicity for AI3C was examined by the ELISA method. Namely, a diluted solution of the stem region polypeptide was added to a microtiter plate (Maxi Sorp; manufactured by Nunc) and immobilized at 37° C. for 90 minutes. Then blocking was effected by using Block Ace (manufactured by Snow Brand Milk Products). Then these cells were continuously reacted with 2 antibodies [10 mg/ml AI3C solution diluted 200-fold, and peroxidase-labeled goat anti-mouse immunoglobulin G solution (manufactured by Cappel) diluted 500-fold] each for 90 minutes and the cells thus treated were washed with PBS. Finally, the peroxidase reaction was effected by using 0.03% H2O2 and 1 mg/ml of o-phenylenediamine dihydrochloride in citric acid/phosphoric acid (pH 5.2). The amount of the antigen was calculated from the absorbance of the reaction mixture at 492 nm. As a standard, HA molecules described in Example 9-(1) were used. As the result of the ELISA method, it has been proved that this stem region polypeptide has an antigenicity comparable to that of HA molecules. The hemagglutination activity (HA value) of the stem region polypeptide was determined in the following manner. On a U-shaped 96-well microtiter plates (Falcon 3911: manufactured by Becton Dickinson Labware), the sample solution was diluted with PBS in two steps. Then the same amount of a 0.5% avian erythrocyte suspension was added thereto and the mixture was stirred well. After reacting at room temperature for 1 hour, agglutination of the erythrocytes was observed. The highest dilution ratio showing agglutination was taken as the HA value.

The HA value of the stem region polypeptide was less than 1/1000 of the HA value of HA molecules.

Thus it has been clarified that the stem region polypeptide prepared by the treatment with the protease has an antigenicity comparable to that of HA molecules and the hemagglutination activity originating in the globular head region has substantially disappeared.

This polypeptide can easily serve as an antigen determinant and the globular head region, which is liable to undergo antigen mutation, has been digested therefrom. Thus it is usable as a vaccine capable of specifically recognizing the stem region of H3N2 subtype and inducing an antibody neutralizing the virus.

EXAMPLE 10
Preventive Effect on Influenza Virus:

From *Escherichia Coli* JM109/pENH2dH01 (FERM BP-4190), a plasmid pENH2dH01 having, integrated thereinto, a gene codes for a polypeptide lacking the globular head region of A/Okuda/57 (H1N1) HA molecule was prepared.

Trypsin treated CV-1 cells ($5 \times 10^6$ cells) were washed with 20 ml 10% FCS-MEM in one time, and 20 ml PBS in two times, and suspended in 1 ml PBS. The 0.8 ml part of it and the plasmid pENH3dH01 (30 mg) were put into a cuvette for GENEPULSER™, and the cuvette was set into GENEPULSER™. The cells and plasmid were treated in 250V, 960 mFD by GENEPULSER™. After the sample was put at 0° C. for 10 minutes, the cells were suspended in 60 ml 10% FCS-MEM and 5ml each was cultured in a dish (6 cm).

On the third day of the incubation, the expression of the polypeptide was confirmed by a staining test with, the use of C179. Cells in which the polypeptide had been expressed were treated with PBS containing trypsin and then harvested by centrifugation. The cells thus harvested were suspended in PBS and intraperitoneally administered to 10 female BALB/c mice aged 4 weeks as a vaccine in a dose of $1 \times 10^5$/animal. Two weeks thereafter, the second immunization was carried out in the same manner. As a control, CV-1 cells which had not been transformed by pENH2dH01 were used. These control cells were also intraperitoneally administered twice to 10 mice in a dose of $1 \times 10^5$ cells/animal. One week after the final immunization, 25 µl ($8 \times 10^4$ FFU) of A1/FM/1/47 (H1N1) was intranasally administered to the mice. Subsequently, the life or death of the animals was checked everyday.

Figure 4:
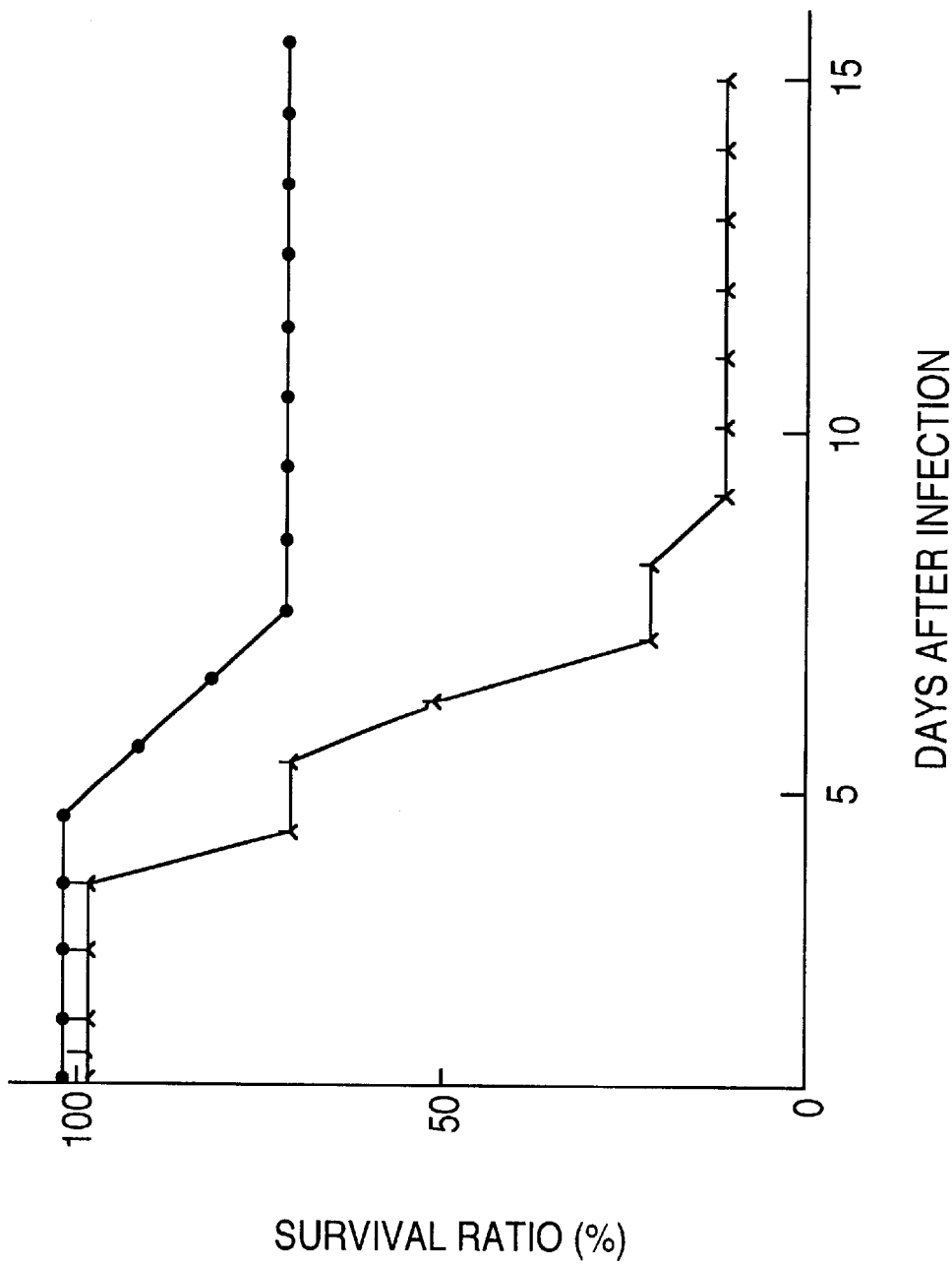
FIG. 4 is a graph showing the survival ratio of a group infected with influenza virus.

FIG. 4 shows the results. As FIG. 4 shows, 7 mice among 10 of the test group (black circle) immunized with the CV-1 cells with the expression of the antigen polypeptide survived 15 days after the inoculation of the highly toxic strain A1/FM/1/47. In contrast, 9 mice among 10 of the control group (black triangle) died.

FIG. 4 shows the survival ratios of the test (antigen polypeptide-administered) group and the control group wherein the ordinate refers to the survival ratio while the abscissa refers to the time (days) after the infection with the virus.

Thus it has been clarified that the antigen polypeptide lacking the globular head region of HA molecules can serve as a vaccine for the virus of the H1N1 subtype, though it per se origins in the H2N2 subtype.

This polypeptide can easily serve as an antigen determinant and the globular head region, which is liable to undergo antigen mutation, has been digested therefrom. Thus it is usable as a vaccine capable of specifically recognizing the stem region of the H1N1 and H2N2 subtypes and inducing an antibody neutralizing the viruse

EXAMPLE 11

Preventive Effect on Influenza Virus:

By using the stem Polypeptide described in the Example 8 as a test saltple, the preventive effect on the infection with influenza virus was examined. The stem region polypeptide was suspended in PBS and intraperitoneally administered to female Balbic mice. aged 4 weeks in a dose of 10 µg/0.5 ml/animal. The animals were immunized thrice in total by repeating the intraperitoneal administration in the same does at intervals of 1 week. To a control group, FBS alone was administered. Ten days after the final immunization, the animals were intranasally inoculated with 25 µl ($2.0 \times 10^3$ FFU) per animal of A1/FM/1/47 (H1N1) virus. Then the life and death of the animals were observed and changes in the body weight of surviving mice were monitored.

Figure 5:
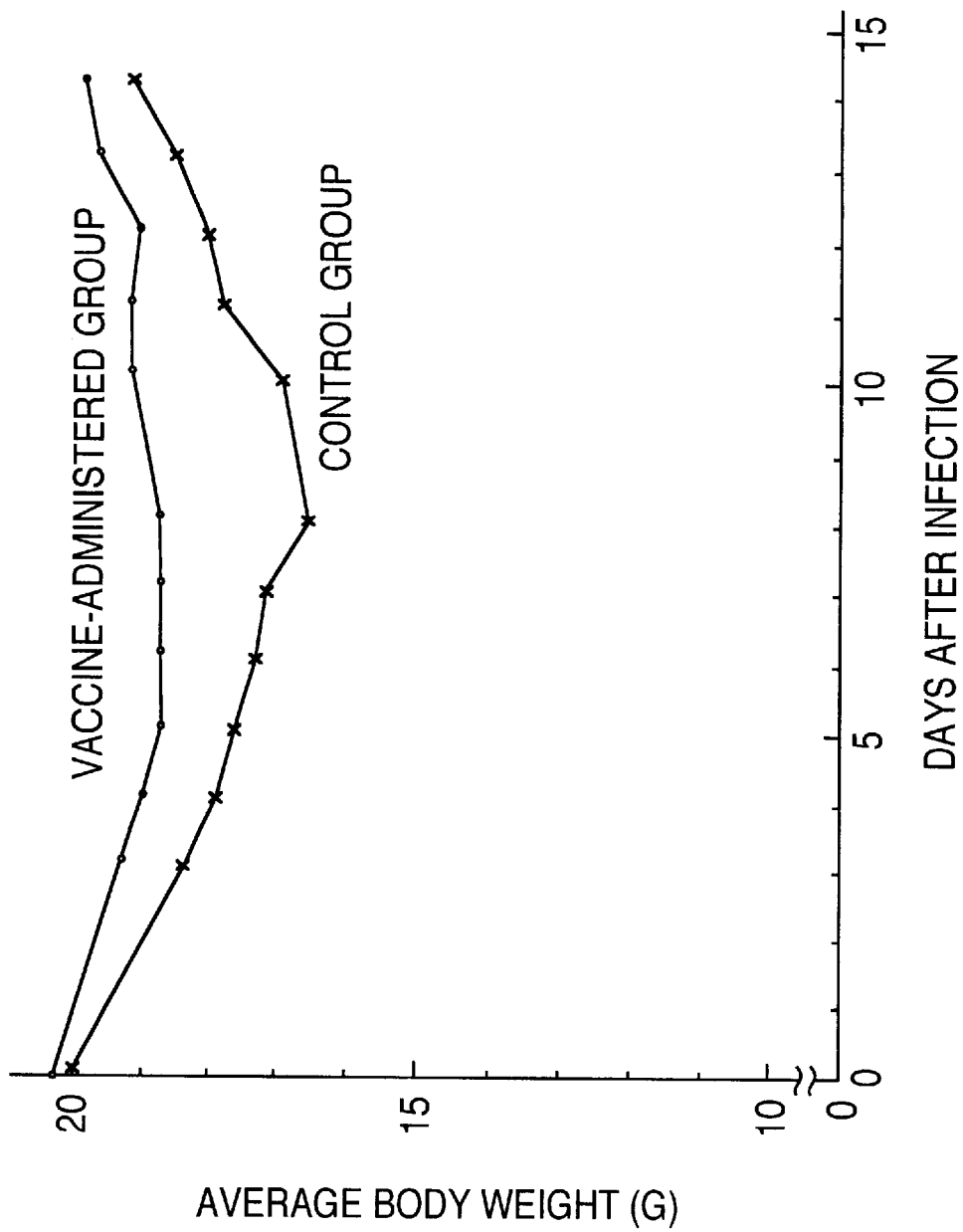
FIG. 5 is a graph showing the average body weight loss of a group infected with influenza virus.
Figure 6:
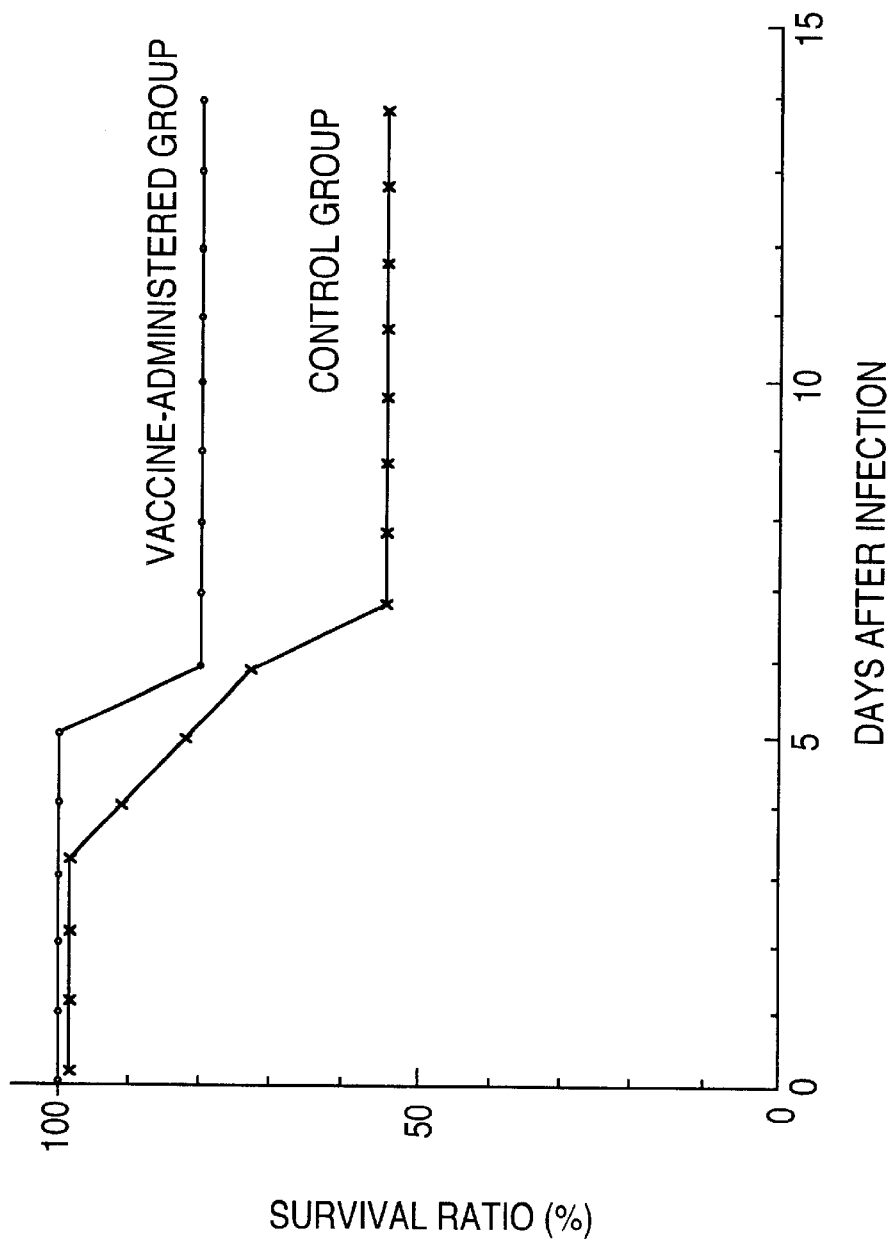
FIG. 6 is a graph showing the survival ratio of a group infected with influenza virus.

As FIG. 5 shows the average body weight loss of the mice immunized with the stem region polypeptide was significantly lower than that of the control group. As FIG. 6 shows, further, 5 mice among 11 in the control group died within 7 days after the inoculation with the virus, while 8 mice among 10 immunized with the stem region polypeptide survived for 14 days after the inoculation, thus showing a survival ratio 14 days after the inoculation with the virus of 80%.

On the other hand, the survival ratio of the control group 14 days after the inoculation was 55%.

FIG. 5 is a graph showing the body weight changes of the stem region polypeptide-administered group and the control group wherein the ordinate indicates the average body weight of the surviving mice of each group while the abscissa indicates the time (days) after the inoculation with the virus. FIG. 6 is a graph showing the survival ratios of the stem region polypeptide-administered group and the control group wherein the ordinate indicates the survival ratio of each group while the abscissa indicates the time (days) after the inoculation with the virus.

Thus it has been clarified that the antigen polypeptide lacking the globular head region of HA molecules can serve as a vaccine for the influenza virus.

In conclusion, the present invention provides an antibody which is useful in the diagnosis, prevention and treatment of infection with human influenza A virus. The antigen site recognized by this antibody is conserved widely in virus subtypes and capable of inducing a neutralization antibody. Thus a polypeptide containing this site is valuable as a vaccine.

The present invention provides an immunogenic polypeptide capable of producing an antibody, which binds specifically to the stem region in HA molecule of the subtypes of human influenza A virus, and a gene coding for this polypeptide.

Especially, the polypeptide lacking the globular head region of HA molecule can be provided for a huge amount by gene recombination technology and it is very useful for the vaccine prevent from influenza virus because this polypeptide has no control under the antigenic mutation of the globular head region of HA molecule.

What is claimed is:

1. An isolated polypeptide comprising an amino acid sequence including a TGLRN polypeptide sequence of SEQ ID No. 1 and a GITNKVNSVIEK polypeptide sequence of SEQ ID No. 2, which lacks the globular head region of hemagglutinin of human influenza A virus and which lacks hemagglutinin activity.

2. The isolated polypeptide according to claim 1, which is recognized by monoclonal antibody C179 produced by hybridoma C179 (FERM BP-4517).

3. A composition comprising the polypeptide according to claim 1 together with a carrier and/or adjuvant.

4. The isolated polypeptide according to claim 1, wherein said polypeptide comprises an amino acid sequence which elicits an immune response in a mammal, which generates an antibody that specifically binds to an epitope located on both the HA1 and HA2 stem regions of hemagglutinin of either intact human influenza A virus subtypes H1N1 or H2N2.

5. An isolated polypeptide comprising an amino acid sequence including a TGMRN polypeptide sequence of SEQ ID No. 3 and a QINGKLNR(L/V)IEK polypeptide sequence of SEQ ID No. 4, which lacks the globular head region of hemagglutinin of human influenza A virus and which lacks hemagglutinin activity.

6. The isolated polypeptide according to claim 5, wherein said polypeptide comprises an amino acid sequence which elicits an immune response in a mammal, which generates an antibody that specifically binds to an epitope located on both the HA1 and HA2 stem regions of hemagglutinin of intact human influenza A virus subtype H3N2.

7. The isolated polypeptide according to claim 5, which is recognized by monoclonal antibody AI3C produced by hybridoma AI3C (FERM BP-4516).

8. A composition comprising the polypeptide according to claim 5 together with a carrier and/or adjuvant.

9. A method for producing a polypeptide according to claim 1, or 5, which comprises treating hemagglutinin of human influenza A virus containing a globular head region and a stem region with a proteinase to remove the globular head region, and then separating the stem region to obtain the polypeptide.

10. The method according to claim 9, wherein the proteinase is proteinase K.

* * * * *

SEQUENCE LISTING (1) GENERAL INFORMATION:

(iii) NUMBER OF SEQUENCES:  58

(2) INFORMATION FOR SEQ ID NO:1:

(i) SEQUENCE CHARACTERISTICS:
         (A) LENGTH:  5 amino acids
         (B) TYPE:  amino acid
         (C) STRANDEDNESS:  single
         (D) TOPOLOGY:  linear (ii) MOLECULE TYPE:  peptide (iii) HYPOTHETICAL:

(iv) ANTI-SENSE:

(v) FRAGMENT TYPE:  internal fragment (vi) ORIGINAL SOURCE:
         (A) ORGANISM:
         (B) STRAIN:
         (C) INDIVIDUAL ISOLATE:
         (D) DEVELOPMENTAL STAGE:
         (E) HAPLOTYPE:
         (F) TISSUE TYPE:
         (G) CELL TYPE:
         (H) CELL LINE:
         (I) ORGANELLE:

(vii) IMMEDIATE SOURCE:
         (A) LIBRARY:
         (B) CLONE:

(viii) POSITION IN GENOME:
         (A) CHROMOSOME/SEGMENT:
         (B) MAP POSITION:
         (C) UNITS:

(ix) FEATURE:
         (A) NAME/KEY:
         (B) LOCATION:
         (C) IDENTIFICATION METHOD:
         (D) OTHER INFORMATION:

(x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO:1:

Thr Gly Leu Arg Asn
 1               5

(2) INFORMATION FOR SEQ ID NO:2:

(i) SEQUENCE CHARACTERISTICS:
         (A) LENGTH:  12 amino acids
         (B) TYPE:  amino acid
         (C) STRANDEDNESS:  single
         (D) TOPOLOGY:  linear (ii) MOLECULE TYPE:  peptide

```
    (iii) HYPOTHETICAL:

(iv) ANTI-SENSE:

(v) FRAGMENT TYPE:  internal fragment (vi) ORIGINAL SOURCE:
          (A) ORGANISM:
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

(vii) IMMEDIATE SOURCE:
          (A) LIBRARY:
          (B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:2:

Gly Ile Thr Asn Lys Val Asn Ser Val Ile Glu Lys
 1               5                  10

(2) INFORMATION FOR SEQ ID NO:3:

(i) SEQUENCE CHARACTERISTICS:
          (A) LENGTH:  5 amino acids
          (B) TYPE:  amino acid
          (C) STRANDEDNESS:  single
          (D) TOPOLOGY:  linear (ii) MOLECULE TYPE:  peptide (iii) HYPOTHETICAL:

(iv) ANTI-SENSE:

(v) FRAGMENT TYPE:  internal fragment (vi) ORIGINAL SOURCE:
          (A) ORGANISM:
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

(vii) IMMEDIATE SOURCE:
```

```
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:3:

Thr Gly Met Arg Asn
 1               5

(2) INFORMATION FOR SEQ ID NO:4:

(i) SEQUENCE CHARACTERISTICS:
            (A) LENGTH:  12 amino acids
            (B) TYPE:  amino acid
            (C) STRANDEDNESS:  single
            (D) TOPOLOGY:  linear (ii) MOLECULE TYPE:  peptide (iii) HYPOTHETICAL:

(iv) ANTI-SENSE:

(v) FRAGMENT TYPE:  internal fragment (vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION: 9
            (C) IDENTIFICATION METHOD:
            (D) OTHER INFORMATION:   /note= "Val or Leu"

(x) PUBLICATION INFORMATION:
            (A) AUTHORS:
            (B) TITLE:
            (C) JOURNAL:
```

-continued

```
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:4:

Gln Ile Asn Gly Lys Leu Asn Arg Xaa Ile Glu Lys
 1               5                  10

(2) INFORMATION FOR SEQ ID NO:5:

(i) SEQUENCE CHARACTERISTICS:
            (A) LENGTH:  19 bases
            (B) TYPE:  nucleic acid
            (C) STRANDEDNESS:  single
            (D) TOPOLOGY:  linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:5:

AGCAAAAGCA GGGGATAAT                                              19

(2) INFORMATION FOR SEQ ID NO:6:

(i) SEQUENCE CHARACTERISTICS:
            (A) LENGTH:  21 bases
```

```
          (B) TYPE:  nucleic acid
          (C) STRANDEDNESS:  single
          (D) TOPOLOGY:  linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
          (A) ORGANISM:
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

(vii) IMMEDIATE SOURCE:
          (A) LIBRARY:
          (B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:6:

AGTAGAAACA AGGGTGTTTT T                                              21

(2) INFORMATION FOR SEQ ID NO:7:

(i) SEQUENCE CHARACTERISTICS:
          (A) LENGTH:  23 bases
          (B) TYPE:  nucleic acid
          (C) STRANDEDNESS:  single
          (D) TOPOLOGY:  linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
          (A) ORGANISM:
          (B) STRAIN:
          (C) INDIVIDUAL ISOLATE:
          (D) DEVELOPMENTAL STAGE:
          (E) HAPLOTYPE:
          (F) TISSUE TYPE:
```

```
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:7:

TCTTTTCGAG TACTGTGTCA ACA                                          23

(2) INFORMATION FOR SEQ ID NO:8:

(i) SEQUENCE CHARACTERISTICS:
            (A) LENGTH:  23 bases
            (B) TYPE:  nucleic acid
            (C) STRANDEDNESS:  single
            (D) TOPOLOGY:  linear (ii) MOLECULE TYPE:   other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:
```

```
    (x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:8:

GCCCCACTAC AATTGGGGAA ATG                                             23

(2) INFORMATION FOR SEQ ID NO:9:

(i) SEQUENCE CHARACTERISTICS:
        (A) LENGTH:  24 bases
        (B) TYPE:  nucleic acid
        (C) STRANDEDNESS:  single
        (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:9:

TTTTACAGAA ATTTGCTATG GCTG                                            24

(2) INFORMATION FOR SEQ ID NO:10:
```

```
      (i) SEQUENCE CHARACTERISTICS:
          (A) LENGTH:  24 bases
          (B) TYPE:  nucleic acid
          (C) STRANDEDNESS:  single
          (D) TOPOLOGY:  linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
          (A) ORGANISM:
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

(vii) IMMEDIATE SOURCE:
          (A) LIBRARY:
          (B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:10:

ACTCCCCTAT TGTGACTGGG TGTA                                            24

(2) INFORMATION FOR SEQ ID NO:11:

(i) SEQUENCE CHARACTERISTICS:
          (A) LENGTH:  22 bases
          (B) TYPE:  nucleic acid
          (C) STRANDEDNESS:  single
          (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
          (A) ORGANISM:
          (B) STRAIN:
          (C) INDIVIDUAL ISOLATE:
```

```
           (D) DEVELOPMENTAL STAGE:
           (E) HAPLOTYPE:
           (F) TISSUE TYPE:
           (G) CELL TYPE:
           (H) CELL LINE:
           (I) ORGANELLE:

(vii) IMMEDIATE SOURCE:
           (A) LIBRARY:
           (B) CLONE:

(viii) POSITION IN GENOME:
           (A) CHROMOSOME/SEGMENT:
           (B) MAP POSITION:
           (C) UNITS:

(ix) FEATURE:
           (A) NAME/KEY:
           (B) LOCATION:
           (C) IDENTIFICATION METHOD:
           (D) OTHER INFORMATION:

(x) PUBLICATION INFORMATION:
           (A) AUTHORS:
           (B) TITLE:
           (C) JOURNAL:
           (D) VOLUME:
           (E) ISSUE:
           (F) PAGES:
           (G) DATE:
           (H) DOCUMENT NUMBER:
           (I) FILING DATE:
           (J) PUBLICATION DATE:
           (K) RELEVANT RESIDUES IN SEQ ID NO:

(xi) SEQUENCE DESCRIPTION: SEQ ID NO:11:

GGTTATCATC ATCAGAATGA AC                                              22

(2) INFORMATION FOR SEQ ID NO:12:

(i) SEQUENCE CHARACTERISTICS:
           (A) LENGTH:  24 bases
           (B) TYPE:  nucleic acid
           (C) STRANDEDNESS:  single
           (D) TOPOLOGY:  linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
           (A) ORGANISM:
           (B) STRAIN:
           (C) INDIVIDUAL ISOLATE:
           (D) DEVELOPMENTAL STAGE:
           (E) HAPLOTYPE:
           (F) TISSUE TYPE:
           (G) CELL TYPE:
           (H) CELL LINE:
           (I) ORGANELLE:

(vii) IMMEDIATE SOURCE:
           (A) LIBRARY:
           (B) CLONE:

(viii) POSITION IN GENOME:
           (A) CHROMOSOME/SEGMENT:
           (B) MAP POSITION:
           (C) UNITS:

(ix) FEATURE:
           (A) NAME/KEY:
           (B) LOCATION:
```

```
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:12:

AGTTCACCTT GTTTGTAATC CCGT                                          24

(2) INFORMATION FOR SEQ ID NO:13:

(i) SEQUENCE CHARACTERISTICS:
            (A) LENGTH:  24 bases
            (B) TYPE:  nucleic acid
            (C) STRANDEDNESS:  single
            (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:13:

CCATTTTTTA CTCTTTCCAT GCAT                                          24
```

(2) INFORMATION FOR SEQ ID NO:14:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:14:

ATCTACTCAA CTGTCGCCAG TTCA                      24

(2) INFORMATION FOR SEQ ID NO:15:

(i) SEQUENCE CHARACTERISTICS:
        (A) LENGTH: 23 bases
        (B) TYPE: nucleic acid
        (C) STRANDEDNESS: single
        (D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:

```
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:15:

TTGTGTCGAC CTTCTCTGTG GAA                                              23

(2) INFORMATION FOR SEQ ID NO:16:

(i) SEQUENCE CHARACTERISTICS:
            (A) LENGTH:   20 bases
            (B) TYPE:  nucleic acid
            (C) STRANDEDNESS:  single
            (D) TOPOLOGY:   linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:
```

```
    (ix) FEATURE:
         (A) NAME/KEY:
         (B) LOCATION:
         (C) IDENTIFICATION METHOD:
         (D) OTHER INFORMATION:

(x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO:16:

TGTAGCATTG CCGGATGGCT                                               20

(2) INFORMATION FOR SEQ ID NO:17:

(i) SEQUENCE CHARACTERISTICS:
         (A) LENGTH:  23 bases
         (B) TYPE:  nucleic acid
         (C) STRANDEDNESS:  single
         (D) TOPOLOGY:  linear (ii) MOLECULE TYPE:   other nucleic acid (synthetic DNA)

(iii) HYPOTHETICAL:

(iv) ANTI-SENSE:

(v) FRAGMENT TYPE:

(vi) ORIGINAL SOURCE:
         (A) ORGANISM:
         (B) STRAIN:
         (C) INDIVIDUAL ISOLATE:
         (D) DEVELOPMENTAL STAGE:
         (E) HAPLOTYPE:
         (F) TISSUE TYPE:
         (G) CELL TYPE:
         (H) CELL LINE:
         (I) ORGANELLE:

(vii) IMMEDIATE SOURCE:
         (A) LIBRARY:
         (B) CLONE:

(viii) POSITION IN GENOME:
         (A) CHROMOSOME/SEGMENT:
         (B) MAP POSITION:
         (C) UNITS:

(ix) FEATURE:
         (A) NAME/KEY:
         (B) LOCATION:
         (C) IDENTIFICATION METHOD:
         (D) OTHER INFORMATION:

(x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:
```

(xi) SEQUENCE DESCRIPTION: SEQ ID NO:17:

ATTATCCGGT TGCCAAAGGA TCG                                                      23

(2) INFORMATION FOR SEQ ID NO:18:

(i) SEQUENCE CHARACTERISTICS:
        (A) LENGTH:  23 bases
        (B) TYPE:  nucleic acid
        (C) STRANDEDNESS:  single
        (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:18:

GAGAGCACTG GTAATCTGTT GCA                                                      23

(2) INFORMATION FOR SEQ ID NO:19:

(i) SEQUENCE CHARACTERISTICS:
        (A) LENGTH:  23 bases
        (B) TYPE:  nucleic acid
        (C) STRANDEDNESS:  single
        (D) TOPOLOGY:  linear (ii) MOLECULE TYPE:  other nucleic acid (synthetic DNA)

(iii) HYPOTHETICAL:

(iv) ANTI-SENSE:

```
        (v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:19:

CCATCAAATG CCTTTTGAGT GGA                                              23

(2) INFORMATION FOR SEQ ID NO:20:

(i) SEQUENCE CHARACTERISTICS:
          (A) LENGTH:  23 bases
          (B) TYPE:  nucleic acid
          (C) STRANDEDNESS:  single
          (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
          (A) ORGANISM:
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

(vii) IMMEDIATE SOURCE:
          (A) LIBRARY:
          (B) CLONE:

(viii) POSITION IN GENOME:
          (A) CHROMOSOME/SEGMENT:
```

```
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:20:

ACTAGAAGCT CAGCATTGTA TGT                                                23

(2) INFORMATION FOR SEQ ID NO:21:

(i) SEQUENCE CHARACTERISTICS:
            (A) LENGTH:  24 bases
            (B) TYPE:  nucleic acid
            (C) STRANDEDNESS:  single
            (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
```

```
        (J) PUBLICATION DATE:
        (K) RELEVANT RESIDUES IN SEQ ID NO:

(xi) SEQUENCE DESCRIPTION: SEQ ID NO:21:

CATGCATTCA TCATCACATT TGTG                                              24

(2) INFORMATION FOR SEQ ID NO:22:

(i) SEQUENCE CHARACTERISTICS:
        (A) LENGTH:  23 bases
        (B) TYPE:  nucleic acid
        (C) STRANDEDNESS:  single
        (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:22:

CATACTTGGG ATAATCATAC GTC                                               23

(2) INFORMATION FOR SEQ ID NO:23:

(i) SEQUENCE CHARACTERISTICS:
        (A) LENGTH:  23 bases
        (B) TYPE:  nucleic acid
        (C) STRANDEDNESS:  single
        (D) TOPOLOGY:  linear (ii) MOLECULE TYPE:  other nucleic acid (synthetic DNA)

(iii) HYPOTHETICAL:
```

```
        (iv) ANTI-SENSE:

(v) FRAGMENT TYPE:

(vi) ORIGINAL SOURCE:
             (A) ORGANISM:
             (B) STRAIN:
             (C) INDIVIDUAL ISOLATE:
             (D) DEVELOPMENTAL STAGE:
             (E) HAPLOTYPE:
             (F) TISSUE TYPE:
             (G) CELL TYPE:
             (H) CELL LINE:
             (I) ORGANELLE:

(vii) IMMEDIATE SOURCE:
             (A) LIBRARY:
             (B) CLONE:

(viii) POSITION IN GENOME:
             (A) CHROMOSOME/SEGMENT:
             (B) MAP POSITION:
             (C) UNITS:

(ix) FEATURE:
             (A) NAME/KEY:
             (B) LOCATION:
             (C) IDENTIFICATION METHOD:
             (D) OTHER INFORMATION:

(x) PUBLICATION INFORMATION:
             (A) AUTHORS:
             (B) TITLE:
             (C) JOURNAL:
             (D) VOLUME:
             (E) ISSUE:
             (F) PAGES:
             (G) DATE:
             (H) DOCUMENT NUMBER:
             (I) FILING DATE:
             (J) PUBLICATION DATE:
             (K) RELEVANT RESIDUES IN SEQ ID NO:

(xi) SEQUENCE DESCRIPTION: SEQ ID NO:23:

GCCATTTATG CTACAGTAGC AGG                                                    23

(2) INFORMATION FOR SEQ ID NO:24:

(i) SEQUENCE CHARACTERISTICS:
             (A) LENGTH: 24 bases
             (B) TYPE: nucleic acid
             (C) STRANDEDNESS: single
             (D) TOPOLOGY: linear (ii) MOLECULE TYPE: other nucleic acid (synthetic DNA)

(iii) HYPOTHETICAL:

(iv) ANTI-SENSE:

(v) FRAGMENT TYPE:

(vi) ORIGINAL SOURCE:
             (A) ORGANISM:
             (B) STRAIN:
             (C) INDIVIDUAL ISOLATE:
             (D) DEVELOPMENTAL STAGE:
             (E) HAPLOTYPE:
             (F) TISSUE TYPE:
             (G) CELL TYPE:
             (H) CELL LINE:
             (I) ORGANELLE:

(vii) IMMEDIATE SOURCE:
             (A) LIBRARY:
             (B) CLONE:
```

```
    (viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:24:

GATCAGATTG AAGTGACTAA TGCT                                           24

(2) INFORMATION FOR SEQ ID NO:25:

(i) SEQUENCE CHARACTERISTICS:
          (A) LENGTH:   24 bases
          (B) TYPE:   nucleic acid
          (C) STRANDEDNESS:   single
          (D) TOPOLOGY:   linear (ii) MOLECULE TYPE:   other nucleic acid (synthetic DNA)

(iii) HYPOTHETICAL:

(iv) ANTI-SENSE:

(v) FRAGMENT TYPE:

(vi) ORIGINAL SOURCE:
          (A) ORGANISM:
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

(vii) IMMEDIATE SOURCE:
          (A) LIBRARY:
          (B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:
          (B) TITLE:
          (C) JOURNAL:
          (D) VOLUME:
          (E) ISSUE:
          (F) PAGES:
```

(G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:25:

GAATGCATCA CTCCAAATGG AAGC                                          24

(2) INFORMATION FOR SEQ ID NO:26:

(i) SEQUENCE CHARACTERISTICS:
        (A) LENGTH:  23 bases
        (B) TYPE:  nucleic acid
        (C) STRANDEDNESS:  single
        (D) TOPOLOGY:  linear (ii) MOLECULE TYPE:   other nucleic acid (synthetic DNA)

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:26:

AGGTCCTGAA TTCTCCCTTC TAC                                           23

(2) INFORMATION FOR SEQ ID NO:27 :

(i) SEQUENCE CHARACTERISTICS:
        (A) LENGTH:  1754 base pairs
        (B) TYPE:  nucleic acid
        (C) STRANDEDNESS:  double
        (D) TOPOLOGY:  linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
    (A) ORGANISM: A/Suita/1/89
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:27:

```
GGATAATAAA TACAACCAAA ATGAAAGCAA AACTACTAGT CCTGTTATGT GCATTTACAG     60

CTACAGATGC AGACACAATA TGTATAGGCT ACCATGCGAA CAACTCAACC GACACTGTTG    120

ACACAGTACT TGAGAAGAAC GTGACAGTGA CACACTCTGT CAACCTACTT GAGGACAGTC    180

ACAACGGAAA ACTATGTCGA CTAAAAGGAA TAGCCCCACT ACAATTGGGT AATTGCAGCA    240

TTGCCGGATG GATCTTAGGA AACCCAGAAT GCGAATCACT GTTTTCTAAG GAATCATGGT    300

CCTACATTGC AGAAACACCA AACTCCGAGA ATGGAACATG TTACCCAGGG TATTTCGCCG    360

ACTATGAGGA ACTGAGGGAG CAATTGAGTT CAGTATCATC ATTCGAGAGA TTCGAAATAT    420

TCCCCAAAGA AAGCTCATGG CCCAACCACA CCGTAACCAA AGGAGTAACG GCATCATGCT    480

CCCATAATGG GAAAAGCAGT TTTTACAGAA ATTTGCTATG GCTGACGGGG AAGAATGGCT    540

TGTACCCAAA TCTGAGCAAG TCCTATGTGA ACAACAAAGA GAAAGAAGTC CTTGTACTAT    600

GGGGTGTTCA TCACCCGTCT AACATAGGGG ACCAAAGGGC CATCTATCAT ACAGAAAATG    660

CTTATGTCTC TGTAGTGTCT TCACATTATA GCAGGAGATT CACCCCAGAA ATAGCAAAAA    720

GACCCAAAGT AAGAGGTCAA GAAGGAAGAA TTAACTACTA CTGGACTCTG CTGGAACCCG    780

GGGACACAAT AATATTTGAG GCAAATGGAA ATCTAATAGC GCCATGGTAT GCTTTCGCAC    840

TGAGTAGAGG CTTTGGGTCA GGAATCATCA CCTCAAACGC ATCAATGGAT GAATGTGACG    900
```

```
CGAAGTGTCA AACACCCCAG GGAGCTATAA ACAGTAGTCT TCCTTTCCAG AATGTACACC    960

CAGTCACAAT AGGAGAGTGT CCAAAGTATG TCAGGAGTAC AAAATTAAGG ATGGTTACAG   1020

GACTAAGGAA CATCCCATCC ATTCAATCCA GAGGTTTGTT TGGAGCCATT GCCGGTTTCA   1080

TTGAAGGGGG GTGGACTGGA ATGATAGATG GATGGTATGG TTATCATCAT CAGAATGAAC   1140

AAGGATCTGG CTATGCTGCG GATCAAAAAA GCACACAAAA TGCCATTAAC GGAATTACAA   1200

ACAAGGTGAA TTCTGTAATC GAGAAAATGA ACACTCAATT CACAGCTGTG GGCAAAGAAT   1260

TCAACAAATT AGAAAGAAGG ATGGAATACT TAAATAAAAA AGTTGATGAT GGATTTCTGG   1320

ACATTTGGAC ATATAATGCA GAATTGTTGG TTCTACTGGA AAATGAAAGG ACTTTGGATT   1380

TTCATGACTC AAATGTGAAG AATCTGTATG AGAAAGTAAA AAGCCAATTA AAGAATAATG   1440

CCAAAGAAAT AGGATACGGG TGTTTTGAAT CTACCACAA GTGTAACAAT GAATGCATGG    1500

AAAGTGTGAA AAATGGAACT TATGACTATC CAAAATATTC CGAGGAATCA AGTTAAACA    1560

GGGAAAAAAT TGATGGAGTG AAATTGGAAT CAATGGGAGT CTATCAGATT CTGGCGATCT   1620

ACTCAACTGT CGCCAGTTCA CTGGTGCTTT TGGTCTCCCT GGGGGCAATC AGCTTCTGGA   1680

TGTGTTCTAA TGGGTCTTTG CAGTGTAGAA TATGCATCTG AGACCAGAAT TCAGAAATA   1740

TAAGAAAAAA CACC                                                    1754
```

(2) INFORMATION FOR SEQ ID NO:28:

(i) SEQUENCE CHARACTERISTICS:
        (A) LENGTH: 1728 base pairs
        (B) TYPE: nucleic acid
        (C) STRANDEDNESS: double
        (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
        (A) ORGANISM: A/lzumi/5/65
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:

(F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:28:

ATAGACAACC AAAAGCATAA CAATGGCCAT CATCTATCTC ATACTCCTGT TCACAGCAGT        60

GAGGGGGGAC CAGATATGCA TTGGATACCA TGCCAATAAT TCCACAGAAA AGGTCGACAC       120

AATTCTAGAG CGGAATGTCA CTGTGACTCA TGCCAAGGAC ATCCTTGAGA AGACCCACAA       180

CGGAAAGCTA TGCAAACTAA ACGGAATCCC TCCACTTGAA CTAGGGGACT GTAGCATTGC       240

CGGATGGCTC CTTGGAAATC CAGAATGTGA TAGGCTTCTA AGGGTGCCAG AATGGTCCTA       300

TATAATGGAG AAAGAAAACC CGAGATACAG TTTATGTTAC CCAGGCAACT TCAATGACTA       360

TGAAGAATTG AAACATCTCC TCAGCAGCGT AAAACATTTC GAGAAAGTAA AGATTCTGCC       420

CAAAGATAGA TGGACACAGC ATACAACAAC TGGAGGTTCA AAGGCCTGCG CAGTGTCAGG       480

TAAACCATCA TTCTTCAGGA ACATGGTCTG GCTGACAAAG AAAGGACCAA ATTATCCGGT       540

TGCCAAAGGA TCGTACAACA ATACGAGCGG AGAGCAAATG CTAATAATTT GGGGAGTGCA       600

CCATCCTAAT GATGAGGCAG AACAAAGAGC ATTGTACCAG GAAGTGGGAA CCTATGTTTC       660

CGCAAGCACA TCAACATTGA ACAAAAGGTC AATCCCTGAA ATAGCAGCAA GGCCTAAAGT       720

GAATGGACTA GGAAGTAGAA TGGAATTCTC TTGGACCCTC TTGGATGTGT GGGACACCAT       780

AAATTTTGAG AGCACTGGTA ATCTAGTTGC ACCAGAGTAT GGATTCAAAA TATCGAAAAG       840

AGGTAGTTCA GGGATCATGA AGACAGAAGG AACACTTGGG AACTGTGAGA CCAAATGCCA       900

AACTCCTTTG GGAGCAATAA ATACAACACT ACCTTTTCAC AATGTCCACC CACTGACAAT       960

AGGTGAATGC CCCAAATATG TAAAATCGGA GAAATTGGTC TTAGCAACAG GACTAAGGAA      1020

TGTTCCCCAG ATTGAATCAA GAGGATTGTT TGGGGCAATA GCTGGCTTTA TAGAAGGAGG      1080

ATGGCAAGGA ATGGTTGATG GTTGGTATGG ATACCATCAC AGCAATGACC AGGGATCAGG      1140

GTATGCAGCA GACAAAGAAT CCACTCAAAA GGCATTTGAT GGAATCACCA ACAAGGTAAA      1200

TTCTGTGATT GAAAAGATGA ACACCCAATT TGAAGCTGTT GGGAAAGAAT TCAATAATTT      1260

AGAGAAAAGA CTGGAGAACT TGAACAAAAA GATGGAAGAC GGGTTTCTAG ATGTGTGGAC      1320

ATACAATGCT GAGCTTCTAG TTCTGATGGA AAATGAGAGG ACACTTGACT TCCATGATTC      1380

TAATGTCAAG AACCTGTATG ATAAAGTCAG AATGCAGCTG AGAGACAACG TCAAAGAACT      1440

AGGAAATGGA TGTTTTGAAT TTTATCACAA ATGTGACGAT GAATGCATGA ATAGTGTGAA      1500

AAACGGGACG TATGATTATC CCAAGTATGA AGAAGAATCT AAACTAAATA GAAATGAAAT      1560

CAAAGGGGTA AAATTGAGCA GCATGGGGGT TTACCAAATT CTTGCCATTT ATGCTACAGT      1620

TGCAGGTTCT CTGTCACTGG CAATCATGAT GGCTGGGATC TCTTTCTGGA TGTGCTCCAA      1680

CGGGTCTCTG CAGTGCAGAA TCTGCATATG ATTGTAATTT ATTTTATA                  1728

(2) INFORMATION FOR SEQ ID NO:29:

(i) SEQUENCE CHARACTERISTICS:
        (A) LENGTH: 442 base pairs
        (B) TYPE: nucleic acid
        (C) STRANDEDNESS: double
        (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
            (A) ORGANISM:  A/PR/8/34
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:29:

CCTTTCCAGA ATATACACCC AGTCACAATA GGAGAGTGCC CAAAATACGT CAGGAGTGCC       60

AAATTGAGGA TGGTTACAGG ACTAAGGAAC ATCCCGTCCA TTCAATCCAG AGGTCTATTT      120

GGAGCCATTG CCGGTTTTAT TGAAGGGGGA TGGACTGGAA TGATAGATGG ATGGTATGGT      180

TATCATCATC AGAATGAACA GGGATCAGGC TATGCAGCGG ATCAAAAAAG CACACAAAAT      240

GCCATTAACG GGATTACAAA CAAGGTGAAC TCTGTTATCG AGAAAATGAA CACTCAATTC      300

ACAGCTGTGG GTAAAGAATT CAACAAATTA GAAAAAGGA TGGAAAATTT AAATAAAAAA      360

GTTGATGATG GATTTCTGGA CATTTGGACA TATAATGCAG AATTGTTAGT TCTACTGGAA      420

AATGAAAGGA CTCTGGATTT CC                                              442

(2) INFORMATION FOR SEQ ID NO:30:

(i) SEQUENCE CHARACTERISTICS:
            (A) LENGTH:   424 base pairs
            (B) TYPE:  nucleic acid
            (C) STRANDEDNESS:  double
            (D) TOPOLOGY:  linear (ii) MOLECULE TYPE:  cDNA to genomic RNA (iii) HYPOTHETICAL:

(iv) ANTI-SENSE:

(v) FRAGMENT TYPE:

(vi) ORIGINAL SOURCE:
            (A) ORGANISM: A/Bangkok/10/83
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:30:

CCTTTCCAGA ATGTACACCC AGTCACAATA GGAGAGTGCC CAAAGTACGT CAGGAGTACA     60

AAATTAAGGA TGGTTACAGG ACTAAGGAAC ATCCCATCCA TTCAATCCAG AGGTTTGTTT    120

GGAGCCATTG CCGGTTTCAT TGAAGGGGGA TGGACTGGAA TGATAGATGG ATGGTATCGT    180

TATCATCATC AGAATGAACA AGGATCTGGC TATGCTGCGG ATCAAAAAG CACACAAAAT     240

GCCATTAACG GGATTACAAA CAAGGTGAAC TCTGTAATCG AGAAAATGAA CACTCAATTC    300

ACAGCTGTGG GTAAAGAATT CAACAAATTA GAAAAAAGGA TGGAAAACTT AAATAAAAAA    360

GTTGATGATG GATTTCTGGA CATTTGGACA TATAATGCAG AATTGTTGGT TCTACTGGAA    420

AATG                                                                 424

(2) INFORMATION FOR SEQ ID NO:31:

(i) SEQUENCE CHARACTERISTICS:
        (A) LENGTH: 424 base pairs
        (B) TYPE: nucleic acid
        (C) STRANDEDNESS: double
        (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
        (A) ORGANISM: A/Yamagata/120/86
        (B) STRAIN:
        (C) INDIVIDUAL ISOLATE:
        (D) DEVELOPMENTAL STAGE:

```
           (E) HAPLOTYPE:
           (F) TISSUE TYPE:
           (G) CELL TYPE:
           (H) CELL LINE:
           (I) ORGANELLE:

(vii) IMMEDIATE SOURCE:
           (A) LIBRARY:
           (B) CLONE:

(viii) POSITION IN GENOME:
           (A) CHROMOSOME/SEGMENT:
           (B) MAP POSITION:
           (C) UNITS:

(ix) FEATURE:
           (A) NAME/KEY:
           (B) LOCATION:
           (C) IDENTIFICATION METHOD:
           (D) OTHER INFORMATION:

(x) PUBLICATION INFORMATION:
           (A) AUTHORS:
           (B) TITLE:
           (C) JOURNAL:
           (D) VOLUME:
           (E) ISSUE:
           (F) PAGES:
           (G) DATE:
           (H) DOCUMENT NUMBER:
           (I) FILING DATE:
           (J) PUBLICATION DATE:
           (K) RELEVANT RESIDUES IN SEQ ID NO:

(xi) SEQUENCE DESCRIPTION: SEQ ID NO:31:

CCTTTCCAGA ATGTACACCC AGTCACAATA GGAGAGTGCC CAAAGTATGT CAGGAGTACA      60

AAATTAAGGA TGGTTACAGG ACTAAGGAAC ATCCCATCCA TTCAATCCAG AGGTTTGTTT     120

GGAGCCATTG CCGGTTTCAT TGAAGGGGGG TGGACTGGAA TGATAGATGG ATGGTATGGT    180

TATCATCATC AGAATGAACA AGGATCTGGC TATGCTGCGG ATCAAAAAAG CACACAAAAT    240

GCCATTAACG GGATTACAAA CAAGGTGAAT TCTGTAATCG AGAAAATGAA CACTCAATTC    300

ACAGCTGTGG GCAAAGAATT CAACAAATTA GAAAGAAGGA TGGAAAACTT AAATAAAAAA    360

GTTGATGATG GATTTCTGGA CATTTGGACA TATAATGCAG AATTGTTGGT CCTACTGGAA    420

AATG                                                                  424

(2) INFORMATION FOR SEQ ID NO:32:

(i) SEQUENCE CHARACTERISTICS:
           (A) LENGTH: 429 base pairs
           (B) TYPE: nucleic acid
           (C) STRANDEDNESS: double
           (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
           (A) ORGANISM: A/Osaka/930/88
           (B) STRAIN:
           (C) INDIVIDUAL ISOLATE:
           (D) DEVELOPMENTAL STAGE:
           (E) HAPLOTYPE:
           (F) TISSUE TYPE:
           (G) CELL TYPE:
           (H) CELL LINE:
           (I) ORGANELLE:
```

```
    (vii) IMMEDIATE SOURCE:
          (A) LIBRARY:
          (B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:32:

CCTTTCCAGA ATGTACACCC AGTCACAATA GGAGAGTGCC CAAAGTATGT CAGGAGTACA      60

AAATTAAGGA TGGTTACAGG ACTAAGGAAC ATCCCATCCA TTCAATCCAG AGGTTTGTTT    120

GGAGCCATTG CCGGTTTCAT AGAAGGGGGG TGGACTGGAA TGATAGATGG ATGGTATGGT    180

TATCATCATC AGAATGAACA AGGATCTGGC TATGCTGCGG ATCAAAAAAG CACACAAAAT    240

GCCATTAACG GAATTACAAA CAAGGTGAAT TCTGTAATCG AGAAAATGAA CACTCAATTC    300

ACAGCTGTGG GCAAAGAATT CAACAAATTA GAAAGAAGGA TGGAAAACTT AAATAAAAAA    360

GTTGATGATG GATTTCTGGA CATTTGGACA TATAATGCAG AATTGTTGGT TCTACTGGAA    420

AATGAAAGG                                                           429

(2) INFORMATION FOR SEQ ID NO:33:

(i) SEQUENCE CHARACTERISTICS:
          (A) LENGTH:  400 base pairs
          (B) TYPE:  nucleic acid
          (C) STRANDEDNESS:  double
          (D) TOPOLOGY:  linear (ii) MOLECULE TYPE:  cDNA to genomic RNA (iii) HYPOTHETICAL:

(iv) ANTI-SENSE:

(v) FRAGMENT TYPE:

(vi) ORIGINAL SOURCE:
          (A) ORGANISM:  A/Okuda/57
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

(vii) IMMEDIATE SOURCE:
          (A) LIBRARY:
          (B) CLONE:
```

```
         (viii) POSITION IN GENOME:
               (A) CHROMOSOME/SEGMENT:
               (B) MAP POSITION:
               (C) UNITS:

(ix) FEATURE:
               (A) NAME/KEY:
               (B) LOCATION:
               (C) IDENTIFICATION METHOD:
               (D) OTHER INFORMATION:

(x) PUBLICATION INFORMATION:
               (A) AUTHORS:
               (B) TITLE:
               (C) JOURNAL:
               (D) VOLUME:
               (E) ISSUE:
               (F) PAGES:
               (G) DATE:
               (H) DOCUMENT NUMBER:
               (I) FILING DATE:
               (J) PUBLICATION DATE:
               (K) RELEVANT RESIDUES IN SEQ ID NO:

(xi) SEQUENCE DESCRIPTION: SEQ ID NO:33:

GCAATAAATA CAACATTACC TTTTCACAAT GTCCACCCAC TGACAATAGG TGAGTGCCCC      60

AAATATGTAA AATCGGAGAA GTTGGTCTTA GCAACAGGAC TAAGGAATGT TCCCCAGATT    120

GAATCAAGAG GATTGTTTGG GGCAATAGCT GGTTTTATAG AAGGAGGATG GCAAGGAATG    180

GTTGACGGTT GGTATGGATA CCATCACAGC AATGACCAGG GATCAGGGTA TGCAGCAGAC    240

AAAGAATCCA CTCAAAAGGC ATTTGATGGA ATCACCAACA AGGTAAATTC TGTGATTGAA    300

AAGATAAACA CCCAATTTGA AGCTGTTGGG AAAGAATTCG GTAACTTAGA GAAAAGACTG    360

GAGAACTTGA ACAAAAAGAT GGAAGACGGG TTTCTAGATG                          400

(2) INFORMATION FOR SEQ ID NO:34:

(i) SEQUENCE CHARACTERISTICS:
          (A) LENGTH:   409 base pairs
          (B) TYPE:   nucleic acid
          (C) STRANDEDNESS:   double
          (D) TOPOLOGY:   linear (ii) MOLECULE TYPE:   cDNA to genomic RNA (iii) HYPOTHETICAL:

(iv) ANTI-SENSE:

(v) FRAGMENT TYPE:

(vi) ORIGINAL SOURCE:
          (A) ORGANISM:   A/Adachi/2/57
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

(vii) IMMEDIATE SOURCE:
          (A) LIBRARY:
          (B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
```

```
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:34:

CGCCTTGGAG CAATAAATAC AACATTGCCT TTTCACAATG TCCACCCACT GACAATAGGT      60

GAGTGCCCCA AATATGTAAA ATCGGAGAAG TTGGTCTTAG CAACAGGACT AAGGAATGTT     120

CCCCAGATTG AATCAAGAGG ATTGTTTGGG GCAATAGCTG GTTTTATAGA AGGAGGATGG     180

CAAGGAATGG TTGATGGTTG GTATGGATAC CATCACAGCA ATGACCAGGG ATCAGGGTAT     240

GCAGCAGACA AAGAATCCAC TCAAAAGGCA TTTGATGGAA TCACCAACAA GGTAAATTCT     300

GTGATTGAAA AGATGAACAC CCAATTTGAA GCTGTTGGGA AAGAATTCGG TAACTTAGAG     360

AGAAGACTGG AGAACTTGAA CAAAAAGATG GAAGACGGGT TTCTAGATG                409

(2) INFORMATION FOR SEQ ID NO:35:

(i) SEQUENCE CHARACTERISTICS:
            (A) LENGTH:  410 base pairs
            (B) TYPE:  nucleic acid
            (C) STRANDEDNESS:  double
            (D) TOPOLOGY:  linear (ii) MOLECULE TYPE:  cDNA to genomic RNA (iii) HYPOTHETICAL:

(iv) ANTI-SENSE:

(v) FRAGMENT TYPE:

(vi) ORIGINAL SOURCE:
            (A) ORGANISM:  A/Kumamoto/1/65
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
```

(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:35:

```
CTCCTTTGGA GCAATAAATA CAACATTACC TTTTCACAAT GTCCACCCAC TGACAATAGG    60

TGAATGCCCC AAATATGTAA AATCGGAGAA ACTGGTCTTA GCAACAGGAC TAAGGAATGT   120

TCCCCAGATT GAATCAAGAG GATTGTTTGG GGCAATAGCT GGCTTTGTAG AAGGAGGATG   180

GCAAGGAATG ATTGATGGTT GGTATGGATA CCATCACAGC AATGATCAGG GATCAGGGTT   240

TGCAGCAGAC AAAGAATCCA CTCAAAAGGC ATTTGATGGA ATCACCAACA AGGTAAATTC   300

TGTGATTGAA AAGATGAACA CCCAATTTGA AGCTGTTGGG AAAGAATTCA ATAATTTAGA   360

GAAAAGACTG GAGAACTTGA ACAAAAGGAT GGAAGACGGG TTTCTAGATG              410
```

(2) INFORMATION FOR SEQ ID NO:36:

(i) SEQUENCE CHARACTERISTICS:
      (A) LENGTH:  394 base pairs
      (B) TYPE:  nucleic acid
      (C) STRANDEDNESS:  double
      (D) TOPOLOGY:  linear (ii) MOLECULE TYPE:  cDNA to genomic RNA (iii) HYPOTHETICAL:

(iv) ANTI-SENSE:

(v) FRAGMENT TYPE:

(vi) ORIGINAL SOURCE:
      (A) ORGANISM:  A/Kaizuka/2/65
      (B) STRAIN:
      (C) INDIVIDUAL ISOLATE:
      (D) DEVELOPMENTAL STAGE:
      (E) HAPLOTYPE:
      (F) TISSUE TYPE:
      (G) CELL TYPE:
      (H) CELL LINE:
      (I) ORGANELLE:

(vii) IMMEDIATE SOURCE:
      (A) LIBRARY:
      (B) CLONE:

(viii) POSITION IN GENOME:
      (A) CHROMOSOME/SEGMENT:
      (B) MAP POSITION:
      (C) UNITS:

(ix) FEATURE:
      (A) NAME/KEY:
      (B) LOCATION:
      (C) IDENTIFICATION METHOD:
      (D) OTHER INFORMATION:

(x) PUBLICATION INFORMATION:
      (A) AUTHORS:
      (B) TITLE:
      (C) JOURNAL:
      (D) VOLUME:
      (E) ISSUE:
      (F) PAGES:
      (G) DATE:
      (H) DOCUMENT NUMBER:
      (I) FILING DATE:

(J) PUBLICATION DATE:
(K) RELEVANT RESIDUES IN SEQ ID NO:

(xi) SEQUENCE DESCRIPTION: SEQ ID NO:36:

```
AATACAACAC TACCTTTTCA CAATGTCCAC CCACTGACAA TAGGTGAATG CCCCAAATAT      60

GTAAAATCGG AGAAATTGGT CTTAGCAACA GGACTAAGGA ATGTTCCCCA GATTGAATCA     120

AGAGGATTGT TTGGGGCAAT AGCTGGCTTT ATAGAAGGAG GATGGCAAGG AATGGTTGAT     180

GGTTGGTATG GATACCATCA CAGCAATGAC CAGGGATCAG GGTATGCAGC AGACAAAGAA     240

TCCACTCAAA AGGCATTTGA TGGAATCACC AACAAGGTAA ATTCTGTGAT TGAAAAGATG     300

AACACCCAAT TTGAAGCTGT TGGGAAAGAA TTCAATAATT TAGAGAAAAG ACTGGAGAAC     360

TTGAACAAAA AGATGGAAGA CGGGTTTCTA GATG                                 394
```

(2) INFORMATION FOR SEQ ID NO:37:

(i) SEQUENCE CHARACTERISTICS:
        (A) LENGTH: 329 base pairs
        (B) TYPE: nucleic acid
        (C) STRANDEDNESS: double
        (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
        (A) ORGANISM: A2/Aichi/2/68
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:37:

```
ATGACAAGCC CTTTCAAAAC GTAAACAAGA TCACATATGG AGCATGCCCC AAGTATGTTA      60
```

```
AGCAAAACAC CCTGAAGTTG GCAACAGGGA TGCGGAATGT ACCAGAGAAA CAAACTAGAG      120

GCCTATTCGG CGCAATAGCA GGTTTCATAG AAAATGGTTG GGAGGGAATG ATAGACGGTT      180

GGTACGGTTT CAGGCATCAA AATTCTGAGG GCACAGGACA AGCAGCAGAT CTTAAAAGCA      240

CTCAAGCAGC CATCGACCAA ATCAATGGGA AATTGAACAG GGTAATCGAG AAGACGAACG      300

AGAAATTCCA TCAAATCGAA AAGGAATTC                                       329
```

(2) INFORMATION FOR SEQ ID NO:38:

(i) SEQUENCE CHARACTERISTICS:
        (A) LENGTH: 334 base pairs
        (B) TYPE: nucleic acid
        (C) STRANDEDNESS: double
        (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
        (A) ORGANISM: A/Fukuoka/C29/85
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:38:

```
ATGACAAACC CTTTCAAAAT GTAAACAAGA TCACATATGG GGCATGTCCC AGGTATGTTA       60

AGCAAAACAC TCTGAAATTG GCAACAGGGA TGCGGAATGT ACCAGAGAAA CAAACTAGAG      120

GCATATTCGG CGCAATAGCA GGTTTCATAG AAAATGGTTG GGAGGGAATG GTAGACGGTT      180

GGTACGGTTT CAGGCATCAA AATTCTGAGG GCACAGGACA AGCAGCAGAT CTTAAAAGCA      240

CTCAAGCAGC AATCGACCAA ATCAACGGGA AACTGAATAG GTTAATCGAG AAGACGAACG      300

AGAAATTCCA TCAAATCGAA AAGGAATTCT CAGA                                 334
```

(2) INFORMATION FOR SEQ ID NO:39:

(i) SEQUENCE CHARACTERISTICS:
        (A) LENGTH: 329 base pairs
        (B) TYPE: nucleic acid
        (C) STRANDEDNESS: double
        (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
        (A) ORGANISM: A/Sichuan/2/87
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:39:

```
ATGACAAACC CTTTCAAAAT GTAAACAAGA TCACATATGG GGCATGTCCC AGATATGTTA      60

AGCAAAACAC TCTGAAATTG GCAACAGGGA TGCGGAATGT ACCAGAGAAA CAAACTAGAG     120

GCATATTCGG CGCAATAGCA GGTTTCATAG AAAATGGTTG GGAGGGAATG GTAGACGGCT     180

GGTACGGTTT CAGGCATCAA AATTCTGAGG GCACAGGACA AGCAGCAGAT CTTAAAAGCA     240

CTCAAGCAGC AATCGACCAA ATCAACGGGA AACTGAATAG GTTAATCGAG AAGACGAACG     300

AGAAATTCCA TCAAACCGAA AAGGAATTC                                      329
```

(2) INFORMATION FOR SEQ ID NO:40:

(i) SEQUENCE CHARACTERISTICS:
        (A) LENGTH: 334 base pairs
        (B) TYPE: nucleic acid
        (C) STRANDEDNESS: double
        (D) TOPOLOGY: linear (ii) MOLECULE TYPE:  cDNA to genomic RNA (iii) HYPOTHETICAL:

(iv) ANTI-SENSE:

(v) FRAGMENT TYPE:

(vi) ORIGINAL SOURCE:
           (A) ORGANISM:  A/Ibaraki/1/90
           (B) STRAIN:
           (C) INDIVIDUAL ISOLATE:
           (D) DEVELOPMENTAL STAGE:
           (E) HAPLOTYPE:
           (F) TISSUE TYPE:
           (G) CELL TYPE:
           (H) CELL LINE:
           (I) ORGANELLE:

(vii) IMMEDIATE SOURCE:
           (A) LIBRARY:
           (B) CLONE:

(viii) POSITION IN GENOME:
           (A) CHROMOSOME/SEGMENT:
           (B) MAP POSITION:
           (C) UNITS:

(ix) FEATURE:
           (A) NAME/KEY:
           (B) LOCATION:
           (C) IDENTIFICATION METHOD:
           (D) OTHER INFORMATION:

(x) PUBLICATION INFORMATION:
           (A) AUTHORS:
           (B) TITLE:
           (C) JOURNAL:
           (D) VOLUME:
           (E) ISSUE:
           (F) PAGES:
           (G) DATE:
           (H) DOCUMENT NUMBER:
           (I) FILING DATE:
           (J) PUBLICATION DATE:
           (K) RELEVANT RESIDUES IN SEQ ID NO:

(xi) SEQUENCE DESCRIPTION: SEQ ID NO:40:

ATGACAAACC CTTTCAAAAT ATAAACAGGA TCACATATGG GGCATGTCCC AGATATGTTA     60

AGCAAAACAC TCTGAAATTG GCAACAGGGA TGCGGAATGT ACCAGAGAAA CAAACTAGAG    120

GCATATTCGG CGCAATCGCA GGTTTCATAG AAAATGGTTG GGAGGGAATG GTAGACGGTT    180

GGTACGGTTT CAGGCATCAA AATTCTGAGG GCACAGGACA AGCAGCAGAT CTTAAAAGCA    240

CTCAAGCAGC AATCGACCAA ATCAACGGGA AACTGAATAG GTTAATCGAG AAGACGAACG    300

AGAAATTCCA TCAAATCGAA AAGGAATTCT CAGA                                334

(2) INFORMATION FOR SEQ ID NO:41:

(i) SEQUENCE CHARACTERISTICS:
           (A) LENGTH:  329 base pairs
           (B) TYPE:  nucleic acid
           (C) STRANDEDNESS:  double
           (D) TOPOLOGY:  linear (ii) MOLECULE TYPE:  cDNA to genomic RNA (iii) HYPOTHETICAL:

(iv) ANTI-SENSE:

(v) FRAGMENT TYPE:

```
       (vi) ORIGINAL SOURCE:
            (A) ORGANISM:  A/Suita/1/90
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:41:

ATGACAAACC CTTTCAAAAT GTAAACAGGA TCACATATGG GGCATGTCCC AGATATGTTA      60

AGCAAAACAC TCTGAAATTG GCAACAGGGA TGCGGAATGT ACCAGAAAAA CAAACTAGGG     120

GCATATTCGG CGCAATCGCA GGTTTCATAG AAAATGGTTG GGAGGGAATG GTAGACGGTT     180

GGTACGGTTT CAGGCATCAA AACTCTGAGG GCACAGGACA AGCAGCAGAT CTTAAAAGCA     240

CTCAAGCAGC AATCGACCAA ATCAACGGGA AACTGAATAG GTTAATCGAG AAGACGAACG     300

AGAAATTCCA TCAAACCGAA AAGGAATTC                                      329

(2) INFORMATION FOR SEQ ID NO:42:

(i) SEQUENCE CHARACTERISTICS:
            (A) LENGTH:  30 bases
            (B) TYPE:  nucleic acid
            (C) STRANDEDNESS:  single
            (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
```

```
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:42:

GATCTAGAAG CAAAAGCAGG GGTTATACCA                                                  30

(2) INFORMATION FOR SEQ ID NO:43:

(i) SEQUENCE CHARACTERISTICS:
            (A) LENGTH:  30 bases
            (B) TYPE:  nucleic acid
            (C) STRANDEDNESS:  single
            (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
```

```
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:43:

CGGCTAGCAA AAGCAGGGGT TATACCATAG                                              30

(2) INFORMATION FOR SEQ ID NO:44:

(i) SEQUENCE CHARACTERISTICS:
            (A) LENGTH:   29 bases
            (B) TYPE:   nucleic acid
            (C) STRANDEDNESS:   single
            (D) TOPOLOGY:   linear (ii) MOLECULE TYPE:   other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:44:

ACAGATCTAG TAGAAACAAG GGTGTTTTT                                               29

(2) INFORMATION FOR SEQ ID NO:45:

(i) SEQUENCE CHARACTERISTICS:
```

```
        (A) LENGTH:  30 bases
        (B) TYPE:  nucleic acid
        (C) STRANDEDNESS:  single
        (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:45:

CGGCTAGCAG AAACAAGGGT GTTTTTAATT                                           30

(2) INFORMATION FOR SEQ ID NO:46:

(i) SEQUENCE CHARACTERISTICS:
        (A) LENGTH:  1783 base pairs
        (B) TYPE:  nucleic acid
        (C) STRANDEDNESS:  double
        (D) TOPOLOGY:  linear (ii) MOLECULE TYPE:  cDNA to genomic RNA (iii) HYPOTHETICAL:

(iv) ANTI-SENSE:

(v) FRAGMENT TYPE:

(vi) ORIGINAL SOURCE:
        (A) ORGANISM:  A/Okuda/57
        (B) STRAIN:
        (C) INDIVIDUAL ISOLATE:
        (D) DEVELOPMENTAL STAGE:
        (E) HAPLOTYPE:
```

```
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:46:

CGGCTAGCAA AAGCAGGGGT TATACCATAG AAAACCAAAA GCAAAACA                  48

ATG GCC ATC ATT TAT CTC ATT CTC CTG TTC ACA GCA GTG AGA GGG           93
Met Ala Ile Ile Tyr Leu Ile Leu Leu Phe Thr Ala Val Arg Gly
-15              -10                 -5

GAC CAG ATA TGC ATT GGA TAC CAT GCC AAT AAT TCC ACA GAG AAG          138
Asp Gln Ile Cys Ile Gly Tyr His Ala Asn Asn Ser Thr Glu Lys
  1           5                  10                  15

GTC GAC ACA ATT CTA GAG CGG AAC GTC ACT GTG ACT CAT GCC AAG          183
Val Asp Thr Ile Leu Glu Arg Asn Val Thr Val Thr His Ala Lys
              20                  25                  30

GAC ATC CTT GAG AAG ACC CAT AAC GGA AAG TTA TGC AAA CTA AAC          228
Asp Ile Leu Glu Lys Thr His Asn Gly Lys Leu Cys Lys Leu Asn
              35                  40                  45

GGA ATC CCT CCA CTT GAA CTA GGG GAC TGT AGC ATT GCC GGA TGG          273
Gly Ile Pro Pro Leu Glu Leu Gly Asp Cys Ser Ile Ala Gly Trp
              50                  55                  60

CTC CTT GGA AAT CCA AAA TGT GAT AGG CTT CTA AGT GTG CCA GAA          318
Leu Leu Gly Asn Pro Lys Cys Asp Arg Leu Leu Ser Val Pro Glu
              65                  70                  75

CGG TCC TAT ATA TTG GAG AAA GAA AAC CCG AGA GAC GGT TTG TGT          363
Arg Ser Tyr Ile Leu Glu Lys Glu Asn Pro Arg Asp Gly Leu Cys
              80                  85                  90

TAT CCA GGC AGC TTC AAT GAT TAT GAA GAA TTG AAA CAT CTC CTC          408
Tyr Pro Gly Ser Phe Asn Asp Tyr Glu Glu Leu Lys His Leu Leu
              95                 100                 105

AGC AGC GTG AAA CAT TTC GAG AAA GTA AAG ATT CTG CCC AAA GAT          453
Ser Ser Val Lys His Phe Glu Lys Val Lys Ile Leu Pro Lys Asp
             110                 115                 120

AGA TGG ACA CAG CAT ACA ACA ACT GGA GGT TCA CGG GCC TGC GCG          498
Arg Trp Thr Gln His Thr Thr Thr Gly Gly Ser Arg Ala Cys Ala
             125                 130                 135

GTG TCT GGT AAT CCA TCA TTT TTC AGG AAC ATG GTC TGG CTG ACA          543
Val Ser Gly Asn Pro Ser Phe Phe Arg Asn Met Val Trp Leu Thr
```

|     |     |
| --- | --- |
| AAG GAA GGA TCA GAT TAT CCG GTT GCC AAA GGA TCG TAC AAC AAT<br>Lys Glu Gly Ser Asp Tyr Pro Val Ala Lys Gly Ser Tyr Asn Asn<br>                 155                             160                       165 | 588 |
| ACA AGC GGA GAA CAA ATG CTA ATA ATT TGG GGG GTG CAC CAT CCC<br>Thr Ser Gly Glu Gln Met Leu Ile Ile Trp Gly Val His His Pro<br>                 170                             175                       180 | 633 |
| ATT GAT GAG ACA GAA CAA AGA ACA TTG TAC CAG AAT GTG GGA ACC<br>Ile Asp Glu Thr Glu Gln Arg Thr Leu Tyr Gln Asn Val Gly Thr<br>                 185                             190                       195 | 678 |
| TAT GTT TCC GTA GGC ACA TCA ACA TTG AAC AAA AGG TCA ACC CCA<br>Tyr Val Ser Val Gly Thr Ser Thr Leu Asn Lys Arg Ser Thr Pro<br>                 200                             205                       210 | 723 |
| GAA ATA GCA ACA AGG CCT AAA GTG AAT GGA CAA GGA GGT AGA ATG<br>Glu Ile Ala Thr Arg Pro Lys Val Asn Gly Gln Gly Gly Arg Met<br>                 215                             220                       225 | 768 |
| GAA TTC TCT TGG ACC CTC TTG GAT ATG TGG GAC ACC ATA AAT TTT<br>Glu Phe Ser Trp Thr Leu Leu Asp Met Trp Asp Thr Ile Asn Phe<br>                 230                             235                       240 | 813 |
| GAG AGT ACT GGT AAT CTA ATT GCA CCA GAG TAT GGA TTC AAA ATA<br>Glu Ser Thr Gly Asn Leu Ile Ala Pro Glu Tyr Gly Phe Lys Ile<br>                 245                             250                       255 | 858 |
| TCG AAA AGA GGT AGT TCA GGG ATC ATG AAA ACA GAA GGA ACA CTT<br>Ser Lys Arg Gly Ser Ser Gly Ile Met Lys Thr Glu Gly Thr Leu<br>                 260                             265                       270 | 903 |
| GAG AAC TGT GAG ACC AAA TGC CAA ACT CCT TTG GGA GCA ATA AAT<br>Glu Asn Cys Glu Thr Lys Cys Gln Thr Pro Leu Gly Ala Ile Asn<br>                 275                             280                       285 | 948 |
| ACA ACA TTA CCT TTT CAC AAT GTC CAC CCA CTG ACA ATA GGT GAG<br>Thr Thr Leu Pro Phe His Asn Val His Pro Leu Thr Ile Gly Glu<br>                 290                             295                       300 | 993 |
| TGC CCC AAA TAT GTA AAA TCG GAG AAG TTG GTC TTA GCA ACA GGA<br>Cys Pro Lys Tyr Val Lys Ser Glu Lys Leu Val Leu Ala Thr Gly<br>                 305                             310                       315 | 1038 |
| CTA AGG AAT GTT CCC CAG ATT GAA TCA AGA GGA TTG TTT GGG GCA<br>Leu Arg Asn Val Pro Gln Ile Glu Ser Arg Gly Leu Phe Gly Ala<br>                 320                             325                       330 | 1083 |
| ATA GCT GGT TTT ATA GAA GGA GGA TGG CAA GGA ATG GTT GAC GGT<br>Ile Ala Gly Phe Ile Glu Gly Gly Trp Gln Gly Met Val Asp Gly<br>                 335                             330                       345 | 1128 |
| TGG TAT GGA TAC CAT CAC AGC AAT GAC CAG GGA TCA GGG TAT GCA<br>Trp Tyr Gly Tyr His His Ser Asn Asp Gln Gly Ser Gly Tyr Ala<br>                 350                             355                       360 | 1173 |
| GCA GAC AAA GAA TCC ACT CAA AAG GCA TTT GAT GGA ATC ACC AAC<br>Ala Asp Lys Glu Ser Thr Gln Lys Ala Phe Asp Gly Ile Thr Asn<br>                 365                             370                       375 | 1218 |
| AAG GTA AAT TCT GTG ATT GAA AAG ATA AAC ACC CAA TTT GAA GCT<br>Lys Val Asn Ser Val Ile Glu Lys Ile Asn Thr Gln Phe Glu Ala<br>                 380                             385                       390 | 1263 |
| GTT GGG AAA GAA TTC GGT AAC TTA GAG AAA AGA CTG GAG AAC TTG<br>Val Gly Lys Glu Phe Gly Asn Leu Glu Lys Arg Leu Glu Asn Leu<br>                 395                             400                       405 | 1308 |
| AAC AAA AAG ATG GAA GAC GGG TTT CTA GAT GTG TGG ACA TAC AAT<br>Asn Lys Lys Met Glu Asp Gly Phe Leu Asp Val Trp Thr Tyr Asn<br>                 410                             415                       420 | 1353 |
| GCT GAG CTT TTA GTT CTG ATG GAA AAT GAG AGG ACA CTT GAC TTT<br>Ala Glu Leu Leu Val Leu Met Glu Asn Glu Arg Thr Leu Asp Phe<br>                 425                             430                       435 | 1398 |
| CAT GAT TCT AAT GTC AAG AAT CTG TAT AGT AAA GTC AGA ATG CAG | 1443 |

```
His Asp Ser Asn Val Lys Asn Leu Tyr Ser Lys Val Arg Met Gln
            440                 445                 450

CTG AGA GAC AAC GTC AAA GAA CTA GGA AAT GGA TGT TTT GAA TTT        1488
Leu Arg Asp Asn Val Lys Glu Leu Gly Asn Gly Cys Phe Glu Phe
            455                 460                 465

TAT CAC AAA TGT GAT GAT GAA TGC ATG AAT AGT GTG AAA AAC GGG        1533
Tyr His Lys Cys Asp Asp Glu Cys Met Asn Ser Val Lys Asn Gly
            470                 475                 480

ACA TAT GAT TAT CCC AAG TAT GAA GAA GAG TCT AAA CTA AAT AGA        1578
Thr Tyr Asp Tyr Pro Lys Tyr Glu Glu Glu Ser Lys Leu Asn Arg
            495                 500                 505

AAT GAA ATC AAA GGG GTA AAA TTG AGC AGC ATG GGG GTT TAT CAA        1623
Asn Glu Ile Lys Gly Val Lys Leu Ser Ser Met Gly Val Tyr Gln
            510                 515                 520

ATC CTT GCC ATT TAT GCT ACA GTA GCA GGT TCT ATG TCA CTG GCA        1668
Ile Leu Ala Ile Tyr Ala Thr Val Ala Gly Ser Met Ser Leu Ala
            525                 530                 535

ATC ATG ATG GCT GGG ATC TCT TTC TGG GTG TGC TCC AAC GGG TCT        1713
Ile Met Met Ala Gly Ile Ser Phe Trp Val Cys Ser Asn Gly Ser
            540                 545                 550

CTG CAG TGC AGG ATC TGC ATA TGATTATAAG TCATTTTATA ATTAAAAACA       1764
Leu Gln Cys Arg Ile Cys Ile
            555

CCCTTGTTTC TGCTAGCCG                                                1783

(2) INFORMATION FOR SEQ ID NO:47:

(i) SEQUENCE CHARACTERISTICS:
        (A) LENGTH:  25 bases
        (B) TYPE:  nucleic acid
        (C) STRANDEDNESS:  single
        (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
```

```
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:47:

TCCGTTTAGT TTGCATAACT TTCCG                                              25

(2) INFORMATION FOR SEQ ID NO:48:

(i) SEQUENCE CHARACTERISTICS:
          (A) LENGTH:  26 bases
          (B) TYPE:  nucleic acid
          (C) STRANDEDNESS:  single
          (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
          (A) ORGANISM:
          (B) STRAIN:
          (C) INDIVIDUAL ISOLATE:
          (D) DEVELOPMENTAL STAGE:
          (E) HAPLOTYPE:
          (F) TISSUE TYPE:
          (G) CELL TYPE:
          (H) CELL LINE:
          (I) ORGANELLE:

(vii) IMMEDIATE SOURCE:
          (A) LIBRARY:
          (B) CLONE:

(viii) POSITION IN GENOME:
          (A) CHROMOSOME/SEGMENT:
          (B) MAP POSITION:
          (C) UNITS:

(ix) FEATURE:
          (A) NAME/KEY:
          (B) LOCATION:
          (C) IDENTIFICATION METHOD:
          (D) OTHER INFORMATION:

(x) PUBLICATION INFORMATION:
          (A) AUTHORS:
          (B) TITLE:
          (C) JOURNAL:
          (D) VOLUME:
          (E) ISSUE:
          (F) PAGES:
          (G) DATE:
          (H) DOCUMENT NUMBER:
          (I) FILING DATE:
          (J) PUBLICATION DATE:
          (K) RELEVANT RESIDUES IN SEQ ID NO:

(xi) SEQUENCE DESCRIPTION: SEQ ID NO:48:

TCCGGGATCA TGAAAACAGA AGGAAC                                             26

(2) INFORMATION FOR SEQ ID NO:49:

(i) SEQUENCE CHARACTERISTICS:
          (A) LENGTH:  1135 base pairs
```

```
        (B) TYPE: nucleic acid
        (C) STRANDEDNESS: double
        (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
        (A) ORGANISM: A/Okuda/57
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:49:
```

| | |
|---|---|
| CTAGCAAAAG CAGGGGTTAT ACCATAGAAA ACCAAAAGCA AAACAATGGC CATCATTTAT | 60 |
| CTCATTCTCC TGTTCACAGC AGTGAGAGGG GACCAGATAT GCATTGGATA CCATGCCAAT | 120 |
| AATTCCACAG AGAAGGTCGA CACAATTCTA GAGCGGAACG TCACTGTGAC TCATGCCAAG | 180 |
| GACATCCTTG AGAAGACCCA TAACGGAAAG TTATGCAAAC TAAACGGATC CGGGATCATG | 240 |
| AAAACAGAAG GAACACTTGA GAACTGTGAG ACCAAATGCC AAACTCCTTT GGGAGCAATA | 300 |
| AATACAACAT TACCTTTTCA CAATGTCCAC CCACTGACAA TAGGTGAGTG CCCCAAATAT | 360 |
| GTAAAATCGG AGAAGTTGGT CTTAGCAACA GGACTAAGGA ATGTTCCCCA GATTGAATCA | 420 |
| AGAGGATTGT TTGGGGCAAT AGCTGGTTTT ATAGAAGGAG GATGGCAAGG AATGGTTGAC | 480 |
| GGTTGGTATG GATACCATCA CAGCAATGAC CAGGGATCAG GGTATGCAGC AGACAAAGAA | 540 |
| TCCACTCAAA AGGCATTTGA TGGAATCACC AACAAGGTAA ATTCTGTGAT TGAAAGATA | 600 |
| AACACCCAAT TTGAAGCTGT TGGGAAAGAA TTCGGTAACT TAGAGAAAAG ACTGGAGAAC | 660 |
| TTGAACAAAA AGATGGAAGA CGGGTTTCTA GATGTGTGGA CATACAATGC TGAGCTTTTA | 720 |
| GTTCTGATGG AAAATGAGAG GACACTTGAC TTTCATGATT CTAATGTCAA GAATCTGTAT | 780 |

```
AGTAAAGTCA GAATGCAGCT GAGAGACAAC GTCAAAGAAC TAGGAAATGG ATGTTTTGAA      840

TTTTATCACA AATGTGATGA TGAATGCATG AATAGTGTGA AAAACGGGAC ATATGATTAT      900

CCCAAGTATG AAGAAGAGTC TAAACTAAAT AGAAATGAAA TCAAAGGGGT AAAATTGAGC      960

AGCATGGGGG TTTATCAAAT CCTTGCCATT TATGCTACAG TAGCAGGTTC TATGTCACTG     1020

GCAATCATGA TGGCTGGGAT CTCTTTCTGG GTGTGCTCCA ACGGGTCTCT GCAGTGCAGG     1080

ATCTGCATAT GATTATAAGT CATTTTATAA TTAAAAACAC CCTTGTTTCT GCTAG          1135
```

(2) INFORMATION FOR SEQ ID NO:50:

(i) SEQUENCE CHARACTERISTICS:
        (A) LENGTH: 348 amino acids
        (B) TYPE: amino acid
        (C) STRANDEDNESS: single
        (D) TOPOLOGY: linear (ii) MOLECULE TYPE: peptide (iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:50:

```
Met Ala Ile Ile Tyr Leu Ile Leu Leu Phe Thr Ala Val Arg Gly
-15             -10                 -5

Asp Gln Ile Cys Ile Gly Tyr His Ala Asn Asn Ser Thr Glu Lys
  1           5                  10                  15

Val Asp Thr Ile Leu Glu Arg Asn Val Thr Val Thr His Ala Lys
             20                  25                  30
```

```
Asp Ile Leu Glu Lys Thr His Asn Gly Lys Leu Cys Lys Leu Asn
            35                  40                  45

Gly Ser Gly Ile Met Lys Thr Glu Gly Thr Leu Glu Asn Cys Glu
            50                  55                  60

Thr Lys Cys Gln Thr Pro Leu Gly Ala Ile Asn Thr Thr Leu Pro
            65                  70                  75

Phe His Asn Val His Pro Leu Thr Ile Gly Glu Cys Pro Lys Tyr
            80                  85                  90

Val Lys Ser Glu Lys Leu Val Leu Ala Thr Gly Leu Arg Asn Val
            95                 100                 105

Pro Gln Ile Glu Ser Arg Gly Leu Phe Gly Ala Ile Ala Gly Phe
           110                 115                 120

Ile Glu Gly Gly Trp Gln Gly Met Val Asp Gly Trp Tyr Gly Tyr
           125                 130                 135

His His Ser Asn Asp Gln Gly Ser Gly Tyr Ala Ala Asp Lys Glu
           140                 145                 150

Ser Thr Gln Lys Ala Phe Asp Gly Ile Thr Asn Lys Val Asn Ser
           155                 160                 165

Val Ile Glu Lys Ile Asn Thr Gln Phe Glu Ala Val Gly Lys Glu
           170                 175                 180

Phe Gly Asn Leu Glu Lys Arg Leu Glu Asn Leu Asn Lys Lys Met
           185                 190                 195

Glu Asp Gly Phe Leu Asp Val Trp Thr Tyr Asn Ala Glu Leu Leu
           200                 205                 210

Val Leu Met Glu Asn Glu Arg Thr Leu Asp Phe His Asp Ser Asn
           215                 220                 225

Val Lys Asn Leu Tyr Ser Lys Val Arg Met Gln Leu Arg Asp Asn
           230                 235                 240

Val Lys Glu Leu Gly Asn Gly Cys Phe Glu Phe Tyr His Lys Cys
           245                 250                 255

Asp Asp Glu Cys Met Asn Ser Val Lys Asn Gly Thr Tyr Asp Tyr
           260                 265                 270

Pro Lys Tyr Glu Glu Glu Ser Lys Leu Asn Arg Asn Glu Ile Lys
           275                 280                 285

Gly Val Lys Leu Ser Ser Met Gly Val Tyr Gln Ile Leu Ala Ile
           290                 295                 300

Tyr Ala Thr Val Ala Gly Ser Met Ser Leu Ala Ile Met Met Ala
           305                 310                 315

Gly Ile Ser Phe Trp Val Cys Ser Asn Gly Ser Leu Gln Cys Arg
           320                 325                 330

Ile Cys Ile (2) INFORMATION FOR SEQ ID NO:51:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:
```

```
       (vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:51:

GATCTAGAAG CAAAGCAGGG GATAATTCTA                                       30

(2) INFORMATION FOR SEQ ID NO:52:

(i) SEQUENCE CHARACTERISTICS:
            (A) LENGTH:  29 bases
            (B) TYPE:  nucleic acid
            (C) STRANDEDNESS:  single
            (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:
```

```
    (ix) FEATURE:
         (A) NAME/KEY:
         (B) LOCATION:
         (C) IDENTIFICATION METHOD:
         (D) OTHER INFORMATION:

(x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:

(xi) SEQUENCE DESCRIPTION: SEQ ID NO:52:

ACAGATCTAG TAGAAACAAG GGTGTTTTT                                           29

(2) INFORMATION FOR SEQ ID NO:53:

(i) SEQUENCE CHARACTERISTICS:
         (A) LENGTH:  30 bases
         (B) TYPE:  nucleic acid
         (C) STRANDEDNESS:  single
         (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
         (A) ORGANISM:
         (B) STRAIN:
         (C) INDIVIDUAL ISOLATE:
         (D) DEVELOPMENTAL STAGE:
         (E) HAPLOTYPE:
         (F) TISSUE TYPE:
         (G) CELL TYPE:
         (H) CELL LINE:
         (I) ORGANELLE:

(vii) IMMEDIATE SOURCE:
         (A) LIBRARY:
         (B) CLONE:

(viii) POSITION IN GENOME:
         (A) CHROMOSOME/SEGMENT:
         (B) MAP POSITION:
         (C) UNITS:

(ix) FEATURE:
         (A) NAME/KEY:
         (B) LOCATION:
         (C) IDENTIFICATION METHOD:
         (D) OTHER INFORMATION:

(x) PUBLICATION INFORMATION:
         (A) AUTHORS:
         (B) TITLE:
         (C) JOURNAL:
         (D) VOLUME:
         (E) ISSUE:
         (F) PAGES:
         (G) DATE:
         (H) DOCUMENT NUMBER:
         (I) FILING DATE:
         (J) PUBLICATION DATE:
         (K) RELEVANT RESIDUES IN SEQ ID NO:
```

(xi) SEQUENCE DESCRIPTION: SEQ ID NO:53:

```
CGGCTAGCAG AAACAAGGGT GTTTTTAATT                                          30
```

(2) INFORMATION FOR SEQ ID NO:54:

(i) SEQUENCE CHARACTERISTICS:
        (A) LENGTH: 1777 base pairs
        (B) TYPE: nucleic acid
        (C) STRANDEDNESS: double
        (D) TOPOLOGY: linear (ii) MOLECULE TYPE: cDNA to genomic RNA (iii) HYPOTHETICAL:

(iv) ANTI-SENSE:

(v) FRAGMENT TYPE:

(vi) ORIGINAL SOURCE:
        (A) ORGANISM: A2/Aichi/2/68
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:
        (B) LOCATION:
        (C) IDENTIFICATION METHOD:
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:54:

```
GATCTAGAAG CAAAGCAGGG GATAATTCTA TTAATC                                   36

ATG AAG ACC ATC ATT GCT TTG AGC TAC ATT TTC TGT CTG GCT CTC               81
Met Lys Thr Ile Ile Ala Leu Ser Tyr Ile Phe Cys Leu Ala Leu
-15               -10                 -5

GGC CAA GAC CTT CCA GGA AAT GAC AAC AGC ACA GCA ACG CTG TGC              126
Gly Gln Asp Leu Pro Gly Asn Asp Asn Ser Thr Ala Thr Leu Cys
         1               5                  10

CTG GGA CAT CAT GCG GTG CCA AAC GGA ACA CTA GTG AAA ACA ATC              171
Leu Gly His His Ala Val Pro Asn Gly Thr Leu Val Lys Thr Ile
 15               20                  25

ACA GAT GAT CAG ATT GAA GTG ACT AAT GCT ACT GAG CTA GTT CAG              216
Thr Asp Asp Gln Ile Glu Val Thr Asn Ala Thr Glu Leu Val Gln
```

```
           30                  35                  40
AGC TCC TCA ACG GGG AAA ATA TGC AAC AAT CCT CAT CGA ATC CTT    261
Ser Ser Ser Thr Gly Lys Ile Cys Asn Asn Pro His Arg Ile Leu
 45                  50                  55

GAT GGA ATA GAC TGC ACA CTG ATA GAT GCT CTA TTG GGG GAC CCT    306
Asp Gly Ile Asp Cys Thr Leu Ile Asp Ala Leu Leu Gly Asp Pro
 60                  65                  70

CAT TGT GAT GTT TTT CAA AAT GAG ACA TGG GAC CTT TTC GTT GAA    351
His Cys Asp Val Phe Gln Asn Glu Thr Trp Asp Leu Phe Val Glu
 75                  80                  85

CGC AGC AAA GCT TTC AGC AAC TGT TAC CCT TAT GAT GTG CCA GAT    396
Arg Ser Lys Ala Phe Ser Asn Cys Tyr Pro Tyr Asp Val Pro Asp
 90                  95                 100

TAT GCC TCC CTT AGG TCA CTA GTT GCC TCG TCA GGC ACT CTG GAG    441
Tyr Ala Ser Leu Arg Ser Leu Val Ala Ser Ser Gly Thr Leu Glu
105                 110                 115

TTT ATC ACT GAG GGT TTC ACT TGG ACT GGG GTC ACT CAG AAT GGG    486
Phe Ile Thr Glu Gly Phe Thr Trp Thr Gly Val Thr Gln Asn Gly
120                 125                 130

GGA AGC AAT GCT TGC AAA AGG GGA CCT GGT AGC GGT TTT TTC AGT    531
Gly Ser Asn Ala Cys Lys Arg Gly Pro Gly Ser Gly Phe Phe Ser
135                 140                 145

AGA CTG AAC TGG TTG ACC AAA TCA GGA AGC ACA TAT CCA GTG CTG    576
Arg Leu Asn Trp Leu Thr Lys Ser Gly Ser Thr Tyr Pro Val Leu
150                 155                 160

AAC GTG ACT ATG CCA AAC AAT GAC AAT TTT GAC AAA CTA TAC ATT    621
Asn Val Thr Met Pro Asn Asn Asp Asn Phe Asp Lys Leu Tyr Ile
165                 170                 175

TGG GGG ATT CAC CAC CCG AGC ACG AAC CAA GAA CAA ACC AGC CTG    666
Trp Gly Ile His His Pro Ser Thr Asn Gln Glu Gln Thr Ser Leu
180                 185                 190

TAT GTT CAA GCA TCA GGG AGA GTC ACA GTC TCT ACC AGG AGA AGC    711
Tyr Val Gln Ala Ser Gly Arg Val Thr Val Ser Thr Arg Arg Ser
195                 200                 205

CAG CAA ACT ATA ATC CCG AAT ATC GGG TCC AGA CCC TGG GTA AGG    756
Gln Gln Thr Ile Ile Pro Asn Ile Gly Ser Arg Pro Trp Val Arg
210                 215                 220

GGT CTG TCT AGT AGA ATA AGC ATC TAT TGG ACA ATA GTT AAG CCG    801
Gly Leu Ser Ser Arg Ile Ser Ile Tyr Trp Thr Ile Val Lys Pro
225                 230                 235

GGA GAC GTA CTG GTA ATT AAT AGT AAT GGG AAC CTA ATC GCT CCT    846
Gly Asp Val Leu Val Ile Asn Ser Asn Gly Asn Leu Ile Ala Pro
240                 245                 250

CGG GGT TAT TTC AAA ATG CGC ACT GGG AAA AGC TCA ATA ATG AGG    891
Arg Gly Tyr Phe Lys Met Arg Thr Gly Lys Ser Ser Ile Met Arg
255                 260                 265

TCA GAT GCA CCT ATT GAT ACC TGT ATT TCT GAA TGC ATC ACT CCA    936
Ser Asp Ala Pro Ile Asp Thr Cys Ile Ser Glu Cys Ile Thr Pro
270                 275                 280

AAT GGA AGC ATT CCC AAT GAC AAG CCC TTT CAA AAC GTA AAC AAG    981
Asn Gly Ser Ile Pro Asn Asp Lys Pro Phe Gln Asn Val Asn Lys
285                 290                 295

ATC ACA TAT GGA GCA TGC CCC AAG TAT GTT AAG CAA AAC ACC CTG   1026
Ile Thr Tyr Gly Ala Cys Pro Lys Tyr Val Lys Gln Asn Thr Leu
300                 305                 310

AAG TTG GCA ACA GGG ATG CGG AAT GTA CCA GAG AAA CAA ACT AGA   1071
Lys Leu Ala Thr Gly Met Arg Asn Val Pro Glu Lys Gln Thr Arg
315                 320                 325

GGC CTA TTC GGC GCA ATA GCA GGT TTC ATA GAA AAT GGT TGG GAG   1116
```

```
Gly Leu Phe Gly Ala Ile Ala Gly Phe Ile Glu Asn Gly Trp Glu
330                 335                 340

GGA ATG ATA GAC GGT TGG TAC GGT TTC AGG CAT CAA AAT TCT GAG          1161
Gly Met Ile Asp Gly Trp Tyr Gly Phe Arg His Gln Asn Ser Glu
345                 350                 355

GGC ACA GGA CAA GCA GCA GAT CTT AAA AGC ACT CAA GCA GCC ATC          1206
Gly Thr Gly Gln Ala Ala Asp Leu Lys Ser Thr Gln Ala Ala Ile
360                 365                 370

GAC CAA ATC AAT GGG AAA TTG AAC AGG GTA ATC GAG AAG ACG AAC          1251
Asp Gln Ile Asn Gly Lys Leu Asn Arg Val Ile Glu Lys Thr Asn
375                 380                 385

GAG AAA TTC CAT CAA ATC GAA AAG GAA TTC TCA GAA GTA GAA GGG          1296
Glu Lys Phe His Gln Ile Glu Lys Glu Phe Ser Glu Val Glu Gly
390                 395                 400

AGA ATT CAG GAC CTC GAG AAA TAC GTT GAA GAC ACT AAA ATA GAT          1341
Arg Ile Gln Asp Leu Glu Lys Tyr Val Glu Asp Thr Lys Ile Asp
405                 410                 415

CTC TGG TCT TAC AAT GCG GAG CTT CTT GTC GCT CTG GAG AAT CAA          1386
Leu Trp Ser Tyr Asn Ala Glu Leu Leu Val Ala Leu Glu Asn Gln
420                 425                 430

CAT ACA ATT GAC CTG ACT GAC TCG GAA ATG AAC AAG CTG TTT GAA          1431
His Thr Ile Asp Leu Thr Asp Ser Glu Met Asn Lys Leu Phe Glu
435                 440                 445

AAA ACA AGG AGG CAA CTG AGG GAA AAT GCT GAA GAG ATG GGC AAT          1476
Lys Thr Arg Arg Gln Leu Arg Glu Asn Ala Glu Glu Met Gly Asn
450                 455                 460

GGT TGC TTC AAA ATA TAC CAC AAA TGT GAC AAC GCT TGC ATA GAG          1521
Gly Cys Phe Lys Ile Tyr His Lys Cys Asp Asn Ala Cys Ile Glu
465                 470                 475

TCA ATC AGA AAT GGT ACT TAT GAC CAT GAT GTA TAC AGA GAC GAA          1566
Ser Ile Arg Asn Gly Thr Tyr Asp His Asp Val Tyr Arg Asp Glu
480                 485                 490

GCA TTA AAC AAC CGG TTT CAG ATC AAA GGT GTT GAA CTG AAG TCT          1611
Ala Leu Asn Asn Arg Phe Gln Ile Lys Gly Val Glu Leu Lys Ser
495                 500                 505

GGA TAC AAA GAC TGG ATC CTG TGG ATT TCC TTT GCC ATA TCA TGC          1656
Gly Tyr Lys Asp Trp Ile Leu Trp Ile Ser Phe Ala Ile Ser Cys
510                 515                 520

TTT TTG CTT TGT GTT GTT TTG CTG GGG TTC ATC ATG TGG GCC TGC          1701
Phe Leu Leu Cys Val Val Leu Leu Gly Phe Ile Met Trp Ala Cys
525                 530                 535

CAG AGA GGC AAC ATT AGG TGC AAC ATT TGC ATT TGAGTGTATT AGTAATTAAA   1754
Gln Arg Gly Asn Ile Arg Cys Asn Ile Cys Ile
40                  545                 550

AACACCCTTG TTTCTGCTAG CCG                                            1777

(2) INFORMATION FOR SEQ ID NO:55:

(i) SEQUENCE CHARACTERISTICS:
        (A) LENGTH:   20 bases
        (B) TYPE:  nucleic acid
        (C) STRANDEDNESS: single
        (D) TOPOLOGY:  linear (ii) MOLECULE TYPE:   other nucleic acid (synthetic DNA)

(iii) HYPOTHETICAL:

(iv) ANTI-SENSE:

(v) FRAGMENT TYPE:

(vi) ORIGINAL SOURCE:
```

```
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(xi) SEQUENCE DESCRIPTION: SEQ ID NO:55:

ATTGTTGCAT ATTTTCCCCG                                                  20

(2) INFORMATION FOR SEQ ID NO:56:

(i) SEQUENCE CHARACTERISTICS:
            (A) LENGTH:  20 bases
            (B) TYPE:  nucleic acid
            (C) STRANDEDNESS: single
            (D) TOPOLOGY:  linear (ii) MOLECULE TYPE:  other nucleic acid (synthetic DNA)

(iii) HYPOTHETICAL:

(iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:
```

```
        (ix) FEATURE:
              (A) NAME/KEY:
              (B) LOCATION:
              (C) IDENTIFICATION METHOD:
              (D) OTHER INFORMATION:

(x) PUBLICATION INFORMATION:
              (A) AUTHORS:
              (B) TITLE:
              (C) JOURNAL:
              (D) VOLUME:
              (E) ISSUE:
              (F) PAGES:
              (G) DATE:
              (H) DOCUMENT NUMBER:
              (I) FILING DATE:
              (J) PUBLICATION DATE:
              (K) RELEVANT RESIDUES IN SEQ ID NO:

(xi) SEQUENCE DESCRIPTION: SEQ ID NO:56:

ATTGATACCT GTATTTCTGA                                            20

(2) INFORMATION FOR SEQ ID NO:57:

(i) SEQUENCE CHARACTERISTICS:
              (A) LENGTH:   1110 base pairs
              (B) TYPE:  nucleic acid
              (C) STRANDEDNESS: double
              (D) TOPOLOGY:  linear (ii) MOLECULE TYPE:  cDNA to genomic RNA (iii) HYPOTHETICAL:

(iv) ANTI-SENSE:

(v) FRAGMENT TYPE:

(vi) ORIGINAL SOURCE:
              (A) ORGANISM:   A2/Aichi/2/68
              (B) STRAIN:
              (C) INDIVIDUAL ISOLATE:
              (D) DEVELOPMENTAL STAGE:
              (E) HAPLOTYPE:
              (F) TISSUE TYPE:
              (G) CELL TYPE:
              (H) CELL LINE:
              (I) ORGANELLE:

(vii) IMMEDIATE SOURCE:
              (A) LIBRARY:
              (B) CLONE:

(viii) POSITION IN GENOME:
              (A) CHROMOSOME/SEGMENT:
              (B) MAP POSITION:
              (C) UNITS:

(ix) FEATURE:
              (A) NAME/KEY:
              (B) LOCATION:
              (C) IDENTIFICATION METHOD:
              (D) OTHER INFORMATION:

(x) PUBLICATION INFORMATION:
              (A) AUTHORS:
              (B) TITLE:
              (C) JOURNAL:
              (D) VOLUME:
              (E) ISSUE:
              (F) PAGES:
              (G) DATE:
              (H) DOCUMENT NUMBER:
              (I) FILING DATE:
              (J) PUBLICATION DATE:
              (K) RELEVANT RESIDUES IN SEQ ID NO:
```

(xi) SEQUENCE DESCRIPTION: SEQ ID NO:57:

```
CTAGAAGCAA AGCAGGGGAT AATTCTATTA ATCATGAAGA CCATCATTGC TTTGAGCTAC      60
ATTTTCTGTC TGGCTCTCGG CCAAGACCTT CCAGGAAATG ACAACAGCAC AGCAACGCTG     120
TGCCTGGGAC ATCATGCGGT GCCAAACGGA ACACTAGTGA AAACAATCAC AGATGATCAG     180
ATTGAAGTGA CTAATGCTAC TGAGCTAGTT CAGAGCTCCT CAACGGGGAA AATATGCAAC     240
AATATTGATA CCTGTATTTC TGAATGCATC ACTCCAAATG GAAGCATTCC CAATGACAAG     300
CCCTTTCAAA ACGTAAACAA GATCACATAT GGAGCATGCC CCAAGTATGT TAAGCAAAAC     360
ACCCTGAAGT TGGCAACAGG GATGCGGAAT GTACCAGAGA AACAAACTAG AGGCCTATTC     420
GGCGCAATAG CAGGTTTCAT AGAAAATGGT TGGGAGGGAA TGATAGACGG TTGGTACGGT     480
TTCAGGCATC AAAATTCTGA GGGCACAGGA CAAGCAGCAG ATCTTAAAAG CACTCAAGCA     540
GCCATCGACC AAATCAATGG GAAATTGAAC AGGGTAATCG AGAAGACGAA CGAGAAATTC     600
CATCAAATCG AAAAGGAATT CTCAGAAGTA GAAGGGAGAA TTCAGGACCT CGAGAAATAC     660
GTTGAAGACA CTAAAATAGA TCTCTGGTCT TACAATGCGG AGCTTCTTGT CGCTCTGGAG     720
AATCAACATA CAATTGACCT GACTGACTCG GAAATGAACA AGCTGTTTGA AAAAACAAGG     780
AGGCAACTGA GGGAAAATGC TGAAGAGATG GGCAATGGTT GCTTCAAAAT ATACCACAAA     840
TGTGACAACG CTTGCATAGA GTCAATCAGA AATGGTACTT ATGACCATGA TGTATACAGA     900
GACGAAGCAT TAAACAACCG GTTTCAGATC AAAGGTGTTG AACTGAAGTC TGGATACAAA     960
GACTGGATCC TGTGGATTTC CTTTGCCATA TCATGCTTTT TGCTTTGTGT TGTTTTGCTG    1020
GGGTTCATCA TGTGGGCCTG CCAGAGAGGC AACATTAGGT GCAACATTTG CATTTGAGTG    1080
TATTAGTAAT TAAAAACACC CTTGTTTCTG                                    1110
```

(2) INFORMATION FOR SEQ ID NO:58:

(i) SEQUENCE CHARACTERISTICS:
        (A) LENGTH:   347 amino acids
        (B) TYPE:   amino acid
        (C) STRANDEDNESS: single
        (D) TOPOLOGY:   linear (ii) MOLECULE TYPE:   peptide (iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY:

-continued

```
      (B) LOCATION:
      (C) IDENTIFICATION METHOD:
      (D) OTHER INFORMATION:

(x) PUBLICATION INFORMATION:
      (A) AUTHORS:
      (B) TITLE:
      (C) JOURNAL:
      (D) VOLUME:
      (E) ISSUE:
      (F) PAGES:
      (G) DATE:
      (H) DOCUMENT NUMBER:
      (I) FILING DATE:
      (J) PUBLICATION DATE:
      (K) RELEVANT RESIDUES IN SEQ ID NO:

(xi) SEQUENCE DESCRIPTION: SEQ ID NO:58:

Met Lys Thr Ile Ile Ala Leu Ser Tyr Ile Phe Cys Leu Ala Leu
    -15              -10                  -5

Gly Gln Asp Leu Pro Gly Asn Asp Asn Ser Thr Ala Thr Leu Cys
      1               5                  10

Leu Gly His His Ala Val Pro Asn Gly Thr Leu Val Lys Thr Ile
 15                  20                  25

Thr Asp Asp Gln Ile Glu Val Thr Asn Ala Thr Glu Leu Val Gln
 30                  35                  40

Ser Ser Ser Thr Gly Lys Ile Cys Asn Asn Ile Asp Thr Cys Ile
 45                  50                  55

Ser Glu Cys Ile Thr Pro Asn Gly Ser Ile Pro Asn Asp Lys Pro
 60                  65                  70

Phe Gln Asn Val Asn Lys Ile Thr Tyr Gly Ala Cys Pro Lys Tyr
 75                  80                  85

Val Lys Gln Asn Thr Leu Lys Leu Ala Thr Gly Met Arg Asn Val
 90                  95                 100

Pro Glu Lys Gln Thr Arg Gly Leu Phe Gly Ala Ile Ala Gly Phe
105                 110                 115

Ile Glu Asn Gly Trp Glu Gly Met Ile Asp Gly Trp Tyr Gly Phe
120                 125                 130

Arg His Gln Asn Ser Glu Gly Thr Gly Gln Ala Ala Asp Leu Lys
135                 140                 145

Ser Thr Gln Ala Ala Ile Asp Gln Ile Asn Gly Lys Leu Asn Arg
150                 155                 160

Val Ile Glu Lys Thr Asn Glu Lys Phe His Gln Ile Glu Lys Glu
165                 170                 175

Phe Ser Glu Val Glu Gly Arg Ile Gln Asp Leu Glu Lys Tyr Val
180                 185                 190

Glu Asp Thr Lys Ile Asp Leu Trp Ser Tyr Asn Ala Glu Leu Leu
195                 200                 205

Val Ala Leu Glu Asn Gln His Thr Ile Asp Leu Thr Asp Ser Glu
210                 215                 220

Met Asn Lys Leu Phe Glu Lys Thr Arg Arg Gln Leu Arg Glu Asn
225                 230                 235

Ala Glu Glu Met Gly Asn Gly Cys Phe Lys Ile Tyr His Lys Cys
240                 245                 250

Asp Asn Ala Cys Ile Glu Ser Ile Arg Asn Gly Thr Tyr Asp His
255                 260                 265

Asp Val Tyr Arg Asp Glu Ala Leu Asn Asn Arg Phe Gln Ile Lys
270                 275                 280
```

-continued

```
Gly Val Glu Leu Lys Ser Gly Tyr Lys Asp Trp Ile Leu Trp Ile
285                 290                 295

Ser Phe Ala Ile Ser Cys Phe Leu Leu Cys Val Val Leu Leu Gly
300                 305                 310

Phe Ile Met Trp Ala Cys Gln Arg Gly Asn Ile Arg Cys Asn Ile
315                 320                 325

Cys Ile
330
```